United States Patent
Myrick et al.

(10) Patent No.: US 6,613,280 B2
(45) Date of Patent: Sep. 2, 2003

(54) DISPOSABLE CARTRIDGE FOR PRODUCING GAS-ENRICHED FLUIDS

(75) Inventors: Stephen E. Myrick, Tustin, CA (US); Gregory P. Watson, Laguna Niguel, CA (US); William R. Patterson, Irvine, CA (US); Paul J. Zalesky, Huntington Beach, CA (US)

(73) Assignee: Therox, Inc., Irvine, CA (US)

(*) Notice: Subject to any disclaimer, the term of this patent is extended or adjusted under 35 U.S.C. 154(b) by 31 days.

(21) Appl. No.: 09/813,062

(22) Filed: Mar. 20, 2001

(65) Prior Publication Data

US 2002/0136662 A1 Sep. 26, 2002

(51) Int. Cl.[7] .................. A61M 1/14; A61M 11/00; A61M 37/00
(52) U.S. Cl. ................ 422/45; 422/44; 128/200.14; 604/4.01; 604/6.14
(58) Field of Search ............... 422/44, 45; 128/200.14, 128/200.19, 200.21, 200.22; 604/4.01, 6.14, 6.16; 261/DIG. 28, 75, 78.1, 78.2

(56) References Cited

U.S. PATENT DOCUMENTS

| | | | | |
|---|---|---|---|---|
| 2,474,665 A | 6/1949 | Guarino | | 128/214 |
| 3,142,296 A | 7/1964 | Love | | 128/214 |

(List continued on next page.)

FOREIGN PATENT DOCUMENTS

| | | | | |
|---|---|---|---|---|
| GB | 1506555 | 4/1978 | | A61M/1/03 |
| WO | WO 92/14404 | 9/1992 | | A61B/6/00 |
| WO | WO 92/14976 | 9/1992 | | F25B/19/00 |
| WO | WO 95/13843 | 5/1995 | | A61M/37/00 |
| WO | WO 96/01593 | 1/1996 | | A61B/19/00 |
| WO | WO 96/17565 | 6/1996 | | A61F/5/00 |
| WO | WO 96/40334 | 12/1996 | | A61M/15/00 |
| WO | WO 96/41987 | 12/1996 | | |
| WO | WO 97/19713 | 6/1997 | | |
| WO | WO 97/49447 | 12/1997 | | A61M/25/00 |
| WO | WO 98/16202 | 4/1998 | | A61K/9/133 |
| WO | WO 98/46340 | 10/1998 | | |
| WO | WO 99/08732 | 2/1999 | | A61M/1/32 |
| WO | WO 99/08733 | 2/1999 | | A61M/1/36 |

OTHER PUBLICATIONS

US Appl. No. 08/915,532 filed Aug. 15, 1997, Spears et al., "Method for Generalized Extracorporeal Support".
Boe et al., "Use of Hyperbaric Oxygen as Oxygen Source in Extracorporeal Oxygenation of Blood," Physiological and Clinical Aspects of Oxygenator Design, Elsevier North–Holland Biomedical Press, Luxembourg, 1976.
Brereton et al., "Nucleation in small capillary tubes," Chemical Physics 230, pp. 253–265, 1998.
Cason et al., "Therapeutic Hyperoxia Diminishes Myocardial Stunning," J Card Surg, pp. 459–464, 1994.
Cason, et al., "Effects of High Arterial Oxygen Tension on Function, Blood Flow Distribution, and Metabolism in Ischemic Myocardium," Circulation, vol. 85, No. 2, pp. 828–838, Feb. 1992.

(List continued on next page.)

Primary Examiner—Henry Bennett
Assistant Examiner—Alfred Basichas

(57) ABSTRACT

A device generates a gas-enriched physiologic fluid and combines it with a bodily fluid to create a gas-enriched bodily fluid. The device may take the form of a disposable cartridge. The cartridge may include a fluid supply chamber for delivering physiologic fluid under pressure to an atomizer. The atomizer delivers fluid droplets into a gas-pressurized atomization chamber to enrich the physiologic fluid with the gas. The gas-enriched physiologic fluid is delivered to a mixing chamber in the cartridge where the gas-enriched physiologic fluid is mixed with a bodily fluid, such as blood, to create a gas-enriched bodily fluid.

32 Claims, 34 Drawing Sheets

U.S. PATENT DOCUMENTS

| | | | |
|---|---|---|---|
| 3,437,450 A | 4/1969 | Greenwood | 23/285.5 |
| 3,512,517 A | 5/1970 | Kadish et al. | 128/2 |
| 4,041,180 A | 8/1977 | Wilson | 426/11 |
| 4,239,729 A | 12/1980 | Hasegawa et al. | 422/48 |
| 4,297,318 A | 10/1981 | Raible | 422/46 |
| 4,317,731 A | 3/1982 | Roberts, Jr. et al. | 210/741 |
| 4,442,843 A | 4/1984 | Rasor et al. | 128/660 |
| 4,466,804 A | 8/1984 | Hino | 604/4 |
| 4,493,692 A | 1/1985 | Reed | 604/4 |
| 4,596,210 A | 6/1986 | Schmidtke | 123/1 A |
| 4,657,756 A | 4/1987 | Rasor et al. | 424/9 |
| 4,664,680 A | 5/1987 | Weber | 55/48 |
| 4,681,119 A | 7/1987 | Rasor et al. | 128/660 |
| 4,735,750 A | 4/1988 | Damann | 261/29 |
| 4,769,241 A | 9/1988 | Heldebrant et al. | 424/161 |
| 4,804,358 A | 2/1989 | Karcher et al. | 600/17 |
| 4,828,543 A | 5/1989 | Weiss et al. | 604/4 |
| 4,871,450 A | 10/1989 | Goodrich et al. | 210/151 |
| 4,874,509 A | 10/1989 | Bullock | 210/169 |
| 4,917,667 A | 4/1990 | Jackson | 604/96 |
| 4,919,895 A | 4/1990 | Heldebrant et al. | 422/129 |
| 4,973,558 A | 11/1990 | Wilson et al. | 435/240.242 |
| 5,006,352 A | 4/1991 | Zelenák née Zoltai et al. | 426/67 |
| 5,084,011 A | 1/1992 | Grady | 604/24 |
| 5,086,620 A | 2/1992 | Spears | 62/51.1 |
| 5,261,875 A | 11/1993 | Spears | 604/24 |
| 5,322,500 A | 6/1994 | Johnson et al. | 604/4 |
| 5,380,307 A | 1/1995 | Chee et al. | 604/264 |
| 5,382,407 A | 1/1995 | Leonard | 42/48 |
| 5,407,426 A | 4/1995 | Spears | 4/24 |
| 5,569,180 A | 10/1996 | Spears | 604/24 |
| 5,573,505 A | 11/1996 | Johnson et al. | 604/56 |
| 5,599,296 A | 2/1997 | Spears | 604/26 |
| 5,693,017 A | 12/1997 | Spears et al. | 604/612 |
| 5,695,717 A | 12/1997 | Polaschegg et al. | 422/48 |
| 5,709,654 A | 1/1998 | Klatz et al. | 604/24 |
| 5,725,492 A | 3/1998 | Igo et al. | 604/4 |
| 5,730,330 A | 3/1998 | Reading | 222/113 |
| 5,730,698 A | 3/1998 | Fischell et al. | 600/3 |
| 5,730,935 A | 3/1998 | Spears | 422/44 |
| 5,735,934 A | 4/1998 | Spears | 75/414 |
| 5,752,929 A | 5/1998 | Klatz et al. | 604/51 |
| 5,766,490 A | 6/1998 | Taylor et al. | 210/758 |
| 5,797,874 A | 8/1998 | Spears | 604/53 |
| 5,797,876 A | 8/1998 | Spears et al. | 604/95 |
| 5,814,222 A | 9/1998 | Zelenák et al. | 210/615 |
| 5,834,519 A | 11/1998 | Spears | 514/938 |
| 5,843,307 A | 12/1998 | Faivre et al. | 210/192 |
| 5,849,191 A | 12/1998 | Agranonik et al. | 210/608 |
| 5,874,093 A | 2/1999 | Eliaz et al. | 424/401 |
| 5,879,282 A | 3/1999 | Fischell et al. | 600/3 |
| 5,885,467 A | 3/1999 | Zelenák et al. | 210/758 |
| 5,888,611 A | 3/1999 | Leonard | 428/113 |
| 5,893,838 A | 4/1999 | Daoud et al. | 604/26 |
| 5,922,305 A | 7/1999 | Spears | 424/43 |
| 5,957,899 A | 9/1999 | Spears et al. | 604/264 |
| 5,958,377 A | 9/1999 | Spears | 424/43 |
| 5,976,119 A | 11/1999 | Spears et al. | 604/508 |
| 6,030,357 A | 2/2000 | Daoud et al. | 604/26 |
| 6,095,134 A * | 8/2000 | Sievers et al. | 128/200.14 |
| 6,123,698 A | 9/2000 | Spears et al. | 604/523 |
| 6,142,971 A | 11/2000 | Daoud et al. | 604/23 |
| 6,169,117 B1 | 1/2001 | Spears | 514/37 |
| 6,180,059 B1 | 1/2001 | Divino, Jr. et al. | 422/45 |
| 6,197,279 B1 | 3/2001 | Spears | 424/43 |
| 6,235,007 B1 | 5/2001 | Divino, Jr. et al. | 604/264 |
| 6,238,645 B1 | 5/2001 | Spears | 424/43 |
| 6,254,825 B1 * | 7/2001 | Friedman | 422/44 |
| 6,269,810 B1 * | 8/2001 | Brooker et al. | 128/203.12 |
| 6,318,361 B1 * | 11/2001 | Sosiak | 128/200.23 |
| 6,344,483 B1 * | 2/2002 | Hallinan et al. | 514/564 |
| 6,346,192 B2 * | 2/2002 | Buhr et al. | 210/314 |
| 6,387,324 B1 * | 5/2002 | Patterson et al. | 422/45 |
| 6,454,997 B1 * | 9/2002 | Divino et al. | 422/44 |
| 6,482,360 B2 * | 11/2002 | Friedman | 422/44 |
| 2002/0136662 A1 * | 9/2002 | Myrick et al. | 422/45 |
| 2002/0138034 A1 * | 9/2002 | Derek et al. | 604/6.14 |

OTHER PUBLICATIONS

Davis et al., "Delivery of Oxygen to Cutaneous Tissue Via a Super Saturated Oxygen (SOS) Emulsion," Journal of Investigative Dermatology, vol. 112, No. 4, p. 632, Apr. 1999.

Dean, "The Formation of Bubbles," Journal of Applied Physics, vol. 15, pp. 446–451, May, 1944.

Finkelstein et al., "Formation of Gas Bubbles in Supersaturated Solutions of Gases in Water," AlChE Journal, vol. 13, No. 9, pp. 1409–1419, Sep., 1985.

Fluosol, "Fluosol® 20% Intravascular Perfluorochemical Emulsion Product Information," Alpha Therapeutic Corporation, Los Angeles, California, pp. 1–8, Dec. 1989.

Fluosol, Product Monograph, Fluosol® 20% Intravascular Perfluorochemical Emulsion, "Delivers Oxygen to Protect the Heart During PTCA," Alpha Therapeutic Corporation, pp. 3–30.

Gerth et al., "Gas Supersaturation Thresholds for Spontaneous Cavitation in Water with Gas Equilibration Pressures up to 570 atm1," Z. Naturforsch, 31a, pp. 1711–1716, Oct. 5, 1976.

Guttikonda et al., "Effect of Topical O2–Supersaturated Normal Saline on UV Light–Induced Mouse Ear Inflammation," SSID Dermatology Session Abstract, vol. 44, No. 1, p. 51A, Jan. 1996.

Harvey et al., "Bubble Formation In Animals," J. Cell. Comp. Physiol., vol. 24, pp. 23–34.

Hemmingsen, "Cavitation in gas–supersaturated solutions," Journal of Applied Physics, vol. 46, No. 1, pp. 213–218, Jan. 1976.

Hemmingsen, "Effects of Surfactants and Electrolytes on the Nucleation of Bubbles in Gas–Supersaturated Solutions," Z. Naturforsch, 33a pp. 164–171, Oct. 25, 1977.

Henney et al., "Post MI Aqueous Oxygen Hyperoxemic Coronary Reperfusion Acutely Improves Canine LV Function Compared to Normoxemic Reperfusion," (Abstracts/Poster TCT–277), Amer. J. Cardiology, p. 100S, Oct. 8, 1998.

Kantor et al., "Coronary Reperfusion with Aqueous Oxygen Improves Left Ventricular Ejection Fraction and May Reduce Mortality in an Ischemic Porcine Model," (Abstracts/Poster TCT–231), Amer. J. Cardiology, p. 86S, Oct. 8, 1998.

Kenrick et al., "Supersaturation of Gases in Liquids," J. Phys. Chem., vol. 28, pp. 1308–1315, 1924.

Maas et al., "Superoxygenation Process Treats Highly Concentrated Wastewaters," Water/Engineering & Management, pp. 29–33, 39, Feb. 1997.

Metschl, "The Supersaturation of Gases in Water and Certain Organic Liquids," vol. 28, pp. 417–437, 1924.

Rubin et al., "Measurements of Critical Supersaturation for Homogeneous Nucleation of Bubbles," American Chemical Society, Dec. 9, 1986.

Shandling et al., "Hyperbaric oxygen and thrombolysis in myocardial infarction: The "HOT MI" Pilot Study," American Heart Journal, vol. 134, No. 3, pp. 544–550, Sep. 1997.

Spears et al., Aqueous Oxygen: A Highly $O_2$–Supersaturated Infusate for Hyperoxemic Treatment of Postischemic Myocardium, (Abstract/Poster TCT–262), The American Journal of Cardiology, Sep. 1997.

Spears et al., "Aqueous Oxygen—A Highly $O_2$–Supersaturated Infusate for Regional Correction of Hypoxemia and Production of Hyperoxemia," Circulation, vol. 96, No. 12, pp. 4385–4391, Dec. 16, 1997.

Spears et al., "Hyperoxemic Perfusion with Aqueous Oxygen Improves LV Function During Experimental Ml–Reperfusion," (Abstract 2038), Circulation, vol. 96, Abstracts from the $70^{th}$ Scientific Sessions, Supplement I, pp. I–364–I–365, 1997.

Spears et al., "Hyperoxemic Reperfusion With Aqueous Oxygen Improves Left Ventricular Function and Microvascular Flow in the Postischemic Canine Myocardium," (Abstract 1185–127), JACC, vol. 31 (Suppl. A) p. 449A, Feb. 1998.

Spears et al., "Intraaortic Infusion of Oxygen in a Rabbit Model," (Abstracts/Poster 1014–155), JACC, vol. 29, Suppl. A, pp. 317A–318A, Feb. 1997.

Spears et al., "Myocardial Protection With a Perfusion Guidewire During Balloon Angioplasty in a Canine Model,"(Abstracts/Poster 1032–30), JACC, vol. 27, Suppl. A. p. 392A, Feb. 1996.

Spears et al., "Potential Intravascular Oxygenation with Oxygen Clathrate Hydrate," (Abstract 388), Abstracts From the $65^{th}$ Scientific Sessions, Circulation, vol. 80, Suppl. I, p. I–97, 1992.

Spears et al., "Subselective Intracoronary Aqueous Oxygen Hyperoxemic Reperfusion After One Hour Coronary Occlusion in Swine Restores Left Ventricular Function," (Abstracts/Poster 1124–165), JACC, vol. 33, Suppl. A, p. 357A, Feb. 1999.

Spears, "Advances in the Management of Respiratory Failure—Aqueous Preparations of Oxygen," American Society for Artificial Internal Organs, Inc., vol. 42, No. 3, May–Jun., 1996.

Stroev et al., "Supersaturated fluorocarbon as an oxygen source," Physiological and Clinical Aspects of Oxygenator Desing, Elsevier North–Holland Biomedical Press, pp. 129–139, Luxembourg, 1976.

Sueda et al., "Evaluation of Two New Liquid–Liquid Oxygenators," ASAIO Journal, pp. 923–928, 1993.

Yusof et al., "Assessment of the Safety and Efficacy of Supersaturated Oxygen Solution: A Novel Method of Reducing Myocardial Ischaemia in PTCA," (Abstracts/Poster TCT–276), Amer. J. Cardiology, p. 100S, Oct. 8, 1998.

* cited by examiner

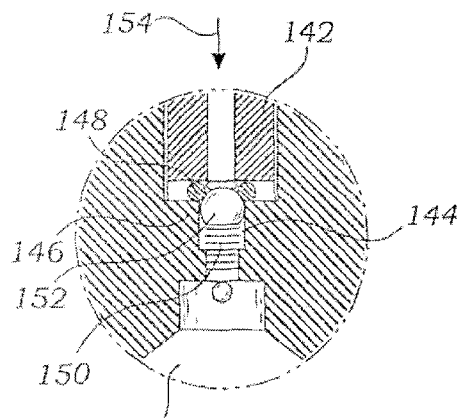
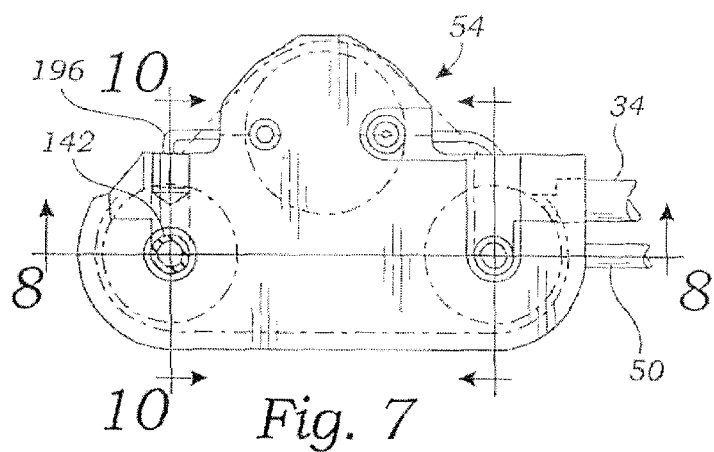
Fig. 10
Fig. 7
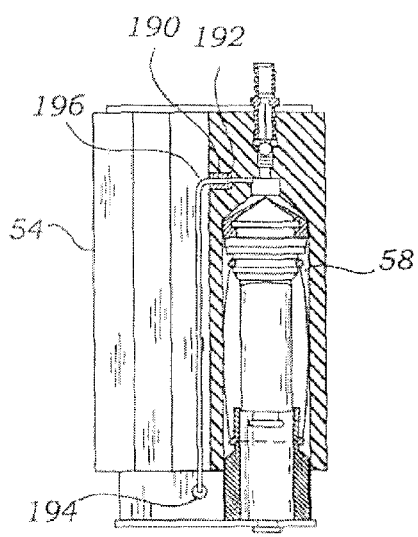
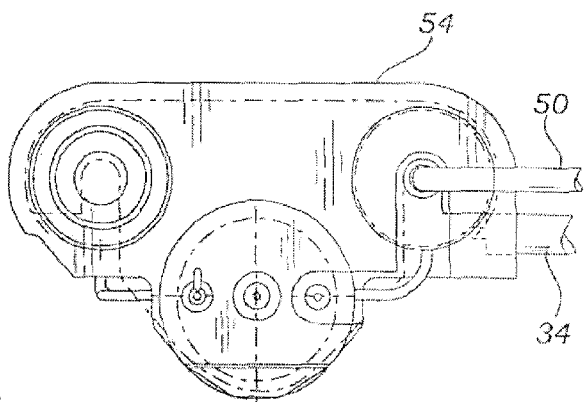
Fig. 9
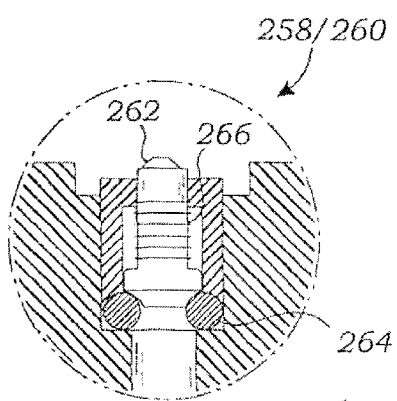
Fig. 12
Fig. 16

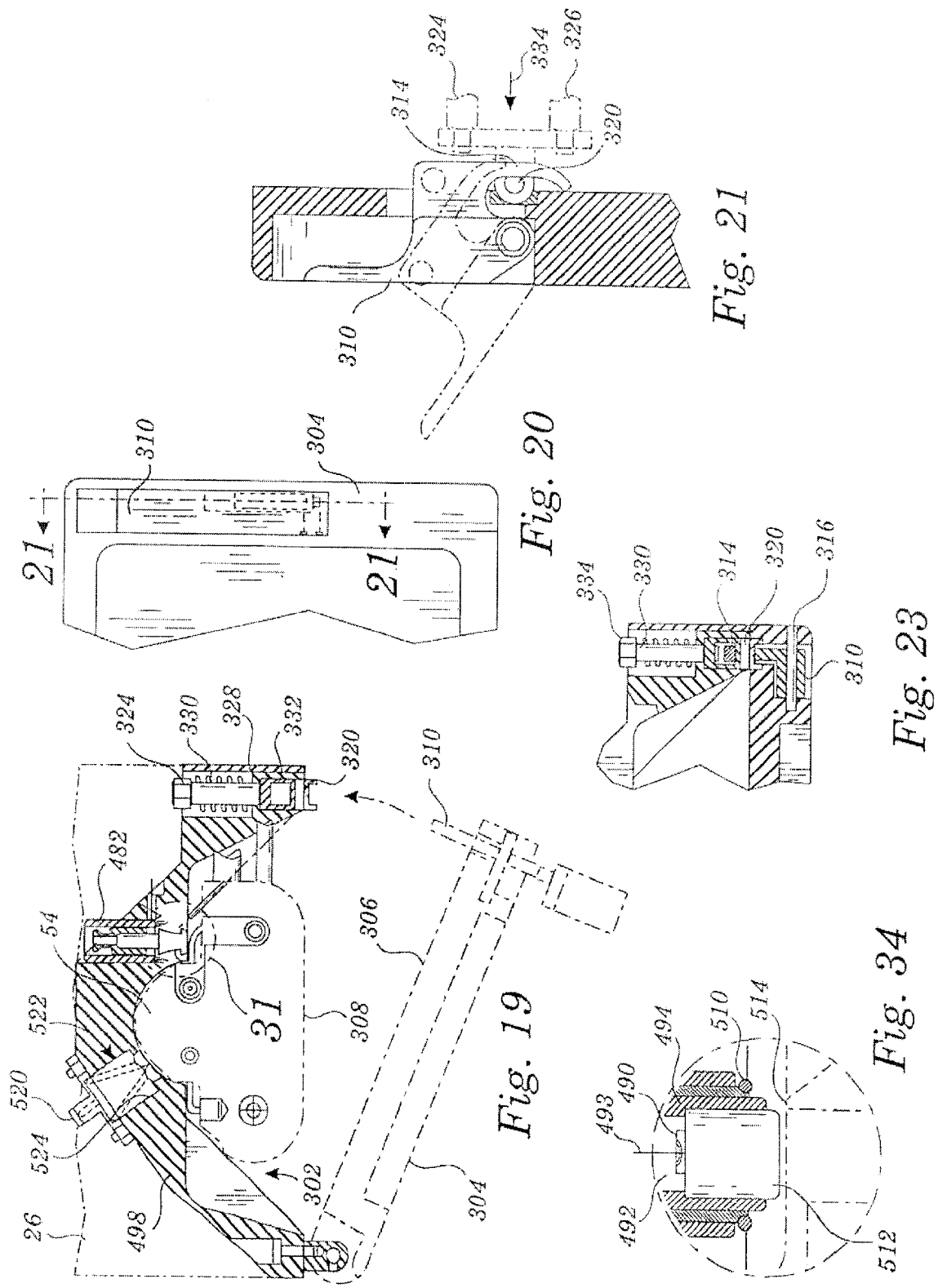

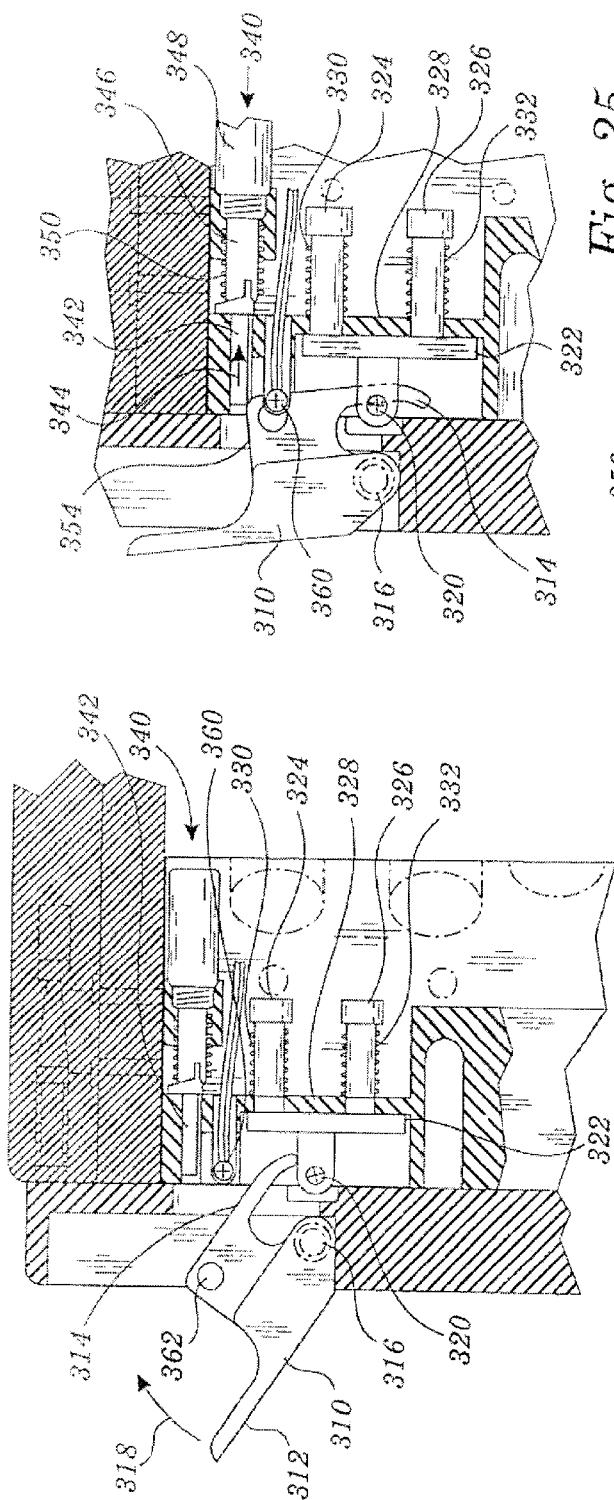
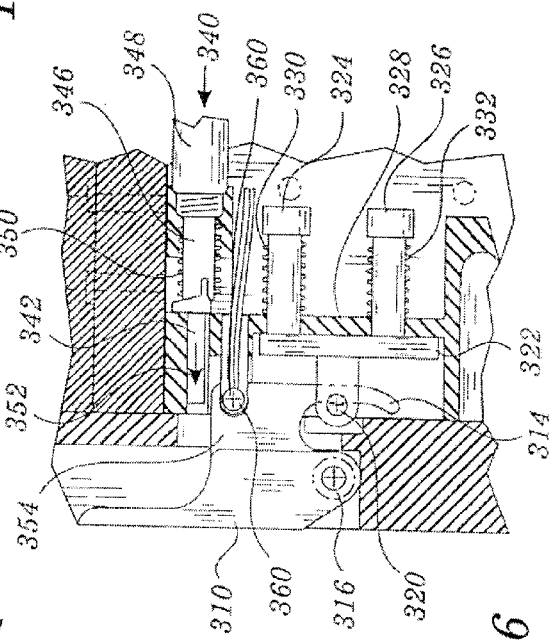
Fig. 24
Fig. 25
Fig. 26

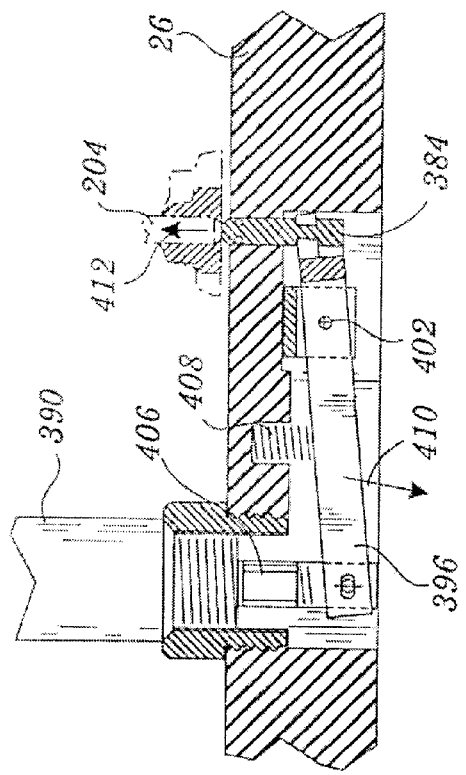
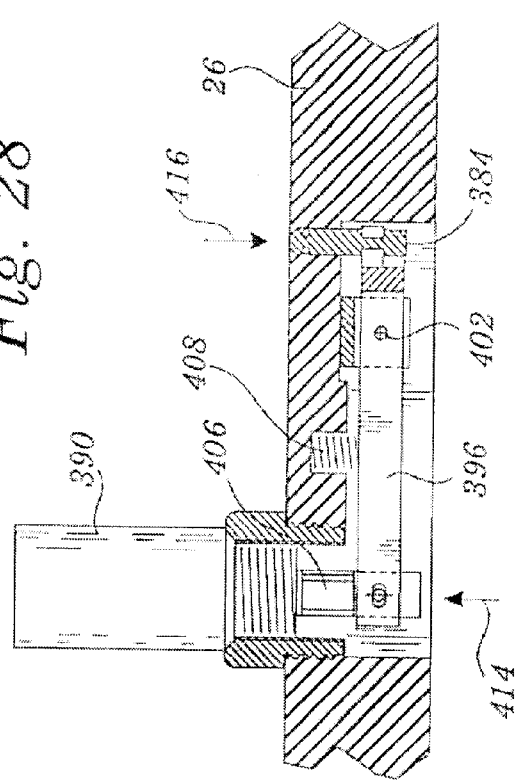
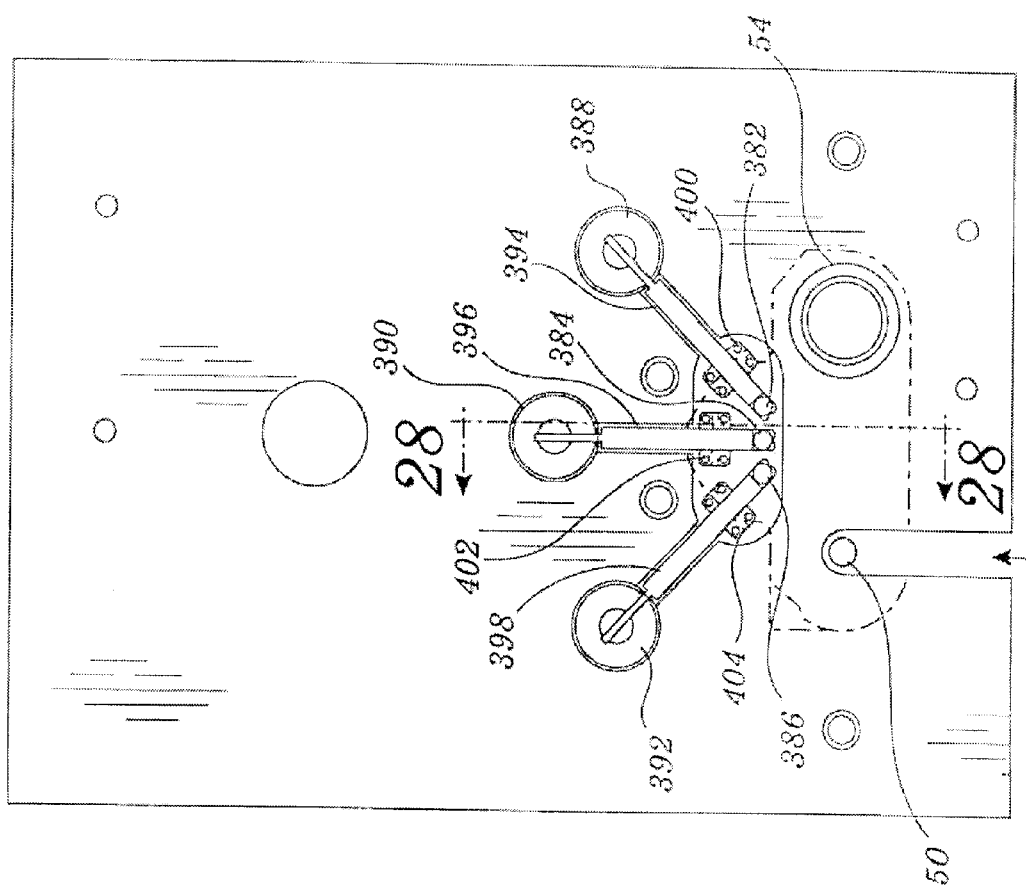

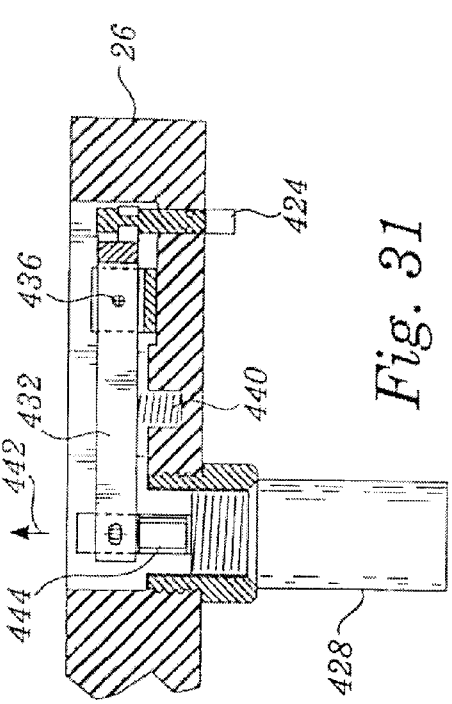
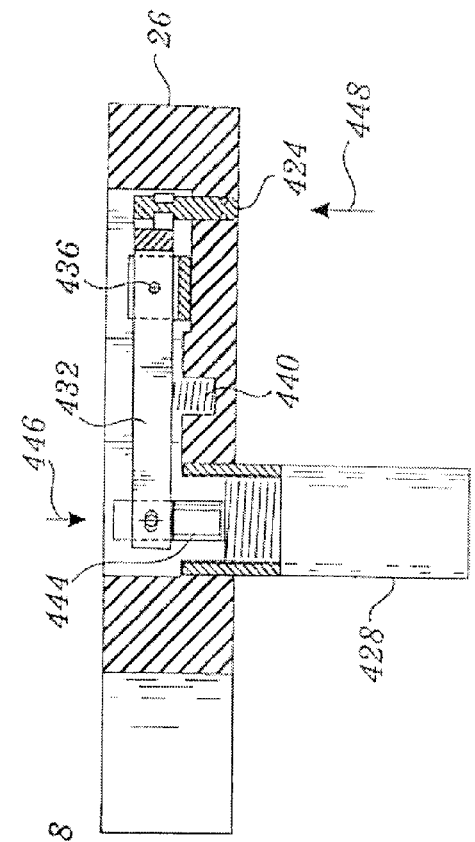
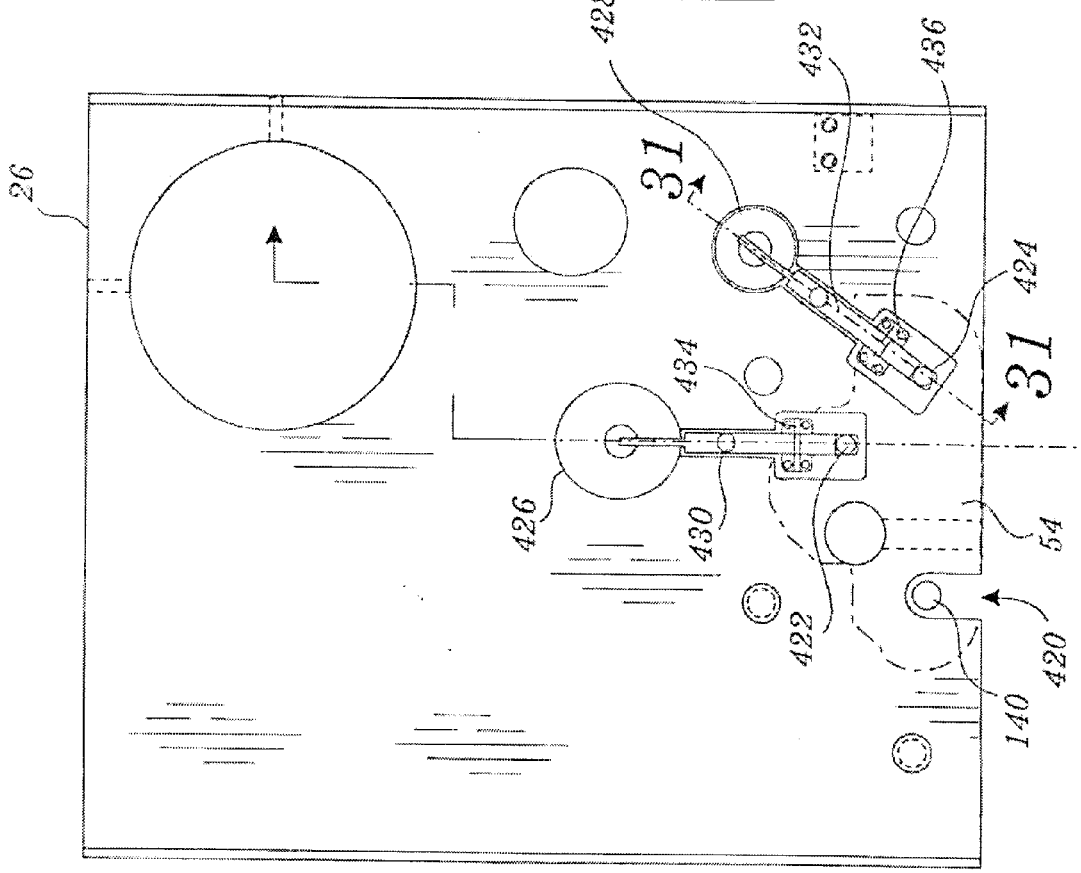

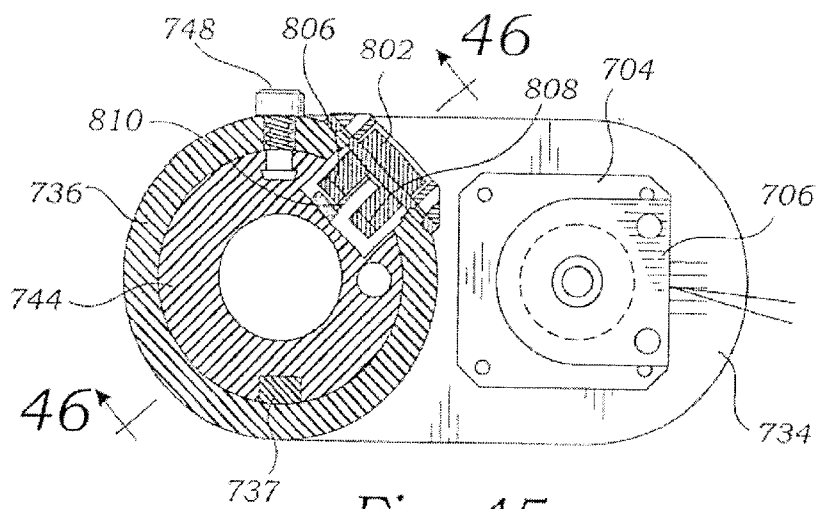
Fig. 45
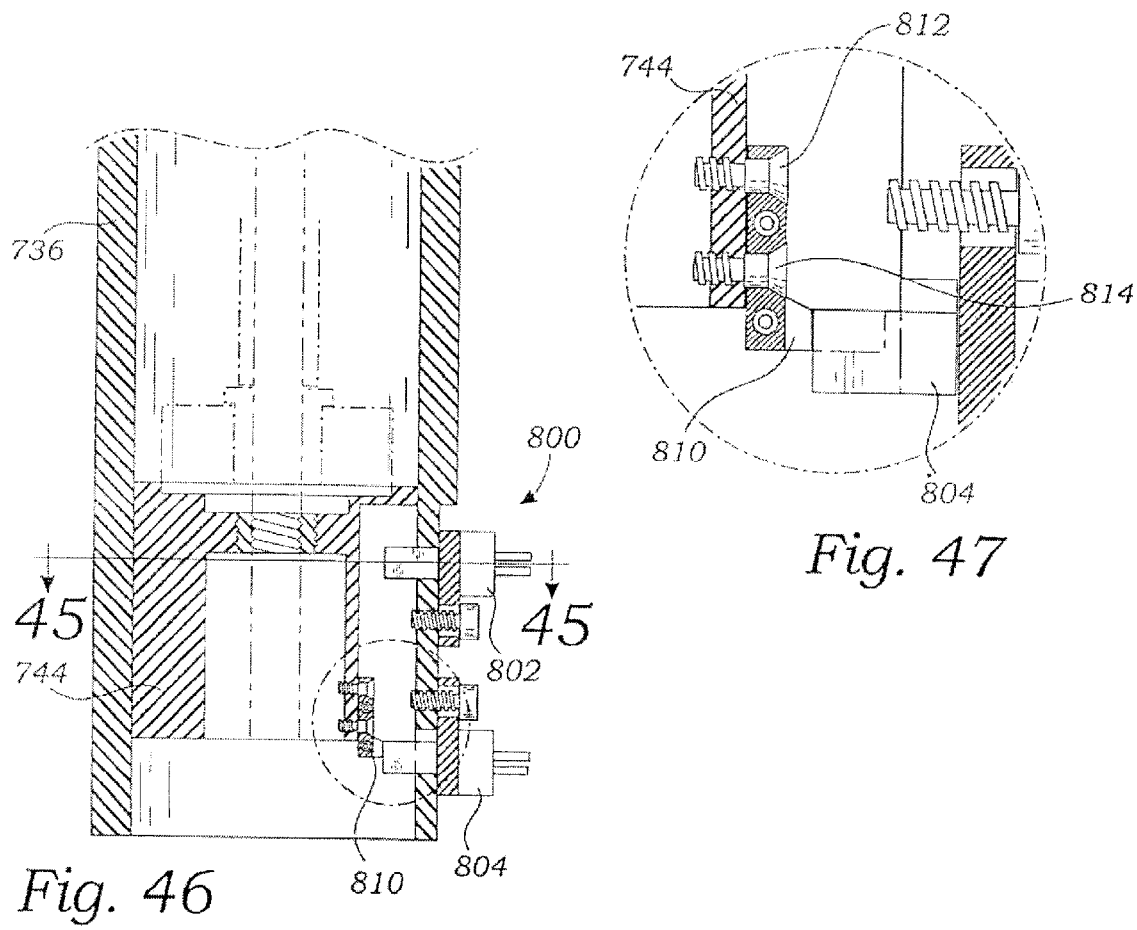
Fig. 46
Fig. 47

DISPOSABLE CARTRIDGE FOR PRODUCING GAS-ENRICHED FLUIDS

BACKGROUND OF THE INVENTION

1. Field of the Invention

The present invention relates generally to the gas enrichment of a fluid and, more particularly, to a disposable cartridge for producing a gas-enriched fluid.

2. Background of the Related Art

This section is intended to introduce the reader to various aspects of art that may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

Gas-enriched fluids are used in a wide variety of medical, commercial, and industrial applications. Depending upon the application, a particular type of fluid is enriched with a particular type of gas to produce a gas-enriched fluid having properties that are superior to the properties of either the gas or fluid alone for the given application. The techniques for delivering gas-enriched fluids also vary dramatically, again depending upon the particular type of application for which the gas-enriched fluid is to be used.

Many commercial and industrial applications exist. As one example, beverages may be purified with the addition of oxygen and carbonated with the addition of carbon dioxide. As another example, the purification of wastewater is enhanced by the addition of oxygen to facilitate aerobic biological degradation. As yet another example, in fire extinguishers, an inert gas, such as nitrogen, carbon dioxide, or argon, may be dissolved in water or another suitable fluid to produce a gas-enriched fluid that expands on impact to extinguish a fire.

While the commercial and industrial applications of gas-enriched fluids are relatively well known, gas-enriched fluids are continuing to make inroads in the healthcare industry. Oxygen therapies, for instance, are becoming more popular in many areas. A broad assortment of treatments involving oxygen, ozone, $H_2O_2$, and other active oxygen supplements has gained practitioners among virtually all medical specialties. Oxygen therapies have been utilized in the treatment of various diseases, including cancer, AIDS, and Alzheimer's. Ozone therapy, for instance, has been used to treat several million people in Europe for a variety of medical conditions including excema, gangrene, cancer, stroke, hepatitis, herpes, and AIDS. Such ozone therapies have become popular in Europe because they tend to accelerate the oxygen metabolism and stimulate the release of oxygen in the bloodstream.

Oxygen is a crucial nutrient for human cells. It produces energy for healthy cell activity and acts directly against foreign toxins in the body. Indeed, cell damage may result from oxygen depravation for even brief periods of time, and such cell damage can lead to organ dysfunction or failure. For example, heart attack and stroke victims experience blood flow obstructions or divergence that prevent oxygen in the blood from being delivered to the cells of vital tissues. Without oxygen, these tissues progressively deteriorate and, in severe cases, death may result from complete organ failure. However, even less severe cases can involve costly hospitalization, specialized treatments, and lengthy rehabilitation.

Blood oxygen levels may be described in terms of the concentration of oxygen that can be achieved in a saturated solution at a given partial pressure of oxygen ($pO_2$). Typically, for arterial blood, normal oxygen levels, i.e., normoxia or normoxemia, range from 90 to 110 mmHg. Hypoxemic blood, i.e., hypoxemia, is arterial blood with a $pO_2$ less than 90 mmHg. Hyperoxemic blood, i.e., hyperoxemia or hyperoxia, is arterial blood with a $pO_2$ greater than 400 mmHg, but less than 760 mmHg. Hyperbaric blood is arterial blood with a $pO_2$ greater than 760 mmHg. Venous blood, on the other hand, typically has a $pO_2$ level less than 90 mmHg. In the average adult, for example, normal venous blood oxygen levels range generally from 40 mmHg to 70 mmHg.

Blood oxygen levels also may be described in terms of hemoglobin saturation levels. For normal arterial blood, hemoglobin saturation is about 97% and varies only as $pO_2$ levels increase. For normal venous blood, hemoglobin saturation is about 75%. Indeed, hemoglobin is normally the primary oxygen carrying component in blood. However, oxygen transfer takes place from the hemoglobin, through the blood plasma, and into the body's tissues. Therefore, the plasma is capable of carrying a substantial quantity of oxygen, although it does not normally do so. Thus, techniques for increasing the oxygen levels in blood primarily enhance the oxygen levels of the plasma, not the hemoglobin.

The techniques for increasing the oxygen level in blood are not unknown. For example, naval and recreational divers are familiar with hyperbaric chamber treatments used to combat the bends, although hyperbaric medicine is relatively uncommon for most people. Since hemoglobin is relatively saturated with oxygen, hyperbaric chamber treatments attempt to oxygenate the plasma. Such hyperoxygenation is believed to invigorate the body's white blood cells, which are the cells that fight infection. Hyperbaric oxygen treatments may also be provided to patients suffering from radiation injuries. Radiation injuries usually occur in connection with treatments for cancer, where the radiation is used to kill the tumor. Unfortunately, at present, radiation treatments also injure surrounding healthy tissue as well. The body keeps itself healthy by maintaining a constant flow of oxygen between cells, but radiation treatments can interrupt this flow of oxygen. Accordingly, hyperoxygenation can stimulate the growth of new cells, thus allowing the body to heal itself.

Radiation treatments are not the only type of medical therapy that can deprive cells from oxygen. In patients who suffer from acute myocardial infarction, for example, if the myocardium is deprived of adequate levels of oxygenated blood for a prolonged period of time, irreversible damage to the heart can result. Where the infarction is manifested in a heart attack, the coronary arteries fail to provide adequate blood flow to the heart muscle. The treatment for acute myocardial infarction or myocardial ischemia often involves performing angioplasty or stenting of vessels to compress, ablate, or otherwise treat the occlusions within the vessel walls. In an angioplasty procedure, for example, a balloon is placed into the vessel and inflated for a short period of time to increase the size of the interior of the vessel. When the balloon is deflated, the interior of the vessel will, hopefully, retain most or all of this increase in size to allow increased blood flow.

However, even with the successful treatment of occluded vessels, a risk of tissue injury may still exist. During percutaneous transluminal coronary angioplasty (PTCA), the balloon inflation time is limited by the patient's tolerance to ischemia caused by the temporary blockage of blood flow through the vessel during balloon inflation. Ischemia is a condition in which the need for oxygen exceeds the supply of oxygen, and the condition may lead to cellular damage or necrosis. Reperfusion injury may also result, for example, due to slow coronary reflow or no reflow following angioplasty. Furthermore, for some patients, angioplasty procedures are not an attractive option for the treatment of vessel blockages. Such patients are typically at increased risk of ischemia for reasons such as poor left ventricular function, lesion type and location, or the amount of myocardium at risk. Treatment options for such patients typically include more invasive procedures, such as coronary bypass surgery.

To reduce the risk of tissue injury that may be associated with treatments of acute myocardial infarction and myocardial ischemia, it is usually desirable to deliver oxygenated blood or oxygen-enriched fluids to the tissues at risk. Tissue injury is minimized or prevented by the diffusion of the dissolved oxygen from the blood to the tissue. Thus, in some cases, the treatment of acute myocardial infarction and myocardial ischemia includes perfusion of oxygenated blood or oxygen-enriched fluids. The term "perfusion" is derived from the French verb "perfuse" meaning "to pour over or through." In this context, however, perfusion refers to various techniques in which at least a portion of the patient's blood is diverted into an extracorporeal circulation circuit, i.e., a circuit which provides blood circulation outside of the patient's body. Typically, the extracorporeal circuit includes an artificial organ that replaces the function of an internal organ prior to delivering the blood back to the patient. Presently, there are many artificial organs that can be placed in an extracorporeal circuit to substitute for a patient's organs. The list of artificial organs includes artificial hearts (blood pumps), artificial lungs (oxygenators), artificial kidneys (hemodialysis), and artificial livers.

During PTCA, for example, the tolerable balloon inflation time may be increased by the concurrent introduction of oxygenated blood into the patient's coronary artery. Increased blood oxygen levels also may cause the hypercontractility in the normally perfused left ventricular cardiac tissue to increase blood flow further through the treated coronary vessels. The infusion of oxygenated blood or oxygen-enriched fluids also may be continued following the completion of PTCA or other procedures, such as surgery, to accelerate the reversal of ischemia and to facilitate recovery of myocardial function.

Conventional methods for the delivery of oxygenated blood or oxygen-enriched fluids to tissues involve the use of blood oxygenators. Such procedures generally involve withdrawing blood from a patient, circulating the blood through an oxygenator to increase blood oxygen concentration, and then delivering the blood back to the patient. There are drawbacks, however, to the use of conventional oxygenators in an extracorporeal circuit. Such systems typically are costly, complex, and difficult to operate. Often, a qualified perfusionist is required to prepare and monitor the system. A perfusionist is a skilled health professional specifically trained and educated to operate as a member of a surgical team responsible for the selection, setup, and operation of an extracorporeal circulation circuit. The perfusionist is responsible for operating the machine during surgery, monitoring the altered circulatory process closely, taking appropriate corrective action when abnormal situations arise, and keeping both the surgeon and anesthesiologist fully informed. In addition to the operation of the extracorporeal circuit during surgery, perfusionists often function in supportive roles for other medical specialties to assist in the conservation of blood and blood products during surgery and to provide long-term support for patient's circulation outside of the operating room environment. Because there are currently no techniques available to operate and monitor an extracorporeal circuit automatically, the presence of a qualified perfusionist, and the cost associated therewith, is typically required.

Conventional extracorporeal circuits also exhibit other drawbacks. For example, extracorporeal circuits typically have a relatively large priming volume. The priming volume is typically the volume of blood contained within the extracorporeal circuit, i.e., the total volume of blood that is outside of the patient's body at any given time. For example, it is not uncommon for the extracorporeal circuit to hold one to two liters of blood for a typical adult patient. Such large priming volumes are undesirable for many reasons. For example, in some cases a blood transfusion may be necessary to compensate for the blood temporarily lost to the extracorporeal circuit because of its large priming volume. Also, heaters often must be used to maintain the temperature of the blood at an acceptable level as it travels through the extracorporeal circuit. Further, conventional extracorporeal circuits are relatively difficult to turn on and off. For instance, if the extracorporeal circuit is turned off, large stagnant pools of blood in the circuit might coagulate.

In addition to the drawbacks mentioned above, in extracorporeal circuits that include conventional blood oxygenators, there is a relatively high risk of inflammatory cell reaction and blood coagulation due to the relatively slow blood flow rates and large blood contact surface area of the oxygenators. For example, a blood contact surface area of about one to two square meters and velocity flows of about 3 centimeters/second are not uncommon with conventional oxygenator systems. Thus, relatively aggressive anticoagulation therapy, such as heparinization, is usually required as an adjunct to using the oxygenator.

Finally, perhaps one of the greatest disadvantages to using conventional blood oxygenation systems relates to the maximum partial pressure of oxygen ($pO_2$) that can be imparted to the blood. Conventional blood oxygenation systems can prepare oxygen-enriched blood having a partial pressure of oxygen of about 500 mmHg. Thus, blood having $pO_2$ levels near or above 760 mmHg, i.e., hyperbaric blood, cannot be achieved with conventional oxygenators.

It is desirable to deliver gas-enriched fluid to a patient in a manner which prevents or minimizes bubble nucleation and formation upon infusion into the patient. The maximum concentration of gas achievable in a liquid is ordinarily governed by Henry's Law. At ambient temperature, the relatively low solubility of many gases, such as oxygen or nitrogen, within a liquid, such as water, produces a low concentration of the gas in the liquid. However, such low concentrations are typically not suitable for treating patients as discussed above. Rather, it is advantageous to use a gas concentration within a liquid that greatly exceeds its solubility at ambient temperature. Compression of a gas and liquid mixture at a high pressure can be used to achieve a high dissolved gas concentration according to Henry's Law, but disturbance of a gas-saturated or a gas-supersaturated liquid by attempts to inject it into an environment at ambient pressure from a high pressure reservoir ordinarily results in cavitation inception at or near the exit port. The rapid evolution of bubbles produced at the exit port vents much of the gas from the liquid, so that a high degree of gas-supersaturation no longer exists in the liquid at ambient pressure outside the high-pressure vessel. In addition, the presence of bubbles in the effluent generates turbulence and impedes the flow of the effluent beyond the exit port. Furthermore, the coalescence of gas bubbles in blood vessels may tend to occlude the vessels and result in a gaseous local embolism that causes a decrease in local circulation, arterial hypoxemia, and systemic hypoxia.

In gas-enriched fluid therapies, such as oxygen therapies involving the use of hyperoxic or hyperbaric blood, delivery techniques are utilized to prevent or minimize the formation of cavitation nuclei so that clinically significant bubbles do not form within a patient's blood vessels. However, it should be understood that any bubbles that are produced tend to be very small in size, so that a perfusionist would typically have difficulty detecting bubble formation without the assistance of a bubble detection device. Unfortunately, known bubble detectors are ineffective for detecting bubbles in an extracorporeal circuit for the preparation and delivery of hyperoxic or hyperbaric blood. This problem results from the fact that the size and velocity of some bubbles are beyond the resolution of known bubble detectors. Therefore, micro bubbles (bubbles with diameters of about 50 micrometers to about 1000 micrometers) and some macro bubbles (bubbles with diameters greater than 1000 micrometers) may escape detection.

BRIEF DESCRIPTION OF THE DRAWINGS

The foregoing and other advantages of the invention will become apparent upon reading the following detailed description and upon reference to the drawings in which:

FIG. 7 illustrates a top view of an oxygenation device used in the system of FIG. 1;

FIG. 9 illustrates a bottom view of the oxygenation device used in the system of FIG. 1;

FIG. 10 illustrates a detailed view of a check valve illustrated in FIG. 8;

FIG. 12 illustrates a cross-sectional view taken along line 12—12 of FIG. 8;

FIG. 13 illustrates a detailed view of a valve assembly illustrated in FIG. 8;

FIG. 14 illustrates a cross-sectional view of the valve assembly taken along line 14—14 in FIG. 13;

FIG. 19 illustrates a cross-sectional view of the cartridge enclosure taken along line 19—19 in FIG. 18;

FIG. 20 illustrates the front view of a door latch on the door of the cartridge enclosure;

FIG. 21 illustrates a cross-sectional view of the door latch taken along line 21—21 in FIG. 20;

FIG. 23 illustrates a detailed view of the door latch of FIG. 19;

FIG. 24 illustrates a cross-sectional view of the door latch including a blocking mechanism;

FIG. 25 illustrates a cross-sectional view of the locking mechanism of FIG. 24 as the latch is being closed;

FIG. 26 illustrates a cross-sectional view of the locking mechanism after the latch has been closed;

FIG. 27 illustrates a bottom view of the cartridge enclosure;

FIG. 28 illustrates a cross-sectional view taken along line 28—28 in FIG. 27 of a valve actuation device in an extended position;

FIG. 29 illustrates a cross-sectional view taken along line 28—28 in FIG. 27 of a valve actuation device in a retracted position;

FIG. 30 illustrates a top-view of the cartridge enclosure;

FIG. 31 illustrates a cross-sectional view taken along line 31—31 of FIG. 30 of a valve actuation device in its extended position;

FIG. 32 illustrates a cross-sectional view taken along line 31—31 of FIG. 30 of a valve actuation device in its retracted position;

FIG. 34 illustrates a detailed view of an ultrasonic sensor illustrated in FIG. 33;

FIG. 45 illustrates a top partial cross-sectional view of the drive assembly;

FIG. 46 illustrates a cross-sectional view taken along line 46—46 of FIG. 45;

FIG. 47 illustrates a detailed view of a portion of the sensor assembly illustrated in FIG. 46;

DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

System Overview

Figure 1:
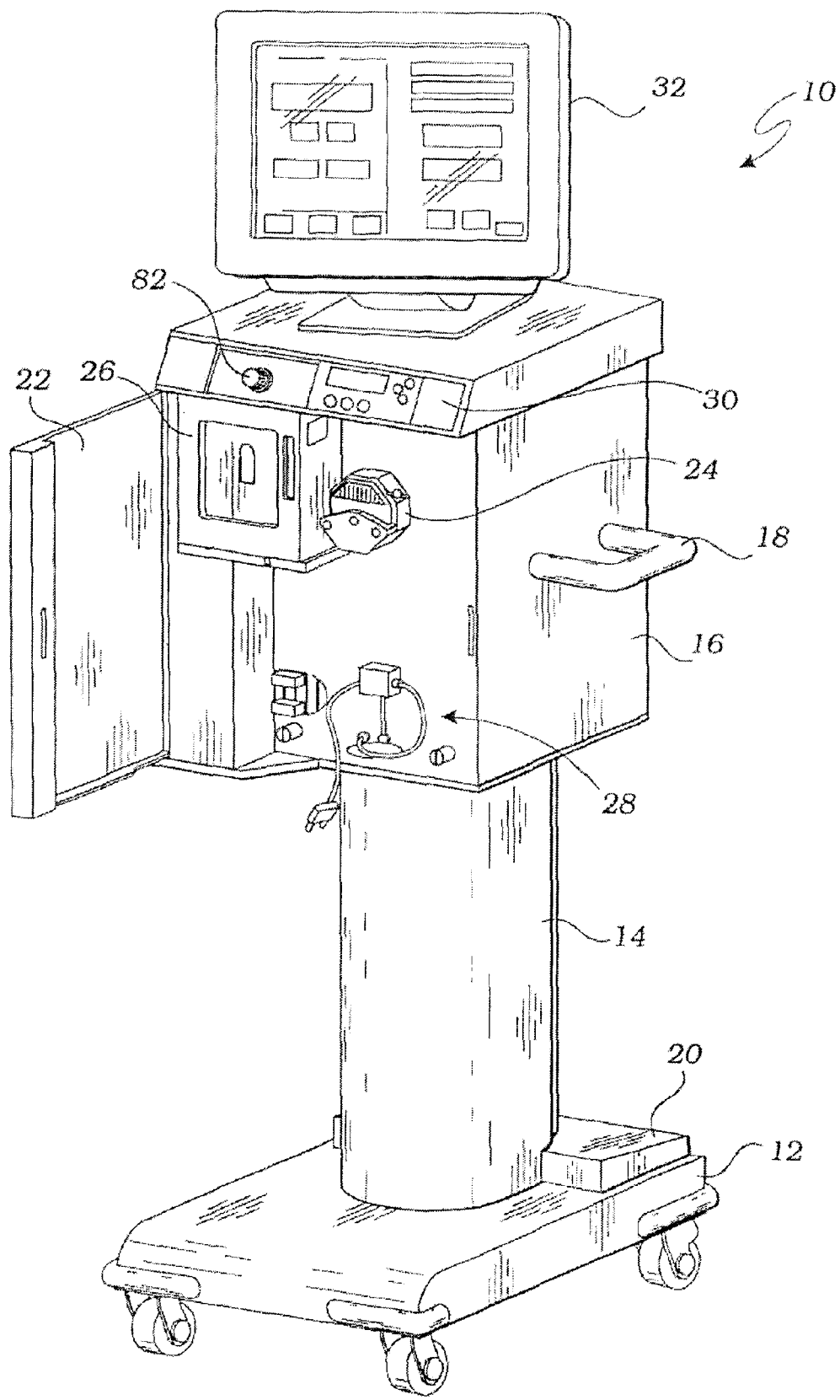
FIG. 1 illustrates a perspective view of an exemplary system for producing gas-enriched fluid.

Turning now to the drawings, and referring initially to FIG. 1, a system for preparing and delivering gas-enriched fluid is illustrated and designated by a reference numeral 10. Although the system 10 may be used to prepare a number of different types of gas-enriched fluids, in this particular example, the system 10 prepares oxygen-enriched blood. As will be described in detail herein, the system 10 is adapted to withdraw blood from a patient, combine the blood with a oxygen-supersaturated physiologic fluid, and deliver the oxygen-enriched blood back to the patient.

Because the system 10 may be used during surgical procedures, it is typically sized to be placed within a normal operating room environment. Although the system 10 may be configured as a stationary device or a fixture within an operating room, it is often desirable for various surgical devices to be mobile. Accordingly, in this example, the system 10 is illustrated as being coupled to a rolling base 12 via a pedestal 14. Although some of the electrical and/or mechanical components of the system 10 may be housed in the base 12 or the pedestal 14, these components will more typically be placed within a housing 16. To facilitate positioning of the system 10, a handle 18 may be coupled to the housing 16 for directing movement of the system 10, and a pedal 20 may be coupled to the base 12 for raising and lowering the housing 16 on the pedestal 14 (via a rack and pinion mechanism which is not shown, for instance).

The housing 16 may include a cover, such as a hinged door 22, for protecting certain components of the system 10 that are positioned in locations external to the housing 16. Components that are typically located on the exterior of the housing 16 may include a blood pump 24, a cartridge enclosure 26, as well as various control devices 28. Additional external items may include a user interface panel 30 and a display 32.

Figure 2:
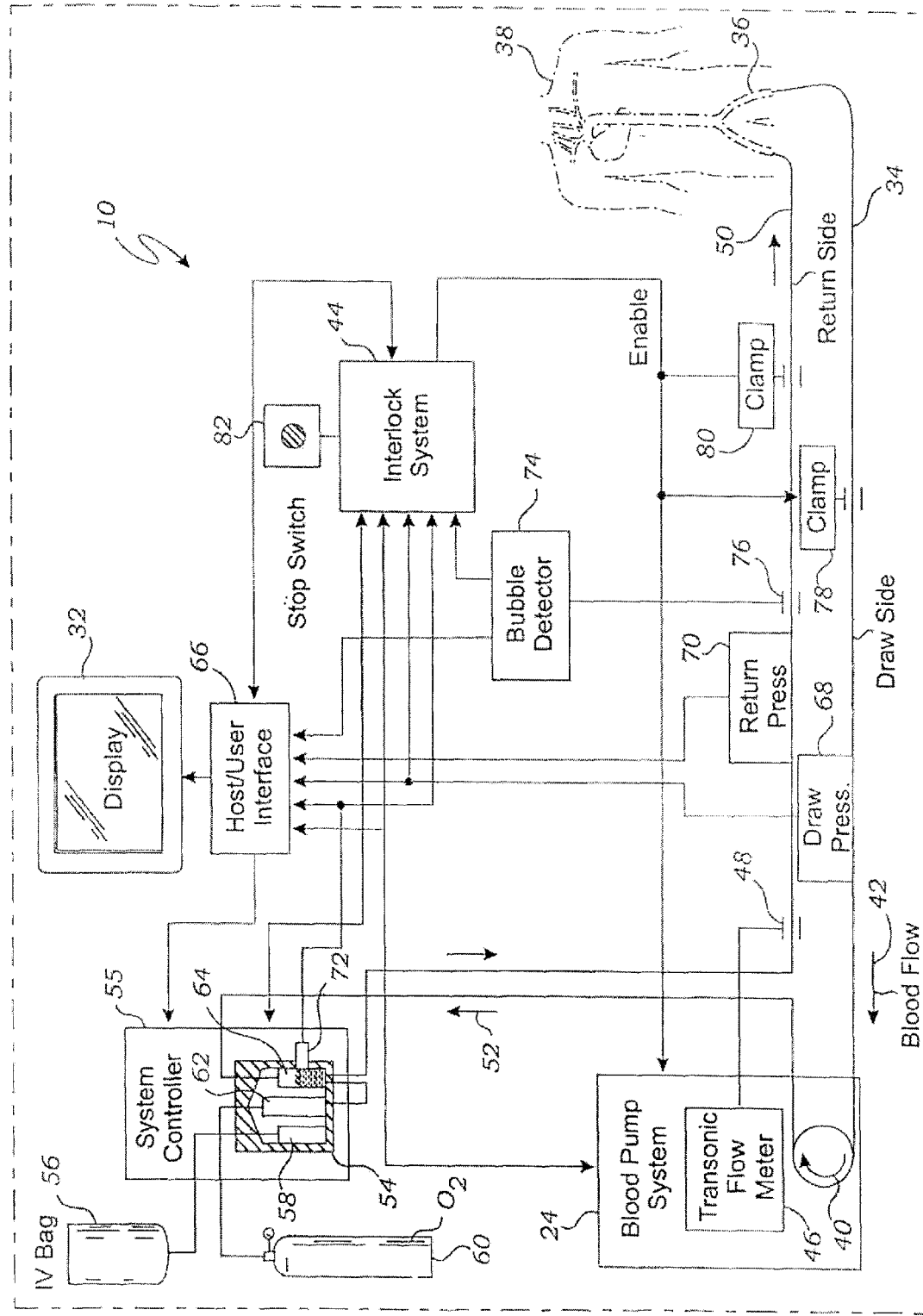
FIG. 2 illustrates a block diagram of the system of FIG. 1.

Referring now to FIG. 2, a block diagram representing various components of the system 10 is illustrated. An appropriate draw tube 34, such as an introducer sheath, is inserted into an appropriate blood vessel 36 of a patient 38. Blood is drawn from the patient 38 through the draw tube 34 using the blood pump system 24. Specifically, the blood pump system 24 includes a pump 40, such as a peristaltic pump. As the peristaltic pump 40 mechanically produces waves of contraction along the flexible tube 34, fluid within the tube 34 is pumped in the direction of the arrow 42. As will be discussed in detail below, the blood pump system 24 includes a flow meter 46 that receives feedback from a flow probe 48. The flow probe 48 is coupled to the patient's return tube 50. With this feedback, the blood pump system 24 can operate as an automatic extracorporeal circuit that can adjust the r.p.m. of the peristaltic pump 40 to maintain the desired blood flow.

The draw tube 34 and/or the return tube 50 may be sub-selective catheters. The construction of the return tube 50 may be of particular importance in light of the fact that the gas-enriched bodily fluid may be gas-saturated or gas-supersaturated over at least a portion of the length of the return tube 50. Therefore, the return tube 50, in particular, is typically designed to reduce or eliminate the creation of cavitation nuclei which may cause a portion of the gas to come out of solution. For example, the length-to-internal diameter ratio of the catheter may be selected to create a relatively low pressure drop from the oxygenation device 54 to the patient 38. Typically, the catheter is sized to fit within a 6 french guide catheter. Materials such as polyethylene or PEBAX (polyetheramide), for example, may be used in the construction of the catheter. Also, the lumen of the catheter should be relatively free of transitions that may cause the creation of cavitation nuclei. For example, a smooth lumen having no fused polymer transitions typically works well.

The blood is pumped through the draw tube 34 in the direction of the arrow 52 into an oxygenation device 54. Although various different types of oxygenation devices may be suitable for oxygenating the patient's blood prior to its return, the oxygenation device 54 in the system 10 advantageously prepares an oxygen-supersaturated physiologic fluid and combines it with the blood to enrich the blood with oxygen. Also, the oxygenation device 54 is advantageously sterile, removable, and disposable, so that after the procedure on the patient 38 has been completed, the oxygenation device 54 may be removed and replaced with another oxygenation device 54 for the next patient.

Advantages of the oxygenation device 54 will be described in great detail below. However, for the purposes of the discussion of FIG. 2, it is sufficient at this point to understand that the physiologic fluid, such as saline, is delivered from a suitable supply 56, such as an IV bag, to a first chamber 58 of the oxygenation device 54 under the control of a system controller 55. A suitable gas, such as oxygen, is delivered from a supply 60, such as a tank, to a second chamber 62 of the oxygenation device 54. Generally speaking, the physiologic fluid from the first chamber 58 is pumped into the second chamber 62 and atomized to create a oxygen-supersaturated physiologic solution. This oxygen-supersaturated physiologic solution is then delivered into a third chamber 64 of the oxygenation device 54 along with the blood from the patient 38. As the patient's blood mixes with the oxygen-supersaturated physiologic solution, oxygen-enriched blood is created. This oxygen-enriched blood is taken from the third chamber 64 of the oxygenation device 54 by the return tube 50.

Figure 6:
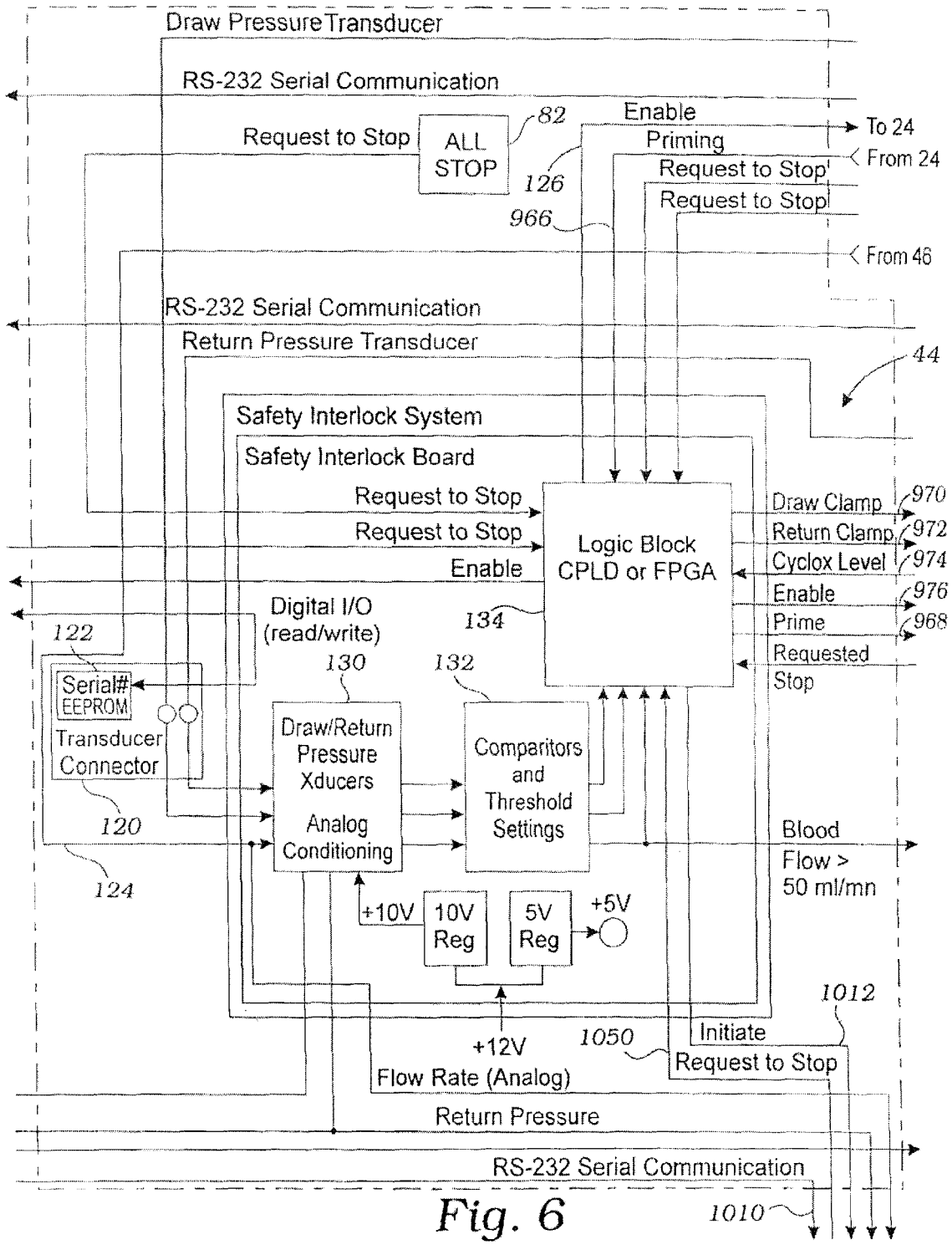
FIG. 6 illustrates an interlock system used in the system of FIG. 1.

A host/user interface 66 of the system 10 monitors both the pressure on the draw tube 34 via a draw pressure sensor 68 and the pressure on the return tube 50 via a return pressure sensor 70. As illustrated in FIG. 6, the ends of the draw tube 34 and the return tube 50 that couple to the oxygenation device 54 are embodied in a Y-connector 71 in this example. The Y-connector 71 includes the draw pressure sensor 68 and the return pressure sensor 70, which are operatively coupled to the host/user interface 66 via an electrical connector 73. The host/user interface 66 may deliver these pressure readings to the display 32 so that a user can monitor the pressures and adjust them if desired. The host/user interface 66 also receives a signal from a level sensor 72 that monitors the level of fluid within the mixing chamber 64 of the oxygenation device 54 to ensure that the oxygen-supersaturated physiological solution is mixing with the patient's blood with little or no bubble formation.

The system 10 further advantageously includes a suitable bubble detector 74. The bubble detector 74 includes a suitable bubble sensor 76 positioned at the return tube 50 to detect bubbles as they pass through the return tube 50 to the patient 38. Again, as discussed in greater detail below, the bubble detector 74 receives the signals from the bubble sensor 76 and processes information regarding the nature of any bubbles that may be traveling in the oxygen-enriched blood going back to the patient 38. In this embodiment, the bubble detector 74 provides this information to the host/user interface 66 so that information regarding bubbles in the effluent may be provided to the user via the display 32. The bubble detector 74 may also control or shut down the system 10 in certain circumstances as discussed in detail below.

The system 10 also includes an interlock system 44. The interlock system 44 communicates with many of the components of the system 10 for various reasons. The interlock system 44 monitors the various components to ensure that the system 10 is operating within certain prescribed bounds. For example, the interlock system 44 receives information regarding draw and return pressures from the pressure sensors 68 and 70, information regarding fluid level in the mixing chamber 64 from the level sensor 72, and information regarding the number and/or size of bubbles from the bubble detector 74, as well as other information regarding the operating states of the various components. Based on this information, the interlock system 44 can shut down the system 10 should it begin to operate outside of the prescribed bounds. For example, the interlock system 44 can engage clamps 78 and 80 on the draw tube 34 and the return tube 50, respectively, as well as disable the blood pump system 24 and the system controller 55 that controls the oxygenation device 54. While the interlock system 44 typically operates in this automatic fashion, a safety switch 82 may be provided so that a user can initiate a shutdown of the system 10 in the same fashion even if the system 10 is operating within its prescribed bounds.

The system 10 has a low priming volume relative to conventional extracorporeal circuits, typically in the range of 25 to 100 milliliters. Thus, a heater typically is not used with the system 10. However, if it is desirable to control the temperature of the incoming blood in the draw tube 34 or the outgoing gas-enriched blood in the return tube 50, an appropriate device, such as a heat exchanger, may be operatively coupled to one or both of the tubes 34 and 50. Indeed, not only may the heat exchanger (not shown) be used to warm the fluid as it travels through the system 10, it may also be used to cool the fluid. It may be desirable to cool the fluid because moderate hypothermia, around 30° C. to 34° C. has been shown to slow ischemic injury in myocardial infarction, for example.

Host/User Interface

Figure 3:
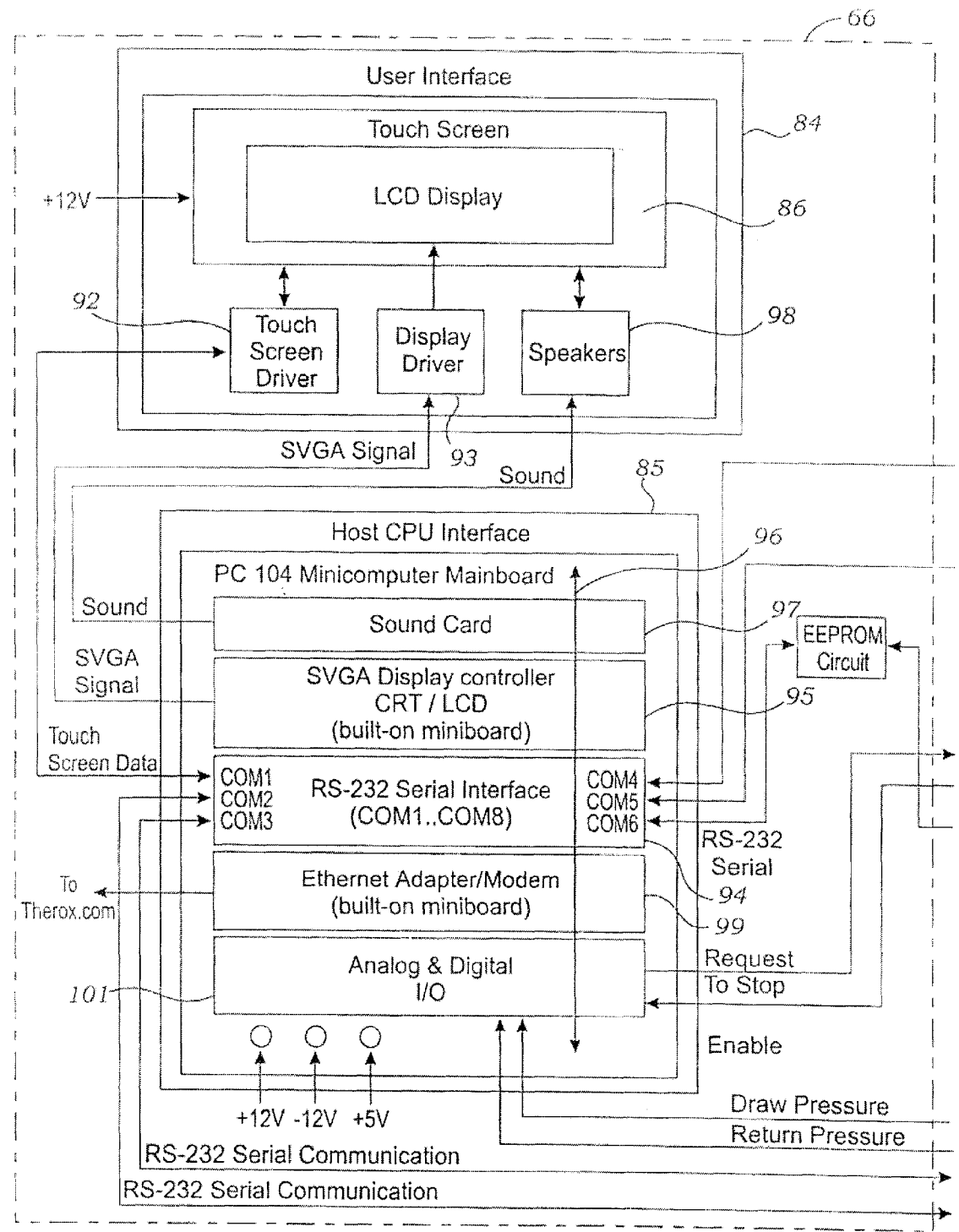
FIG. 3 illustrates a block diagram of the host/user interface used in the system of FIG. 1.
Figure 4:
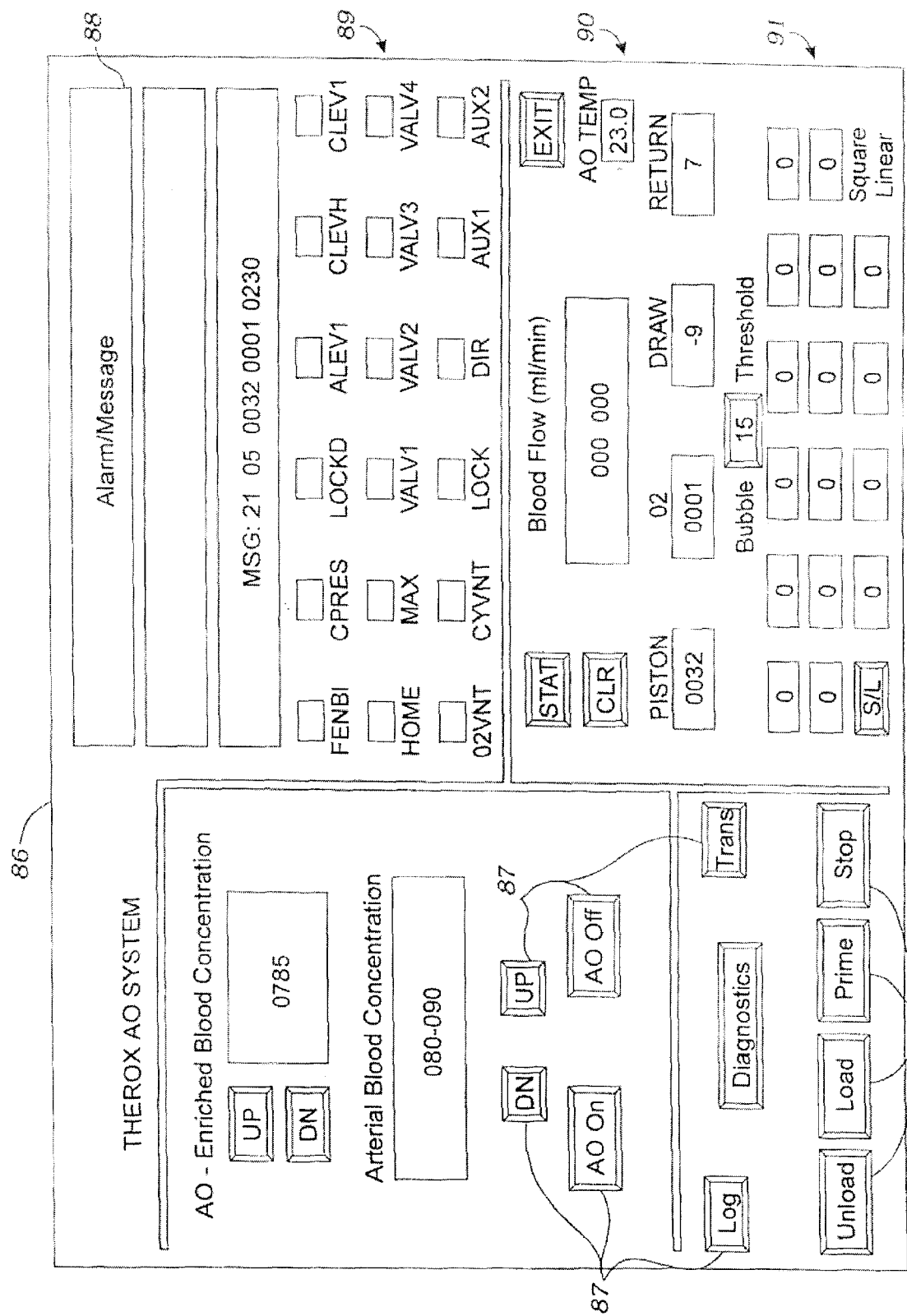
FIG. 4 illustrates an exemplary display.

The various details of the system 10 described above with reference to FIGS. 1 and 2 will be described with reference to the remaining Figs. Turning now to FIG. 3, an exemplary embodiment of the host/user interface 66 is illustrated. The host/user interface 66 includes a user interface 84 and a host interface 85. The user interface 84 may include a user input and display device, such as a touch screen display 86. As illustrated in FIG. 4, the touch screen display 86 may include "buttons" 87 that initiate certain operations when a user touches them. The touch screen display 86 may also include information such as alarms/messages 88, status indicators 89, blood flow information 90, and bubble count 91.

The user inputs are handled by a touch screen driver 92, and the displayed information is handled by a display driver 93. The touch screen driver 92 transmits user inputs to an interface, such as an RS-232 interface 94. The RS-232 interface 94 may communicate these user inputs to other portions of the system 10, such as the system controller 55, the interlock system 44, the blood pump system 24, and the bubble detector 74. The display driver 93 communicates with a display controller 95, which is also coupled to the RS-232 interface 94 via a bus 96. The display controller 95 receives updated information from the various other portions of the system 10, and it uses this information to update the display 86.

The host interface 85 may also include various other capabilities. For example, the host interface 85 may include a sound card 97 to drive speakers 98 on the user interface 84. In addition, a network adapter 99 may allow the host interface 85 to communicate with an external network, such as a LAN in the hospital or a remote network for providing updates for the system 10, e.g., the Internet. Finally, the host interface 85 may include an analog and/or digital I/O device 101, which in this example transmits and receives certain signals such as an enable signal, a "request to stop" signal, a draw pressure signal, and a return pressure signal.

Blood Pump System and Interlock System

Figure 5:
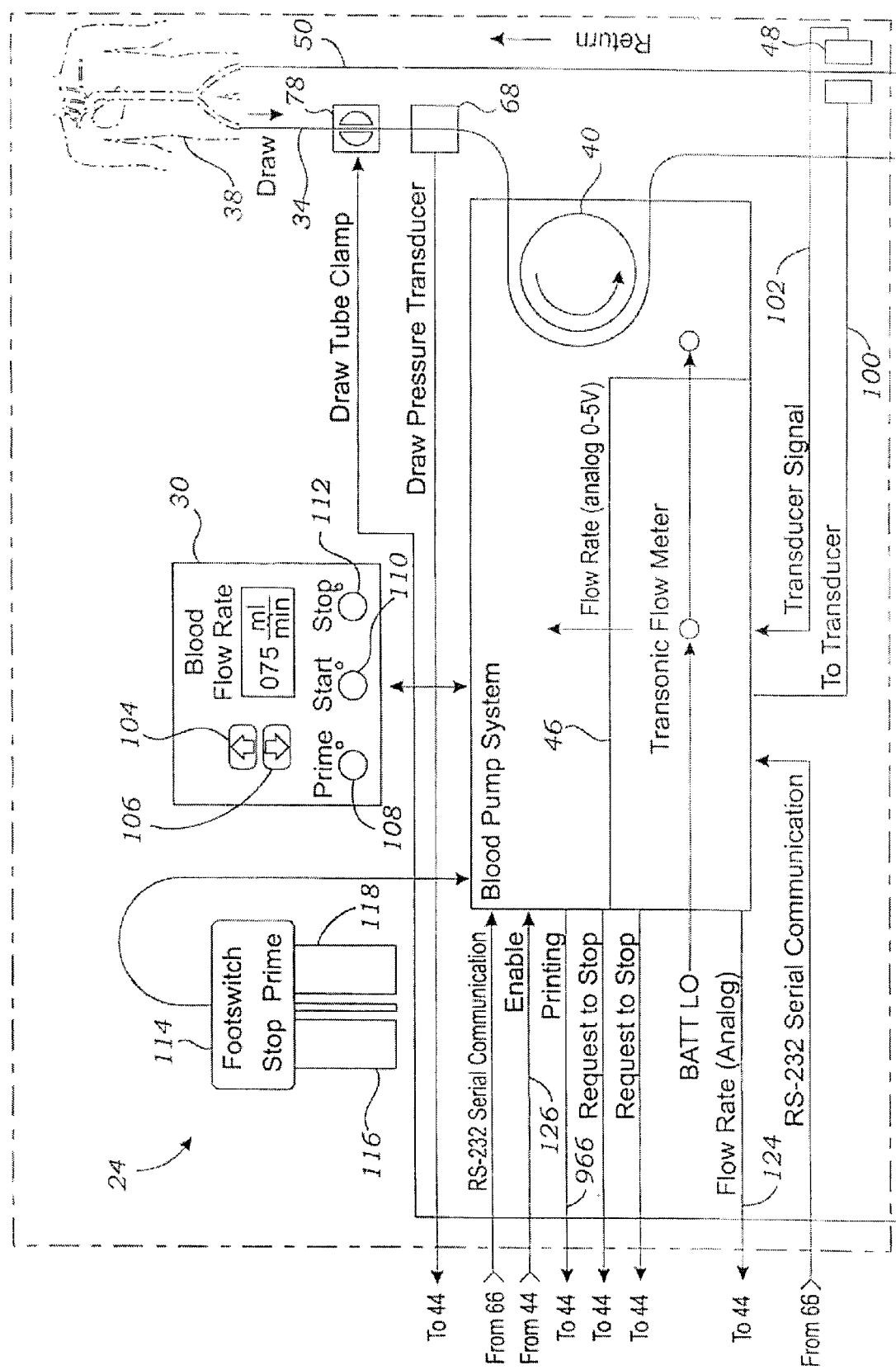
FIG. 5 illustrates a block diagram of a blood pump system used in the system of FIG. 1.

Many of the components described below, while particularly useful in the exemplary system 10, may be quite useful in other types of systems as well. For example, the blood pump system 24 described in detail with reference to FIG. 5 may be used not only in the context of the system 10, but also in other types of perfusion systems, such as conventional heart-lung machines and other types of other extracorporeal circuits. As previously discussed, the blood pump system 24 utilizes a suitable pump 40, such as a peristaltic pump, to draw blood from the patient 38 through a draw tube 34. The blood pump system 24 further includes a flow meter 46, such as a transonic flow meter, which communicates with a flow transducer 48 via lines 100 and 102. The feedback from the transducer 48 enables the blood pump system 24 to maintain the desired flow rate. The desired flow rate may be entered by a user, such as perfusionist or a nurse, via the control panel 30. In this example, the control panel 30 includes an indication of the current blood flow rate in milliliters per minute, as well as an "up" button 104 and a "down" button 106 that permit a user to adjust the blood flow rate upwardly and downwardly, respectively. The control panel 30 further includes a "prime" button 108, a "start" button 110, and a "stop" button 112. In addition, the control panel 30 may be augmented by a foot switch 114, which includes a stop pedal 116, which performs the same function as the stop button 112, and a prime start pedal 118, which performs the same function as the prime button 108 and the start button 110.

Because the blood pump system 24 utilizes feedback from the flow transducer 48 to maintain and adjust the r.p.m. of the pump 40 in a manner which provides a consistent flow rate, the blood pump system 24 requires no user interaction once the system has been primed and the flow rate has been set. Therefore, unlike blood pumps used in other extracorporeal circuits, the blood pump system 24 may be operated by a semi-skilled technician or nurse, rather than a highly skilled perfusionist.

To provide an extra measure of confidence with such semi-skilled operation, the blood pump system 24 takes advantage of certain features provided by the interlock system 44. For example, referring to the interlock system 44 illustrated in FIG. 6 as well, the interlock system 44 may include or have access to a personality module 120. The personality module 120 may include a memory 122, such as a read only memory for example. The memory 122 of the personality module 120 may include various information, such as flow rates and ranges, as well as other information to be discussed below. Therefore, for a particular patient or for a particular type of patient, the desired flow rate and/or the desired flow rate range may be programmed into the memory 122. For example, in acute myocardial infarction applications, the flow rate may be 75 milliliters per minute, or for stroke applications the flow rate may be 300 milliliters per minute. In this exemplary embodiment, the personality module 120 may be located in the Y-connector 71. Because the information programmed into the personality module 120 may be related to a particular patient or a particular type of patient, and because a new Y-connector 71 is typically used with each patient, the location of the personality module 120 in the Y-connector 71 provides an effective method of customizing the system 10 with each patient treated.

The interlock system 44 reads this flow information from the memory 122 and compares it to the flow rate delivered by the flow meter 46 on line 124. As long as the flow rate from the flow meter 46 is maintained at the desired flow rate or within the desired flow range programmed into the memory 122, the interlock system 44 will continue to supply an enable signal on line 126 to the blood pump system 24. However, should the flow rate fall outside of the desired range, due to operator intervention, failure of the flow transducer 48, etc., the interlock system 44 will switch the signal on the line 126 to disable the blood pump system 24. The interlock system 44 will further actuate the clamps 78 and 80 in order to shut down the system 10 in a manner safe for the patient 38.

The interlock system 44 includes an analog conditioning circuit 130 that receives and conditions the analog flow rate signal from the flow meter 46 on the line 124. This conditioned signal is compared with the information from the memory 122 using comparators and threshold settings 132. The results of this comparison are delivered to a logic block 134, which may be, for example, a field programmable gate array (FPGA) or a complex programmable logic device (CPLD). The logic block 134 generates the enable or disable signal on the line 126.

The conditioning circuit 130 also receives the analog pressure signals from the draw pressure transducer 68 and the return pressure transducer 70. These pressures may be monitored to ensure that neither the draw tube 34 nor the return tube 50 are kinked or otherwise unable to deliver fluid at a minimum desired pressure or higher. The logic block 134 compares these pressures to the minimum pressure setting, e.g., −300 mm Hg, and delivers a warning signal if either pressure drops below the minimum pressure setting. In addition, the draw pressure is monitored to ensure that it remains higher than a minimal draw pressure threshold, e.g. −300 mm Hg, to ensure that bubbles are not pulled out of solution by the blood pump 40. Still further, the return pressure is monitored to ensure that it does not exceed a maximum return pressure, e.g. 2000 mm Hg.

The manner in which the interlock system 44 interfaces with various other portions of the system 10 will be discussed below where appropriate. However, it can be seen that the blood pump system 24 and the interlock system 44 provide a technique by which blood may be removed from a patient at a desired and maintainable flow rate and that any deviation from the desired flow rate will cause the system to shut down in a manner which is safe for the patient 38. Accordingly, the use of a perfusionist may be obviated in most circumstances.

Oxygenation Device

Although the blood pump system 24 may be used in a variety of different systems, for the primary purpose of this discussion it is incorporated within the system 10. As described in reference to FIG. 2 above, one of its main purposes is to deliver blood to the oxygenation device 54. Accordingly, before discussing the blood pump system 24 or the other components further, an understanding of the manner in which the oxygenation device 54 functions is appropriate.

Figure 8:
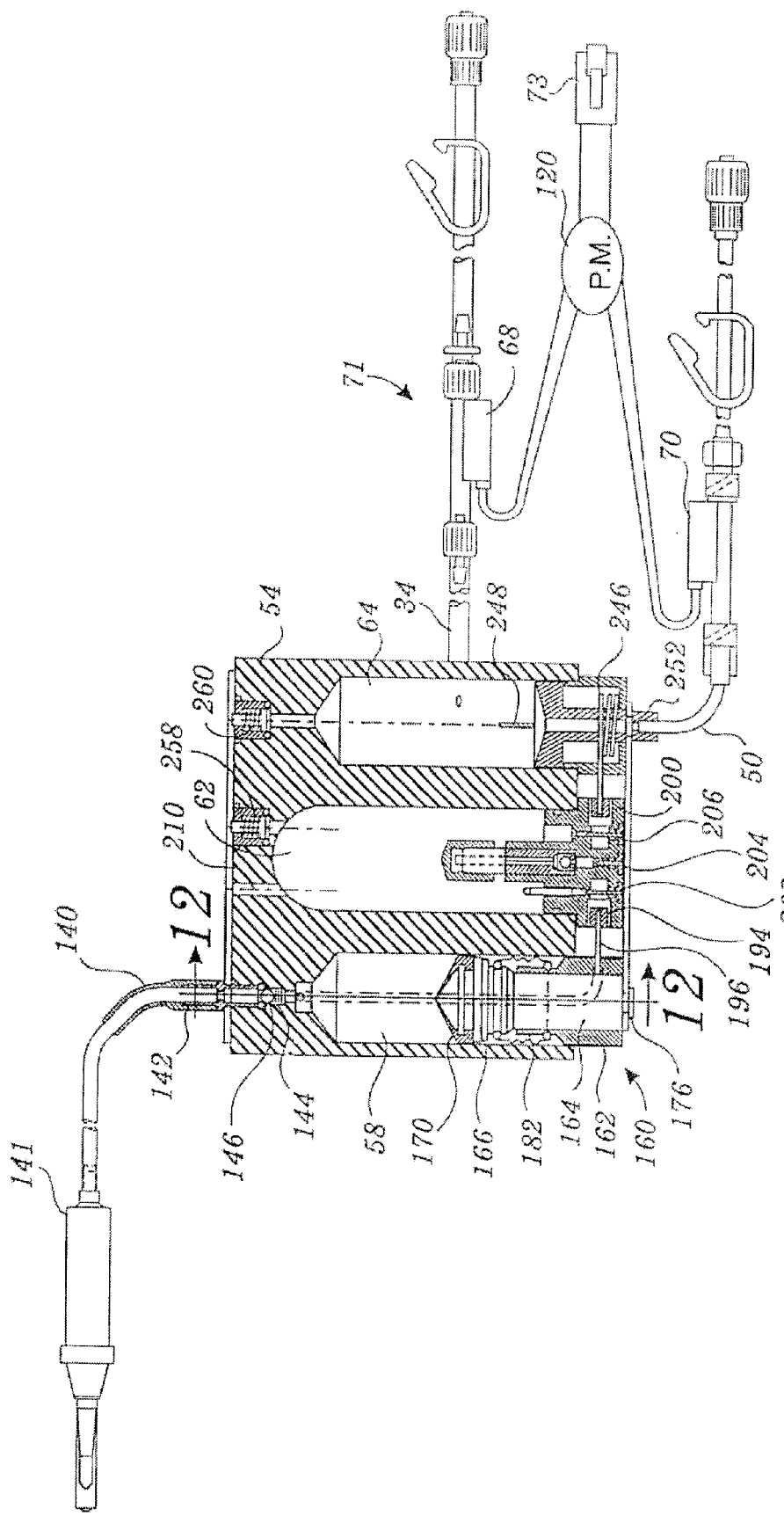
FIG. 8 illustrates a cross-sectional view taken along line 8—8 in FIG. 7.

Referring first to FIGS. 7, 8, and 9, an exemplary embodiment of an oxygenation device 54 is illustrated. As mentioned previously, the oxygenation device 54 includes three chambers: a fluid supply chamber 58, an atomization chamber 62, and a mixing chamber 64. Generally speaking, physiologic fluid, such as saline, is drawn into the fluid supply chamber 58. The physiologic fluid is transferred under pressure from the fluid supply chamber 58 to the atomization chamber 62. In the atomization chamber 62, the physiologic fluid is enriched with a gas, such as oxygen, to form a gas-enriched physiologic fluid. For example, the physiologic fluid may be supersaturated with the gas. The gas-enriched physiologic fluid is transferred to the mixing chamber 64 to be combined with a bodily fluid, such as blood. The mixing of the gas-enriched physiologic fluid with the bodily fluid forms a gas-enriched bodily fluid. In one example, blood from a patient is mixed with an oxygen-supersaturated saline solution and transmitted back to the patient.

Beginning with a detailed discussion of the fluid supply chamber 58, an appropriate delivery device, such as a tube 140, is coupled to a supply of physiologic fluid. In this example, the tube 140 may include a drip chamber 141 and is coupled at one end to an IV bag 56. The other end of the tube 140 is coupled to a nozzle 142. The nozzle 142 forms a portion of a fluid passageway 144 that leads to the fluid supply chamber 58. A check valve 146 is disposed in the fluid passageway 144 so that fluid may enter the fluid chamber 58 through the fluid passageway 144, but fluid cannot exit through the fluid passageway 144.

As illustrated by the detailed view of FIG. 10, check valve 146 has an O-ring seal 148 that is disposed between a lip in the fluid passageway 144 and the nozzle 142. A spring 150 biases a ball 152 into contact with the O-ring seal 148. When fluid moving in the direction of the arrow 154 overcomes the force of the spring 150 and the pressure within the fluid supply chamber 58, the ball 152 is pushed against the spring 150 so that fluid may flow into the fluid supply chamber 58. However, fluid cannot flow in the opposite direction because the ball 152 efficiently seals against the O-ring seal 148.

A piston assembly 160 is disposed at the opposite end of the fluid supply chamber 58. The piston assembly 160 includes a sleeve 162 that is fixedly disposed within the fluid supply chamber 58. As illustrated in greater detail in FIG. 11, a plunger 164 is slidably disposed within the sleeve 162. A cap 166 is disposed at one end of the plunger 164. The cap includes a flange 168 that has an outer diameter greater than the inner diameter of the sleeve 162 to limit downward movement of the piston assembly 160. Although the sleeve 162, the plunger 164, and the cap 166 are advantageously made of a relatively rigid material, such as plastic, a relatively resilient end piece 170 is disposed on the cap 166. The end piece 170 advantageously includes sealing members 172 that seal against the interior walls of the fluid supply chamber 58.

Figure 11:
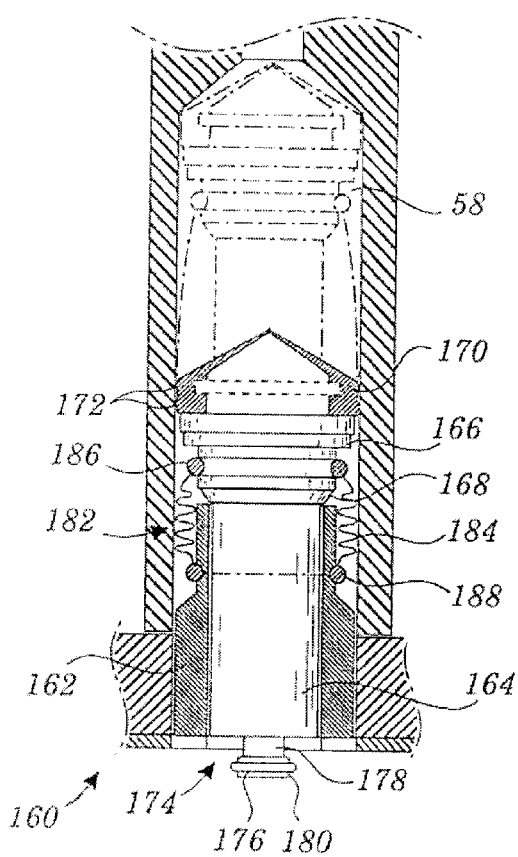
FIG. 11 illustrates a detailed view of a piston assembly illustrated in FIG. 8.
Figure 15:
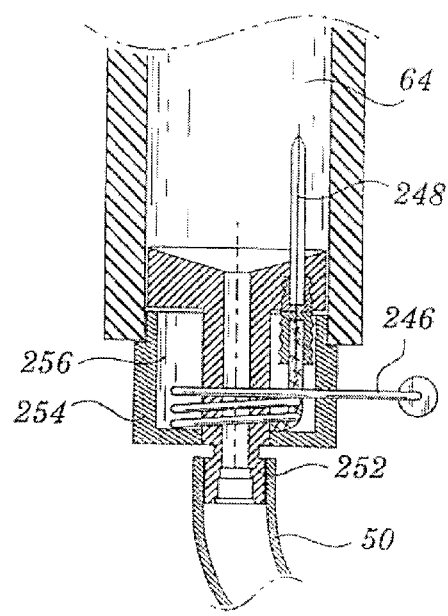
FIG. 15 illustrates a detailed view of a capillary tube illustrated in FIG. 8.
Figure 16:
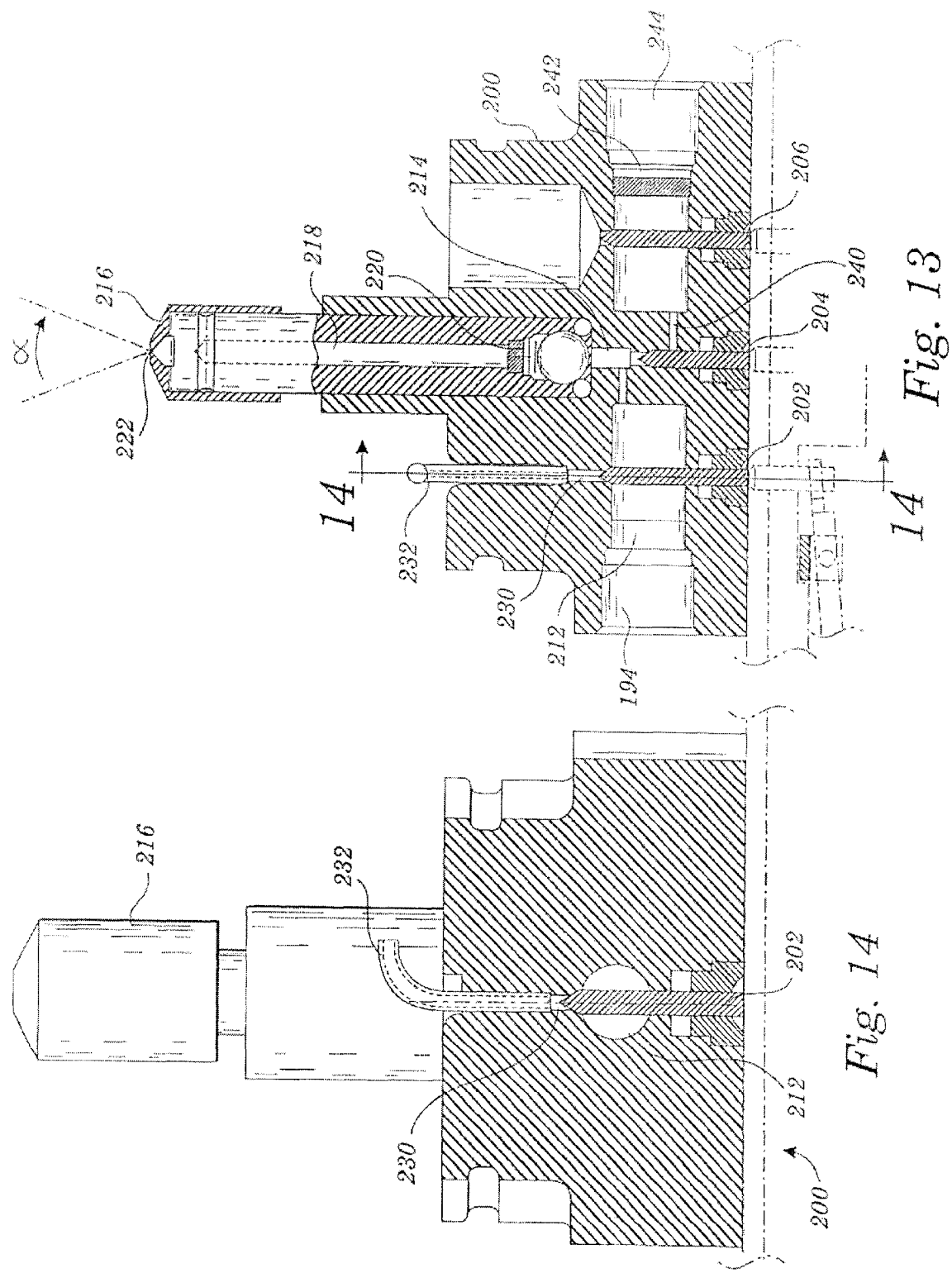
FIG. 16 illustrates a detailed view of a vent valve illustrated in FIG. 8.

As illustrated by the phantom lines in FIG. 11, the piston assembly 160 is moveable between a first position (shown by the solid lines) and a second position (shown by the phantom lines). To facilitate this movement, a device to be described below is coupled to the free end 174 of the piston assembly 160. Although such coupling may occur in various suitable manners, in this example a key 176 is provided at the free end 174 of the piston assembly 160. The key 176 includes a narrow portion 178 and a relatively wider portion 180 so that it somewhat resembles a doorknob, thus allowing a device to latch onto the piston assembly 160 and move it between the first and second positions.

As will be appreciated from a thorough study of this entire discussion, one of the primary advantages of the particular oxygenation device 54 disclosed herein involves its sterility and disposability. The sterility of the piston assembly 160 may be facilitated by providing a sterility sheath 182 disposed between the cap 166 and the sleeve 162. In this embodiment, the sterility sheath 182 includes an extendable tube 184 that is coupled to the cap 166 by a clamp 186 and coupled to the outer portion of the sleeve 162 by a clamp 188. The expandable tube 184 may take various forms, such as a plastic tube that folds in an accordion-like manner when the piston assembly 160 is in its retracted position (as shown by the solid lines). However, the expandable tube 184 may take various other forms, such as a flexible member that stretches between the retracted position and the extended position of the piston assembly 160. The clamps 186 and 188 may also take various suitable forms, such as rubber O-rings in this example.

Referring additionally to FIG. 12, the fluid supply chamber 58 further includes a second fluid passageway 190. As illustrated by way of a specific example in the present embodiment, the fluid passageway 190 is coupled to a fluid passageway 194 by a tube 196. The passageway 194 is an inlet to a valve assembly 200 that controls the manner in which fluid from the fluid supply chamber 58 is delivered into the atomization chamber 62.

In operation, the piston assembly 160 within the fluid supply chamber 58 acts as a piston pump. As the piston assembly 160 retracts, fluid is drawn into the chamber 58 from the fluid supply 56. No fluid can be drawn from passageway 190 because valve assembly 200 is closed and a check valve 192 is closed in this direction. As the piston assembly 160 extends, the fluid within the chamber 58 is pressurized, typically to about 670 psi, and expelled from the fluid supply chamber 58 through the fluid passageway 190. The outlet of the fluid supply chamber 58 is coupled to an inlet of the atomization chamber 62 via an appropriate fluid passageway.

Detailed views of the valve assembly 200 are illustrated in FIGS. 13 and 14. The valve assembly 200 includes three valves: a fill valve 202, a flush valve 204, and a flow valve 206. While any suitable valve arrangement and type of valve may be used, in this embodiment the valves 202, 204, and 206 are needle valves that are normally biased in the closed position as shown. When the pressure within the atomization chamber 62 rises above a certain level, such as about 100 psi, the valves 202, 204, and 206 will move from the closed position to the opened position, assuming that they are allowed to do so. In this embodiment, as will be discussed in greater detail below, push pins and associated actuation mechanisms (as illustrated by the phantom lines in FIG. 13) maintain the valves 202, 204, and 206 in the closed positions until one or more of the valves 202, 204, and 206 is to be opened.

Gas, such as oxygen, is delivered under pressure to the atomization chamber 62 via a passageway 210. For example, the oxygen tank 60 may be coupled to the inlet of the passageway 210 to provide the desired oxygen supply. If all of the valves 202, 204, and 206 are closed, fluid flows from the inlet passageway 194 into a passageway 212 in which the fill valve 202 is located. Because the cross-sectional area of the passageway 212 is larger than the cross-sectional area of the fill valve 202, the fluid flows around the closed fill valve 202 and into a passageway 214 that leads to an atomizer 216.

The atomizer 216 includes a central passageway 218 in which a one-way valve 220 is disposed. In this embodiment, the one-way valve 220 is a check valve similar to that described with reference to FIG. 10. Accordingly, when the fluid pressure overcomes the force of the spring in the one-way valve 220 and overcomes the pressure of the gas within the atomizer chamber 62, the fluid travels through the passageway 218 and is expelled from a nozzle 222 at the end of the atomizer 216.

The nozzle 222 forms fluid droplets into which the oxygen within the atomization chamber 62 diffuses as the droplets travel within the atomization chamber 62. This oxygen-enriched fluid may be referred to herein as aqueous oxygen (AO). In this embodiment, the nozzle 222 forms a droplet cone defined by the angle $\alpha$, which is typically about 20 degrees to about 40 degrees at normal operating pressures, e.g., about 600 psi, within the atomization chamber 62. The nozzle 222 is a simplex-type, swirled pressurized atomizer nozzle including a fluid orifice of about 0.004 inches diameter to 0.005 inches diameter. It should be appreciated that the droplets infused with the oxygen fall into a pool at the bottom of the atomizer chamber 62. Since the atomizer 216 will not atomize properly if the level of the pool rises above the level of the nozzle 222, the level of the pool is controlled to ensure that the atomizer 216 continues to function properly.

The oxygen is dissolved within the atomized fluid to a much greater extent than fluid delivered to the atomizer chamber 62 in a non-atomized form. As previously stated, the atomizing chamber typically operates at a constant pressure of about 600 psi. Operating the atomizer chamber 62 at 600 psi, or any pressure above 200 psi, advantageously promotes finer droplet formation of the physiologic solution from the atomizer 216 and better saturation efficiency of the gas in the physiologic fluid than operation at a pressure below 200 psi. As will be explained shortly, the oxygen-supersaturated fluid formed within the atomizer chamber 62 is delivered to the mixing chamber 64 where it is combined with the blood from the patient 38. Because it is desirable to control the extent to which the patient's blood is enriched with oxygen, and to operate the system 10 at a constant blood flow rate, it may be desirable to dilute the oxygen-supersaturated fluid within the atomizer chamber 62 to reduce its oxygen content. When such dilution is desired, the fill valve 202 is opened to provide a relatively low resistance path for the fluid as compared to the path through the atomizer 216. Accordingly, instead of passing through the atomizer 216, the fluid flows through a passageway 230 which extends upwardly into the atomizer chamber 62 via a tube 232. The tube 232 is advantageously angled somewhat tangentially with respect to the cylindrical wall of the atomizer chamber 62 so that the fluid readily mixes with the oxygen-supersaturated fluid in the pool at the bottom of the atomizer chamber 62.

The valve assembly 200 essentially performs two additional functions. First, with the fill valve 202 and the flow valve 206 closed, the flush valve 204 may be opened so that fluid flows from the inlet passageway 194, through the passageways 212 and 214, and into passageways 240 and 242, the latter of which has a cross-sectional area larger than the cross-sectional area of the flow valve 206. Thus, the fluid flows out of an outlet passageway 244 that is coupled to a capillary tube 246. The capillary tube 246 terminates in a tip 248 that extends upwardly into the mixing chamber 64. Since this fluid has not been gas-enriched, it essentially serves to flush the passageways 242 and 244, and the capillary tube 246 to remove any contaminants and to ensure adequate fluid flow. Second, with the fill valve 202 and the flush valve 204 closed, the flow valve 206 may be opened when it is desired to deliver the gas-supersaturated fluid from the pool at the bottom of the atomizer chamber 62 into the mixing chamber 64.

In this second circumstance, the gas-supersaturated fluid readily flows from the atomization chamber 62 through the capillary tube 246 and into the mixing chamber 64 due to the fact that pressure within the atomization chamber 62 is relatively high, e.g., approximately 600 psi, and pressure within the mixing chamber 64 is relatively low, e.g., about 30 psi. The end of the capillary tip 248 is advantageously positioned below a blood inlet 250 of the mixing chamber 64. This spacial arrangement typically ensures that the blood flowing through the draw tube 34 and into the blood inlet 250 effectively mixes with the oxygen-supersaturated fluid flowing into the mixing chamber 64 through the capillary tip 248. Finally, by the force of the blood pump system 24, the oxygenated blood is pumped out of the mixing chamber 64 through an outlet 252 into the return tube 50.

Typically, the capillary tube 246 and the capillary tip 248 are relatively long to ensure that proper resistance is maintained so that the oxygen within the oxygen-supersaturated fluid remains in solution as it travels from the atomization chamber 62 into the mixing chamber 64. For example, the capillary tube 246 and the tip 248 may be in the range of 50 microns to 300 microns in length and in the range of 3 inches to 20 inches in internal diameter. To maintain the compact size of the oxygenation device 54, therefore, the capillary tube 246 is wrapped about the exit nozzle 252 of the mixing chamber 64, as illustrated in the detailed drawing of FIG. 15. To protect the coiled capillary tube 246 from damage, a protective shield 254 is advantageously formed around the coiled capillary tube 246 to create a compartment 256.

Both the atomization chamber 62 and the mixing chamber 64 include vent valves 258 and 260, respectively. The vent valves 258 and 260, as illustrated in the detail drawing of FIG. 16, are one-way valves that allow gas pressure to be vented out of the oxygenation device 54 and into the atmosphere. In this particular embodiment, the vent valves 258 and 260 include a plunger 262 that is biased in a closed position against an O-ring seal 264 by a spring 266. The biasing force is light so that only one to two psi within the respective chambers 62 or 64 is sufficient to move the plunger 262 away from the seal 264 to vent the chamber. Therefore, as will be discussed in greater detail below, actuation devices that are part of the cartridge enclosure 26 and controlled by the system controller 55 normally maintain the valves 258 and 260 in the closed position.

Before beginning a discussion of the remainder of the system 10, a few points regarding oxygenation of blood in general, and the use of the disclosed oxygenation device 54 in particular, should be noted. First, various methods of oxygenating blood are known or under development. Although an atomizing chamber provides a convenient mechanism for diffusing relatively large amounts of gas into a fluid in a relatively short period of time, it is not the only way of dissolving gas within a fluid. Indeed, other devices, such as membrane oxygenators, gas spargers, bubblers, and thin film oxygenation devices, may be used to perform this function as well. Second, although a piston pump similarly provides a compact and efficient method of pressurizing fluid prior to sending it to an oxygenator, such as the atomizer, other types of pumps or methods of pressurization may be used as well. Third, although a mixing chamber provides a compact environment in which the mixing of the gas-supersaturated fluid with blood may be appropriately monitored and controlled, gas-enriched fluid may be mixed with blood in other ways. For example, gas-supersaturated fluid may be mixed with blood within the mixing zone of a catheter or other suitable device. Therefore, although a piston pump, atomizer, and mixing chamber comprise the oxygenation device 54 utilized in the exemplary embodiment of the system 10, due to certain perceived advantages, other devices can, generally speaking, perform these functions.

With these generalities in mind, the oxygenation device 54 disclosed herein offers several advantages that make it particularly attractive for use within a medical environment. First, the oxygenation device 54 is advantageously made from a clear plastic, such as polycarbonate which can be molded to provide a high strength, low cost device. Second, the oxygenation device 54 is relatively compact, with an exemplary specimen measuring approximately 12 cm in height, 10 cm in width, and 5.5 cm in depth. Thus, it can be utilized within a system 10 that fits easily within an operating room or special procedures lab, regardless of whether the system 10 is fixed or mobile. Third, the oxygenation device 54 combines the preparation of the oxygen-enriched fluid, along with the mixing of the oxygen-enriched fluid with the blood, into a unitary device utilizing only four connections: (1) fluid supply, (2) oxygen supply, (3) blood supply, and (4) blood return. The other connections are part of the oxygenation device 54 itself, and they require no additional connection from the user. Fourth, all of the valves used to operate the oxygenation device 54 are integrated within its unitary structure. Thus, the valves and their associated fluid passageways are protected against external contamination, and users are protected against any contamination that may arise from the use of the various fluids as well. As a result, the oxygenation device 54 is a relatively contamination-free cartridge that may be used during a surgical procedure on a patient, and then removed and replaced prior to performing a surgical procedure on the next patient.

Cartridge Enclosure

Figure 17:
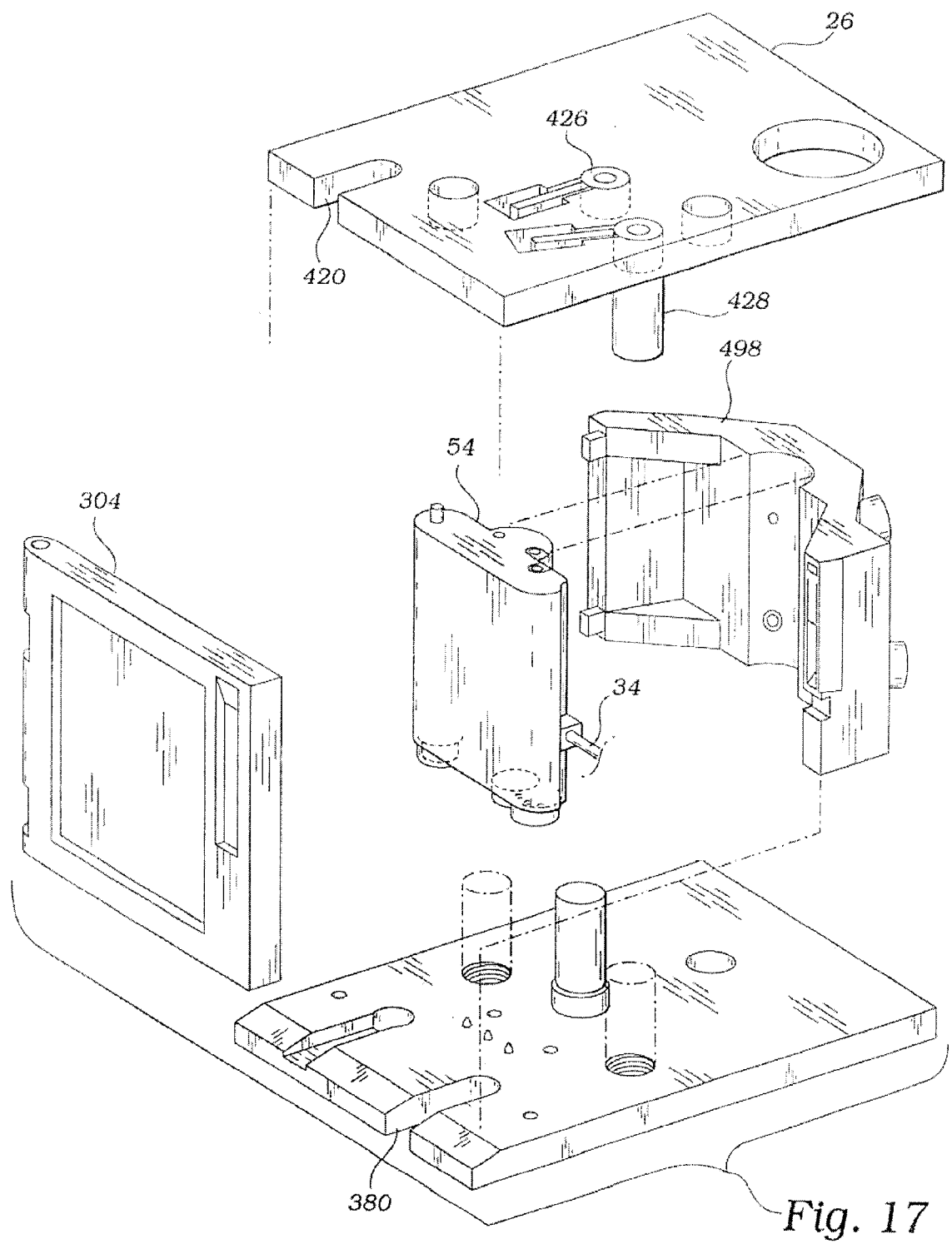
FIG. 17 illustrates an exploded view of the cartridge and cartridge enclosure.
Figure 18:
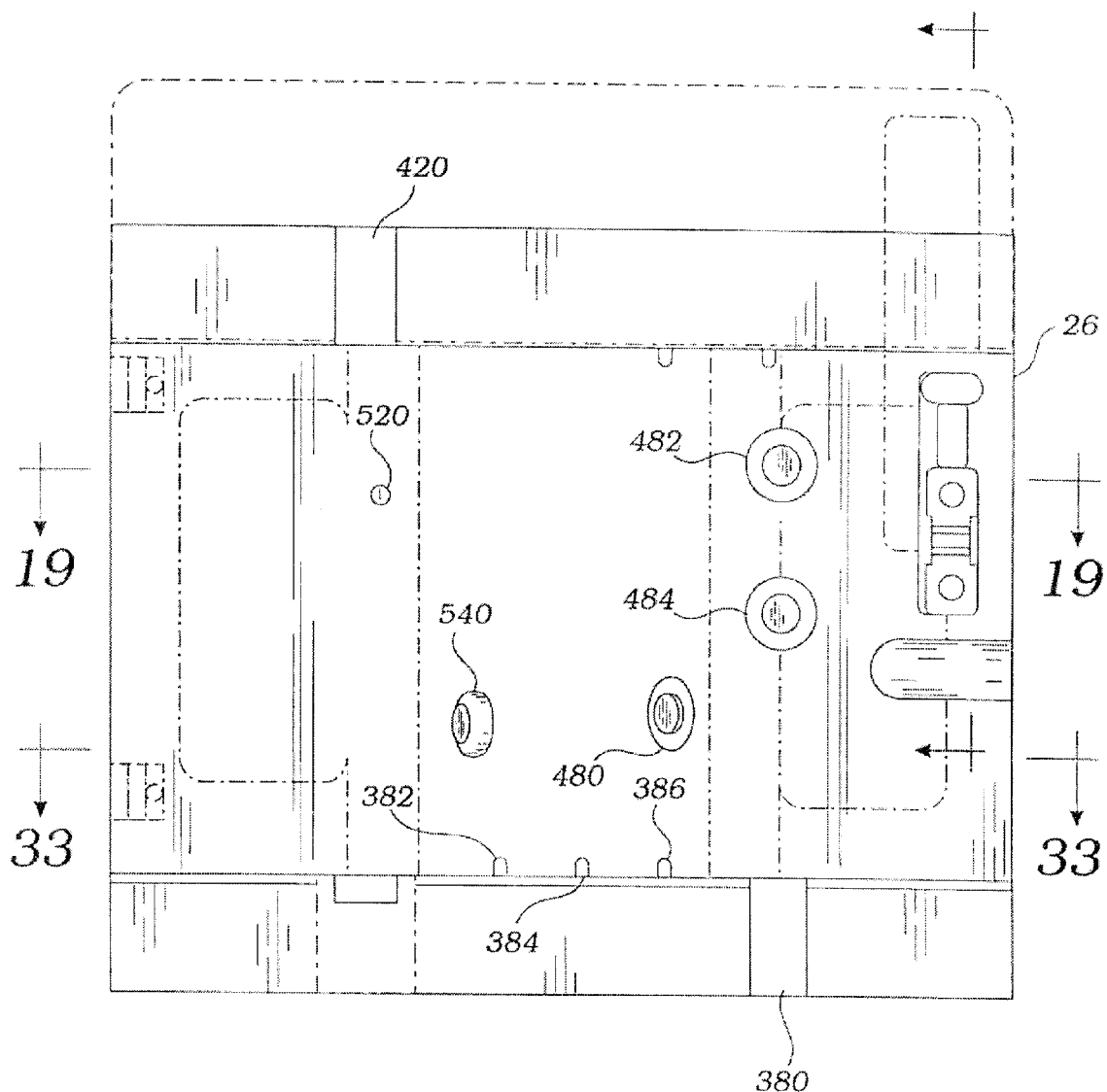
FIG. 18 illustrates a front view of the cartridge receptacle of the cartridge enclosure illustrated in FIG. 1.
Figure 22:
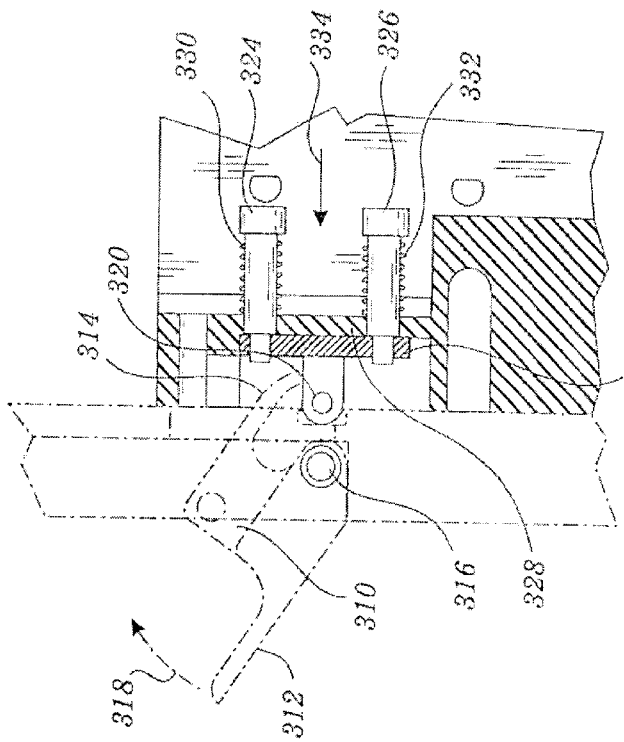
FIG. 22 illustrates another cross-sectional view of the door latch.

Prior to discussing the remainder of the electrical components and the manner in which they control the various mechanical components of the system 10, the manner in which certain mechanical components interface with the oxygenation device 54 will now be discussed. As mentioned previously, the oxygenation device 54 is placed inside of the cartridge enclosure 26. FIG. 17 illustrates an exploded view of the cartridge enclosure 26, and FIG. 18 illustrates a front view of the cartridge enclosure 26. In this embodiment, the cartridge enclosure 26 includes a cartridge receptacle 302 that is accessed by a hinged door 304. When the oxygenation device 54 is placed within the cartridge receptacle 302, the door 304 is closed and latched for various reasons. First, the cartridge receptacle 302 and the oxygenation device 54 are sized and shaped in a complementary fashion so that the various surfaces, vents, valves, etc. are positioned in a desired manner. When the door 304 is closed and latched, an inner surface 306 of the door 304 advantageously presses against a surface 308 of the oxygenation device 54 to ensure that the positioning of the oxygenation device 54 is accurate. Second, the door 304 is advantageously locked to prevent removal of the oxygenation device 54 during normal operation of the system 10. Accordingly, the door 304 is provided with a latch 310. Referring to FIGS. 19–26, the door latch 310 includes a handle portion 312 and a latching portion 314.

To latch the door 304, a user grasps the handle portion 312 to pivot the latch 310 about a pivot pin 316 generally in the direction of the arrow 318. As the latch 310 pivots in the direction of the arrow 318, the latching portion 314 hooks around a latch pin 320. The latch pin 320 is coupled to a biasing mechanism 322. The biasing mechanism 322, in this embodiment, includes two pins 324 and 326 that extend through holes in a wall 328. A respective spring 330 and 332 is disposed about each pin 324 and 326 to bias the latch pin 320 toward the wall 328. As the latching portion 314 hooks around the latch pin 320, the latch 310 may tend to overcome the bias of the springs 330 and 332 to move the latching mechanism 322 slightly in the direction of the arrow 334. However, due to the bias of the latching mechanism 322, it tends to hold the latch 310, and thus the door 304, tightly in place.

To keep the latch 310 in place, and thus lock the door 304, a locking mechanism 340 is provided. In this embodiment, the locking mechanism includes 340 a slidable pin 342 that is disposed in a portion of the wall 328. As the latch 310 moves in the direction of the arrow 318, it eventually contacts the front end of the pin 342, and thus moves it in the direction of the arrow 344. The rear portion of the pin 342 is coupled to a piston 346 of a pull-type solenoid 348. The piston 346 is biased outwardly by a spring 350, so that the piston 346 is normally in an extended position.

The latch 310 is configured so that as it reaches its latched position, the spring 350 pushes the pin 342 in the direction of the arrow 352 so that the pin 342 extends over a portion 354 of the latch 310. With the pin 342 in its locked position over the portion 354 of the latch 310, the latching portion 314 cannot be removed from the latching mechanism 322. Instead, the latch 310 remains locked until the piston 346 of the solenoid 348 is retracted to move the pin 342 out of the way of the latch 310.

It should also be noted that the latch 310 includes a sensor 360 that provides an electrical signal indicative of whether the latch 310 is in its locked position. In this embodiment, the sensor 360 is a Hall effect sensor. The latch 310 includes a magnet 362 that is positioned to align with the sensor 360 when the latch 310 is in the locked position. When the magnet 362 is aligned with the sensor 360, the electromagnetic signal is uninterrupted. However, until the magnet 362 reaches alignment, the electromagnetic signal from the sensor 360 is interrupted, thus indicating that the latch 310 is not yet in its locked position.

Valve Actuation

As mentioned previously, in the present embodiment, the size and shape of the oxygenation device 54, the contour of the cartridge receptacle 302, and the closing of the door 304 ensure that the oxygenation device 54 is positioned in a desired manner within the cartridge enclosure 26. Correct positioning is of concern due to the placement of the valves and vents of the oxygenation device 54 and the manner in which they are controlled and actuated. As mentioned earlier, the valves and vents of the oxygenation device 54 are actuated using pins in this embodiment. The top of the oxygenation device 54 includes vents 258 and 260, and the bottom of the oxygenation device 54 includes three valves, 202, 204, and 206. In this embodiment, these vents 258 and 260 and valves 202, 204 and 206 are electromechanically actuated using solenoid-actuated pins.

A detailed view of these actuation devices is illustrated in FIGS. 27–32. Referring first to FIG. 27, a bottom view of the cartridge enclosure 26 is illustrated. The oxygenation device 54 is illustrated by phantom lines. It should be noted that the bottom portion of the cartridge enclosure 26 advantageously includes a slot 380 through which the blood return tube 50 of the oxygenation device 54 may pass. Once the oxygenation device 54 is in place within the cartridge enclosure 26, the fill valve 202, the flush valve 204, and the flow valve 206 should be in alignment with respective actuation pins 382, 384, and 386. Advantageously, each of the pins 382, 384, and 386 is tapered at the end to provide an increased tolerance for misalignment. Each of the actuation pins 382, 384, and 386 is moved between a closed position and an open position by a respective solenoid 388, 390, and 392. Each of the solenoids 388, 390, and 392 is coupled to its respective actuation pin 382, 384, and 386 via a respective lever 394, 396, and 398. Each of the respective levers 394, 396, and 398 pivots on a respective fulcrum or pivot pin 400, 402, and 404.

The manner in which the actuators operate may be understood with reference to FIGS. 28 and 29. While these figures only illustrate the actuator for the flush valve 204, it should be understood that the other actuators operate the fill valve 202 and the flow valve 206 in the same manner. As mentioned previously, the valves 202, 204, and 206 are normally held in a closed position. Accordingly, in this particular embodiment, the solenoids 388, 390, and 392 are pull-type solenoids. As illustrated in FIG. 28, a piston 406 of the pull-type solenoid 390 is urged into an extended position by a spring 408 that biases one end of the lever 396 generally in the direction of the arrow 410. As a result, the spring 408 also biases the actuation pin 384 generally in the direction of the arrow 412 to maintain the flush valve 204 in its closed position.

To allow the flush valve 204 to open, the solenoid 390 is actuated as illustrated in FIG. 29. The actuation of the pull-type solenoid 390 moves the piston 406 generally in the direction of the arrow 414 into a retracted position. The force of the solenoid 390 overcomes the bias of the spring 408 and moves the actuation pin 384 generally in the direction of the arrow 416. With the actuation pin 384 in a retracted position, the flush valve 204 may open by moving in the direction of the arrow 416.

The actuation of the vent valves 258 and 260 takes place in a similar fashion. Referring now to FIG. 30, a top view of the cartridge enclosure 26 is illustrated. The top portion of the cartridge enclosure 26 also includes a slot 420 through which the IV tube 140 may pass. Once the oxygenation device 54 is properly positioned within the cartridge enclosure 26, the vent valves 258 and 260 align with actuation pins 422 and 424, respectively. The pins 422 and 424 are also advantageously tapered at the ends to increase tolerance to misalignment. Each of the actuation pins 422 and 424 is actuated by a respective solenoid 426 and 428. Each of the solenoids 426 and 428 is coupled to the respective actuation pin 422 and 424 by a respective lever 430 and 432. Each of the levers 430 and 432 pivots about a fulcrum or pivot pin 434 and 436, respectively.

As described with reference to FIGS. 31 and 32, the operation of the actuators for the valves 258 and 260 is similar to the operation of the actuators for the valves 202, 204, and 206. Although FIGS. 31 and 32 illustrate only the actuator for the vent valve 260, it should be understood that the actuator for the vent valve 258 operates in a similar manner. Referring first to FIG. 31, the solenoid 428 in this embodiment is a pull-type solenoid. A spring 440 generally biases the lever arm 432 in the direction of the arrow 442 to move a piston 444 of the solenoid 428 into an extended position. Accordingly, by virtue of the action of the lever 432 about the pivot pin 436, the spring 440 moves the actuation pin 424 into an extended position. In the extended position, the actuation pin 424 exerts pressure on the vent valve 260 (not shown) to maintain the vent valve 260 in a closed position.

To open the vent valves 258 and 260, the solenoids 426 and 428 are actuated. As illustrated in FIG. 32, when the pull-type solenoid 428 is actuated, the piston 444 moves into a retracted position generally in the direction of the arrow 446. The force of the solenoid 428 overcomes the biasing force of the spring 440 and, thus, the lever 432 moves the actuation pin 424 generally in the direction of the arrow 448 into a retracted position. When the actuation pin 424 is in the retracted position, the vent valve 260 may move upwardly to open and vent gas within the mixing chamber 64.

Cartridge Sensors

Referring again to FIG. 18, a study of the cartridge receptacle 302 reveals that a number of sensors are utilized to monitor and/or control the system 10 in general and the oxygenation device 54 in particular. Due to the nature of the information to be gathered and the types of sensors used to gather this information, the oxygenation device 54 and the sensors include certain features that facilitate the gathering of such information in a more accurate and robust manner. However, it should be appreciated that other types of sensors and/or features may be utilized to gather similarly relevant information for use in monitoring and/or controlling the system 10 and oxygenation device 54.

As will be appreciated from a detailed discussion of the electronic controls of the system 10, it is desirable to monitor and control fluid levels within the atomization chamber 62 and the mixing chamber 64. Accordingly, an AO level sensor 480 is provided to monitor the level of aqueous oxygen within the atomizer chamber 62, and a high level sensor 482 and a low level sensor 484 are provided to monitor the level of the oxygen-enriched blood within the mixing chamber 64. As mentioned above, because the oxygenation device 54 is configured as a replaceable cartridge in this exemplary embodiment, the sensors have been placed within the cartridge enclosure 26 instead of within the oxygenation device 54. Thus, the level sensors 480, 482, and 484 do not actually contact the fluid within the chambers 62 and 64. Were the sensors 480, 482, and 484 to contact the liquid, they could become contaminated and, thus, the sensors would typically be replaced each time the system 10 was used for a different patient. Since this would likely add to the cost of replacement items, and potentially affect the sterility of the system, from both a user's standpoint and a patient's standpoint, it is desirable that the sensors do not contact the liquid within the oxygenation device 54.

In this embodiment, the sensors 480, 482, and 484 are ultrasonic sensors. Because ultrasonic waves travel more efficiently through solids and liquids than through air, it is desirable that the sensors 480, 482, and 484 and/or the oxygenation device 54 be configured in a manner which promotes the efficient transmission and reception of ultrasonic waves. In this embodiment, both the sensors 480, 482, and 484 and the oxygenation device 54 include features which prove advantageous in this regard.

Figure 33:
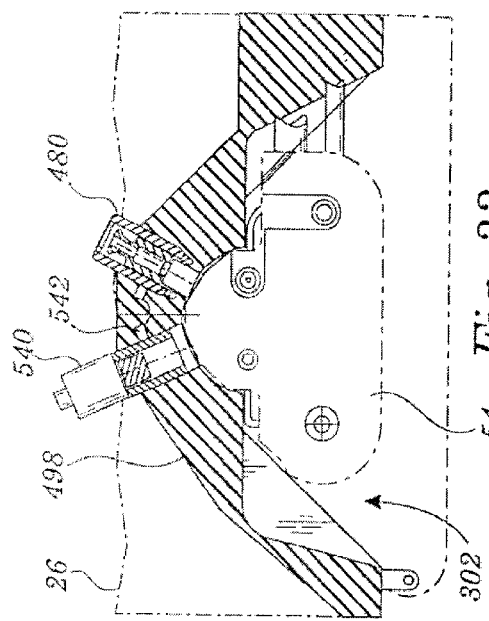
FIG. 33 illustrates a cross-sectional view of the cartridge enclosure taken along line 33—33 in FIG. 18.
Figure 35:
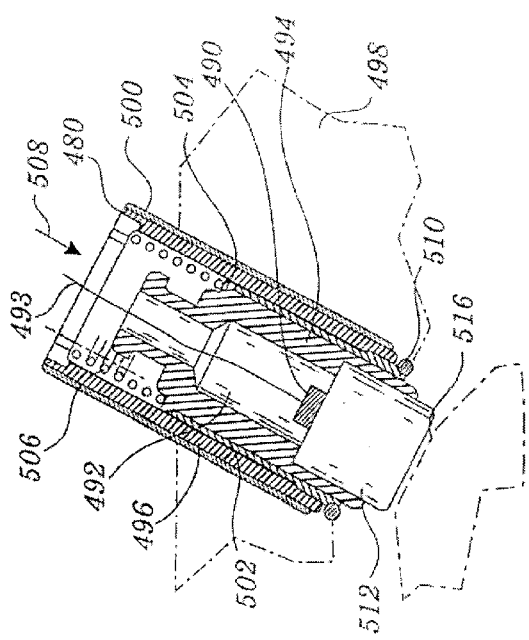
FIG. 35 illustrates a detailed view of an ultrasonic sensor illustrated in FIG. 33.

FIGS. 19 and 33 are cross-sectional views of the cartridge enclosure 26 that illustrate the high level sensor 482 and the AO level sensor 480, respectively. Although the low level sensor 484 is not illustrated in cross-section, it should be understood that its construction is similar to or identical to the construction of the sensors 480 and 482. Furthermore, detailed views of the sensors 482 and 480 are illustrated in FIGS. 34 and 35, respectively, again with the understanding that the sensors 480, 482, and 484 are substantially identical in regard to the details shown in these Figs.

To ensure that physical contact is maintained between the oxygenation device 54 and the sensors 480, 482, and 484, the sensors are advantageously biased into contact with the oxygenation device 54. The sensors 480, 482, and 484 actually utilize a spring-biasing technique, although various other types of biasing techniques may be utilized to achieve similar results. In this example, an ultrasonic transducer element 490 is disposed within a channel 492 formed within a sensor body 494. The sensor body 494 may be formed in any suitable shape, but it is illustrated in this embodiment as being cylindrical. The sensor body 494 is slidably disposed within a sleeve 496. The sleeve 496 is fixedly disposed in a wall 498 of the cartridge enclosure 26. For example, the sleeve 496 may have external screw threads 500 so that the sleeve 496 may be screwed into a threaded bore in the wall 498. To facilitate slidable movement of the sensor body 494 within the sleeve 496, a bushing 502 may be provided within the sleeve 496. In this example, the sensor body 494 includes an annular flange 504 that abuts against one end of the bushing 502 in order to limit outward movement of the sensor body 494. A spring 506 is disposed in the rear portion of the sleeve 496. The spring 506 abuts against the opposite side of the annular flange 504 to bias the sensor body 494 generally in the direction of the arrow 508. The bushing 502 may be adhered to, or an integral part of, the sleeve 496, or it may be held in place by an external seal or cap 510.

Although the spring-loaded construction of the sensors 480, 482, and 484 tends to bias the sensors into contact with the oxygenation device 54 to facilitate the efficient transmission of ultrasonic energy, the nature of the contact between the end of the sensor and the oxygenation device 54 is also important for efficient ultrasonic wave transmission. Hence, to improve this contact region, the sensors 480, 482, and 484 include a resilient member 512, such as a rubber cap. The resilient member 512 is able to deform slightly as it contacts the oxygenation device 54 to ensure that a good contact is made. To enhance the contact region further, the oxygenation device 54 advantageously includes flat contact portions 514 and 516, respectively, so that the contour of the oxygenation device 54 matches the contour of the resilient member 512. In addition, to enhance the ultrasonic contact even further, a suitable gel may be used between the oxygenation device 54 and the sensors 480, 482, and 484.

The cartridge enclosure 26 advantageously includes other sensors as well. For example, it may be desirable for the system 10 to be able to determine whether the oxygenation device 54 has been inserted within the cartridge enclosure 26. To provide this information, a cartridge present sensor 520 may be disposed within the cartridge enclosure 26. In this example, the cartridge present sensor 520, as illustrated in FIG. 19, may be a reflective infrared sensor that is positioned within an opening 522 in the wall 498 of the cartridge enclosure 26. Unlike the ultrasonic sensors discussed previously, the efficiency of a reflective infrared sensor is not improved by physical contact. Indeed, the efficiency of a reflective infrared sensor relates more to the nature of the surface reflecting the infrared energy back to the sensor. In other words, if the surface is irregular, the infrared energy transmitted from the infrared sensor may scatter so that little or no infrared energy is reflected back to the sensor. On the other hand, if the surface is smooth, generally perpendicular to the sensor, and/or reflective, it tends to maximize the amount of infrared energy reflected back to the sensor. Accordingly, the portion of the oxygenation device 54 positioned adjacent the cartridge present sensor 520 is advantageously configured to promote reflection of infrared energy back to the cartridge present sensor 520. In this example, the oxygenation device 54 advantageously includes a flat section 524 to ensure that the cartridge present sensor 520 receives a relatively strong reflective signal so that it can properly indicate whether the oxygenation device 54 is present.

It may also be desirable to monitor the temperature of the aqueous oxygen formed within the atomizer chamber 62. The temperature of the aqueous oxygen is a useful parameter because the oxygenation level of the aqueous oxygen, and ultimately the oxygenation level of the oxygen-enriched blood, may vary with temperature. If it is desirable to take a temperature measurement into account to monitor and control the functioning of the oxygenation device 54 and the system 10, the temperature may be sensed in a variety of different areas. For example, a simple room temperature sensor may be incorporated somewhere within the system 10, using the assumption that the physiologic solution to be oxygenated will typically be at room temperature. Alternatively, the temperature of the oxygenation device 54 may be monitored, using the assumption that the aqueous oxygen within the oxygenation device 54 will be at the same temperature.

However, to provide the greatest level of control, it may be desirable to measure the temperature of the aqueous oxygen within the atomizer chamber 62. Although a thermocouple could be disposed in the atomizer chamber 62 of the oxygenation device 54 with appropriate electrical contacts extending out of the oxygenation device 54, the use of a sensor within a disposable device would only increase the cost of the device. Accordingly, it may be desirable to utilize a sensor that is external to the atomizer chamber 62 and yet still able to monitor the temperature of the aqueous oxygen within the atomizer chamber 62. To achieve this function in this example, an external temperature sensor 540 is coupled within an opening 542 in the wall 498 of the cartridge enclosure 26 as illustrated in FIG. 33. The temperature sensor 540 may be, for example, a pyroelectric sensor or a piezoelectric sensor. Changes in the temperature of the AO solution within the atomizer chamber 62 will alter the frequencies of such signals and, thus, indicate the actual temperature of the AO solution.

Gas Coupling

The cartridge enclosure 26 also includes another interesting feature regarding the manner in which it interfaces with the oxygenation device 54. As previously discussed, the oxygenation device 54 includes an oxygen inlet 210 located near the top of the atomizer chamber 62. As also previously mentioned, a supply of oxygen 60 regulated to about 600 psi is coupled to the oxygen inlet 210. Thus, it may be desirable to provide a connection to the inlet 210 that effectively handles such pressure and does not require user intervention.

Figure 36:
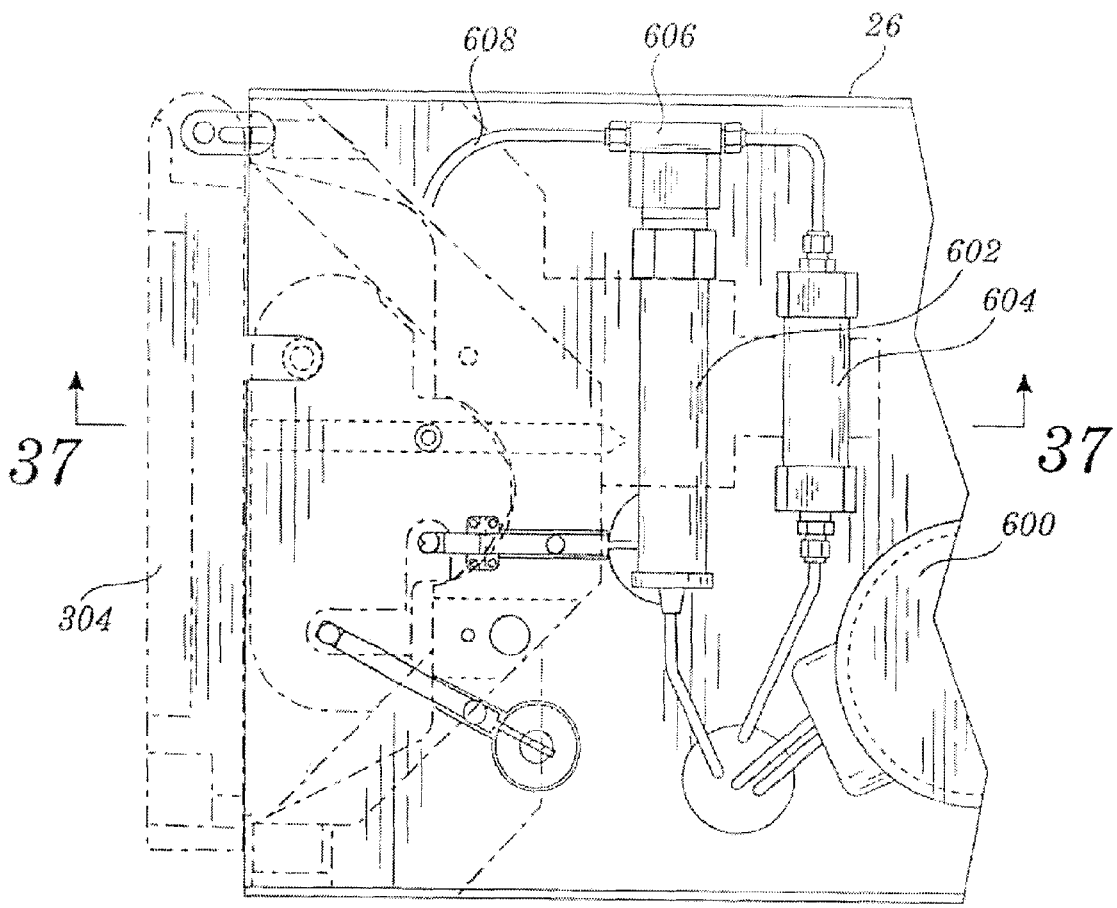
FIG. 36 illustrates a top view of the cartridge enclosure including gas connections.
Figure 37:
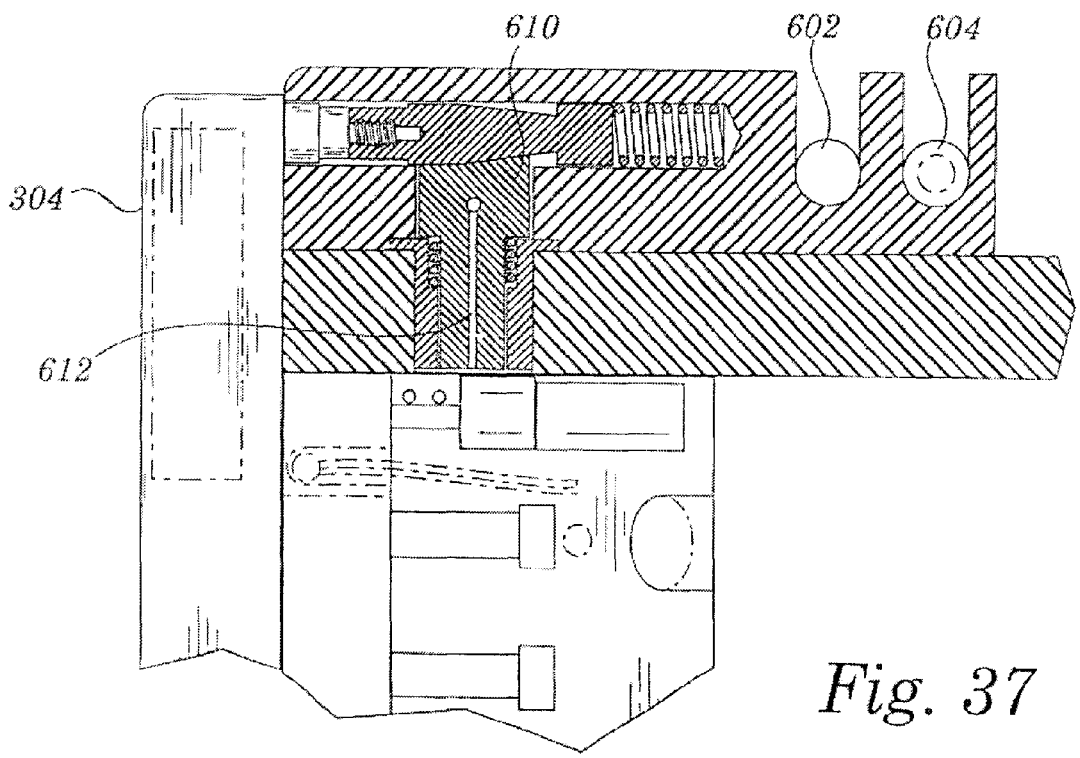
FIG. 37 illustrates a cross-sectional view taken along line 37—37 in FIG. 36.
Figure 38:
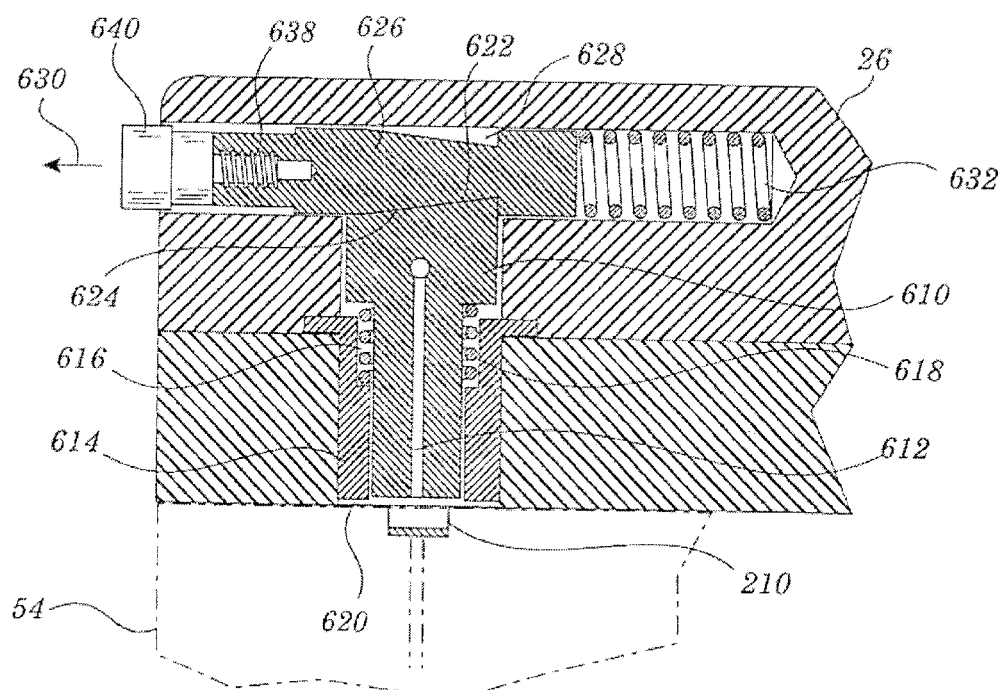
FIG. 38 illustrates a detailed view of the cross-sectional view of FIG. 37 of a gas connection in an unseated position.

Referring to FIG. 36, the oxygen supply 60 is typically enabled by a flow valve 600. The flow valve 600 delivers oxygen through a pressure transducer 602 and a check valve 604. The oxygen then proceeds through a tee 606 and into a line 608. The line 608 is coupled to a plunger 610 illustrated in the cross-sectional view of FIG. 37. The plunger 610 includes a port 612 that runs laterally from the line 608 and then downwardly into the cartridge cavity 302. The plunger 610 is slidably disposed within a bushing or sleeve 614. As best illustrated in the detailed views of FIGS. 38 and 39, the sleeve 614 includes a recessed area 616 in which a spring 618 is disposed. The spring tends to bias the plunger 610 upwardly so that the coupling portion 620 of the plunger 610 that is configured to seal against the oxygen inlet 210 of the oxygenation device 54 is recessed slightly.

Figure 39:
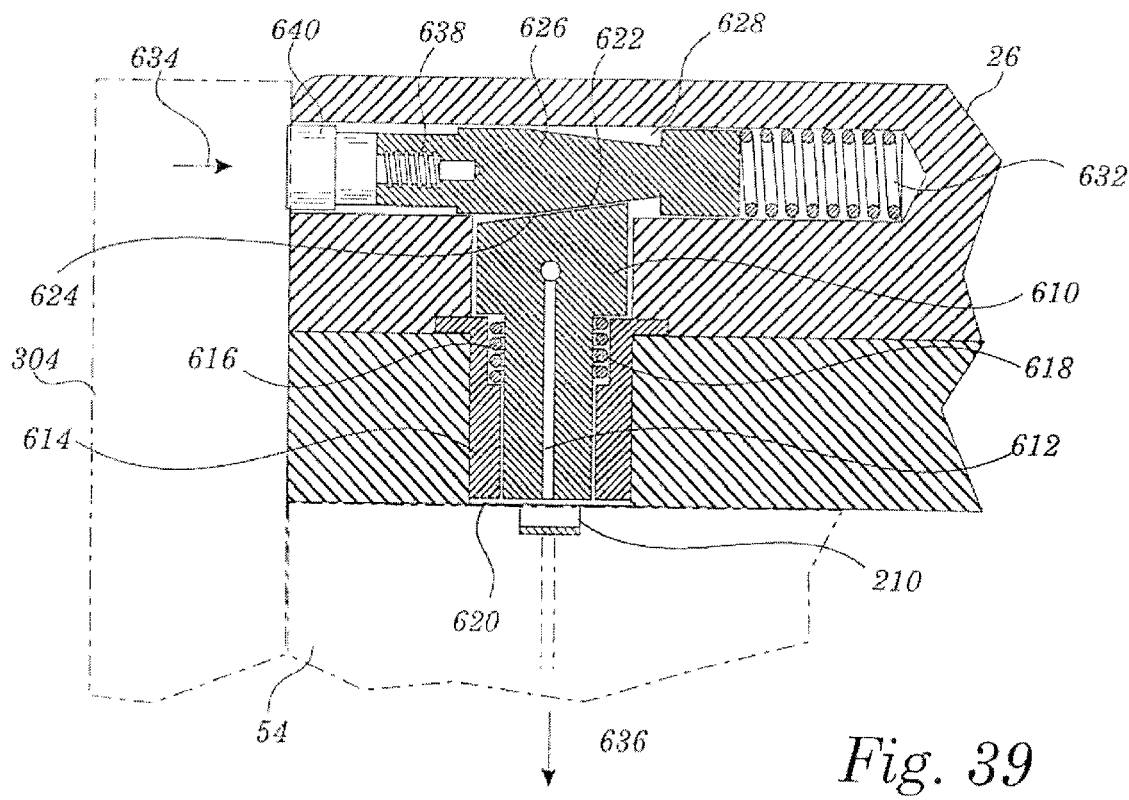
FIG. 39 illustrates a detailed view of the cross-sectional view of FIG. 37 of a gas connection in a seated position.

The top of the plunger 610 includes a slanted or cammed portion 622 that abuts in a complimentary relationship with a slanted or cammed portion 624 of a rod 626. The rod 626 is slidably disposed within an opening 628 in the cartridge enclosure 26. The rod 626 is biased in the direction of the arrow 630 in an extended position by a spring 632. As best illustrated in FIG. 39, when a user closes the door 304, the rod 626 is moved in the direction of the arrow 634 against the bias of the spring 632. As the rod 626 moves back against the spring 632, the cammed surfaces 622 and 624 slide against one another, thus forcing the plunger 610 downwardly in the direction of the arrow 636 to seal the coupling portion 620 against the oxygen inlet 210. The rod 624 is advantageously provided with an adjustment screw 638. The adjustment screw 638 may be adjusted so that the abutment portion 640 of the rod 626 is in an appropriate position to ensure that the coupling portion 620 of the plunger 610 solidly seals against the oxygen inlet 210 when the door 304 is closed and latched.

Piston Drive Mechanism

To this point in the discussion, all of the various interfaces between the cartridge receptacle 302 and the oxygenation device 54 have been discussed with the exception of one. As mentioned previously, the oxygenation device 54 includes a piston assembly 160 that is configured to draw physiologic solution into the chamber 58 and to deliver it under pressure to the atomization chamber 62. As illustrated in FIG. 8, the plunger 164 includes a key 176 at one end. As mentioned during that discussion, the key 176 is configured to fit within a key slot of a device that moves the piston assembly 160 between its extended and retracted positions.

Figure 40:
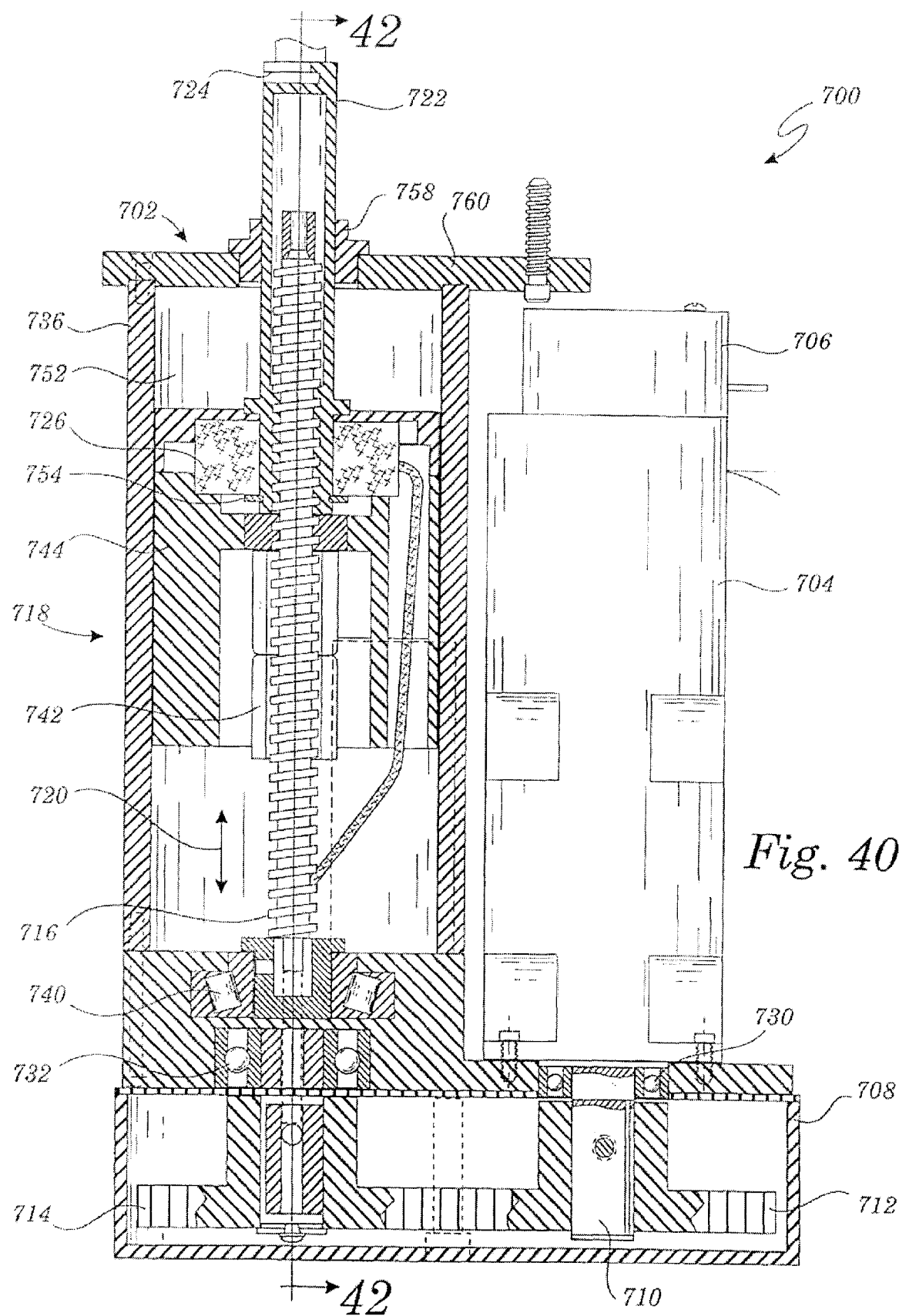
FIG. 40 illustrates a partial cross-sectional view of a drive mechanism.
Figure 41A:
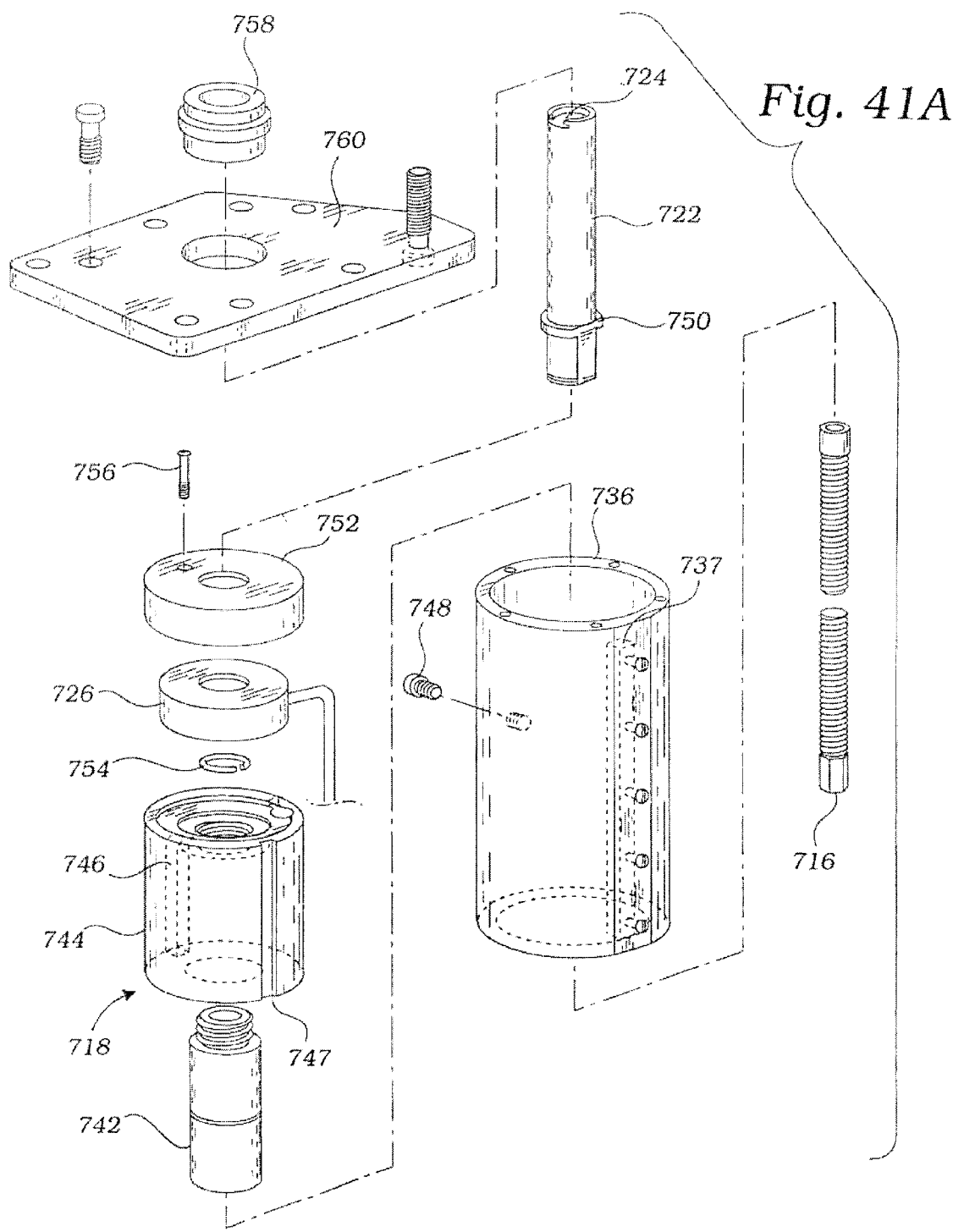
FIGS. 41A and B illustrate an exploded view of the drive mechanism illustrated in FIG. 40.
Figure 41B:
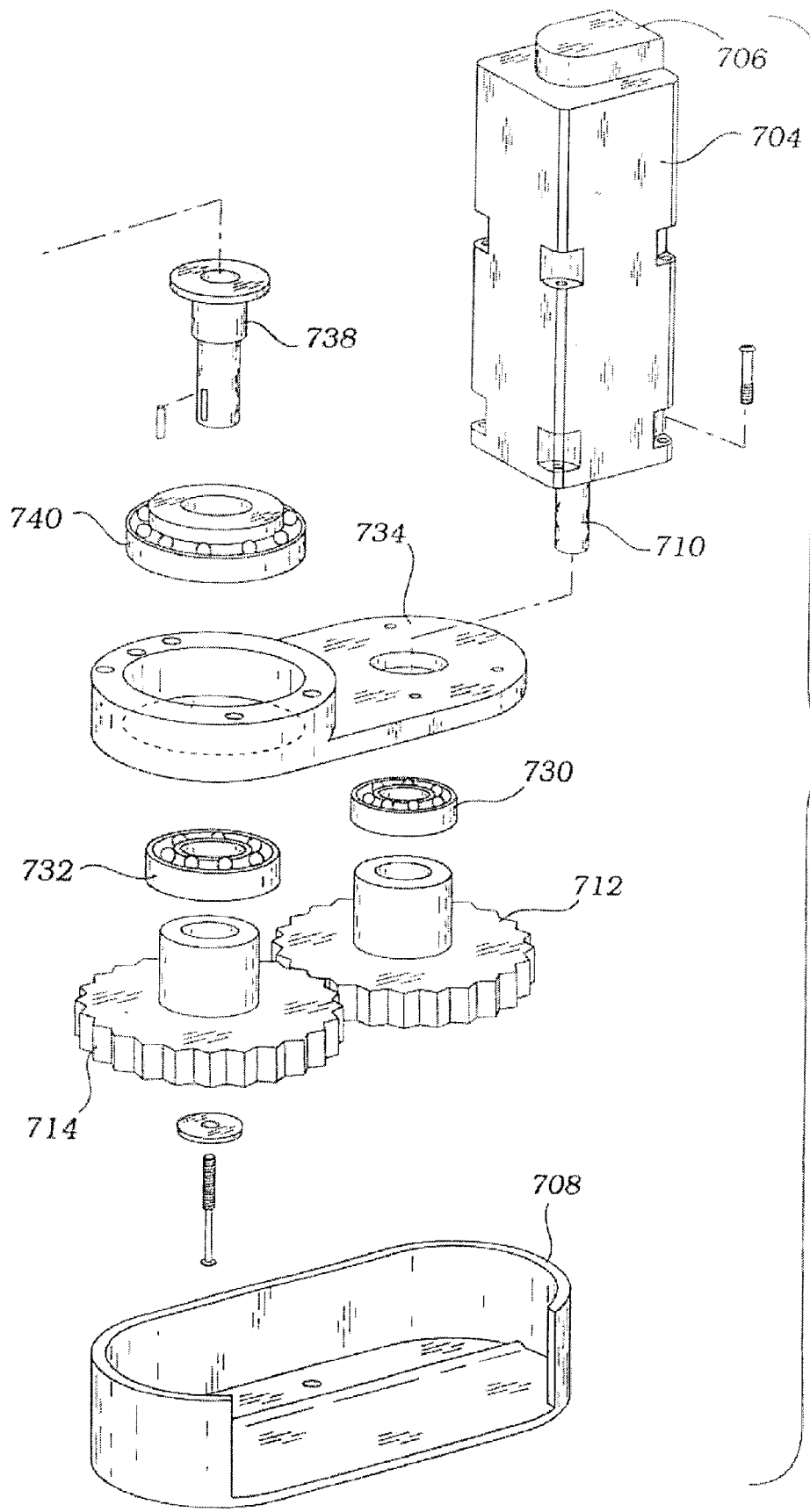
Figure 43:
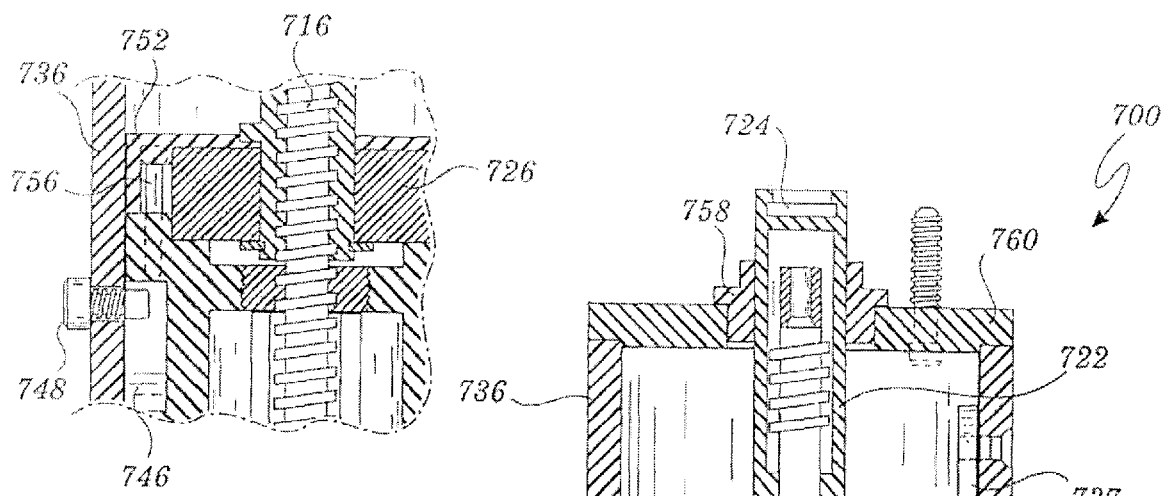
FIG. 43 illustrates a detailed view of the load cell illustrated in FIG. 42.
Figure 42:
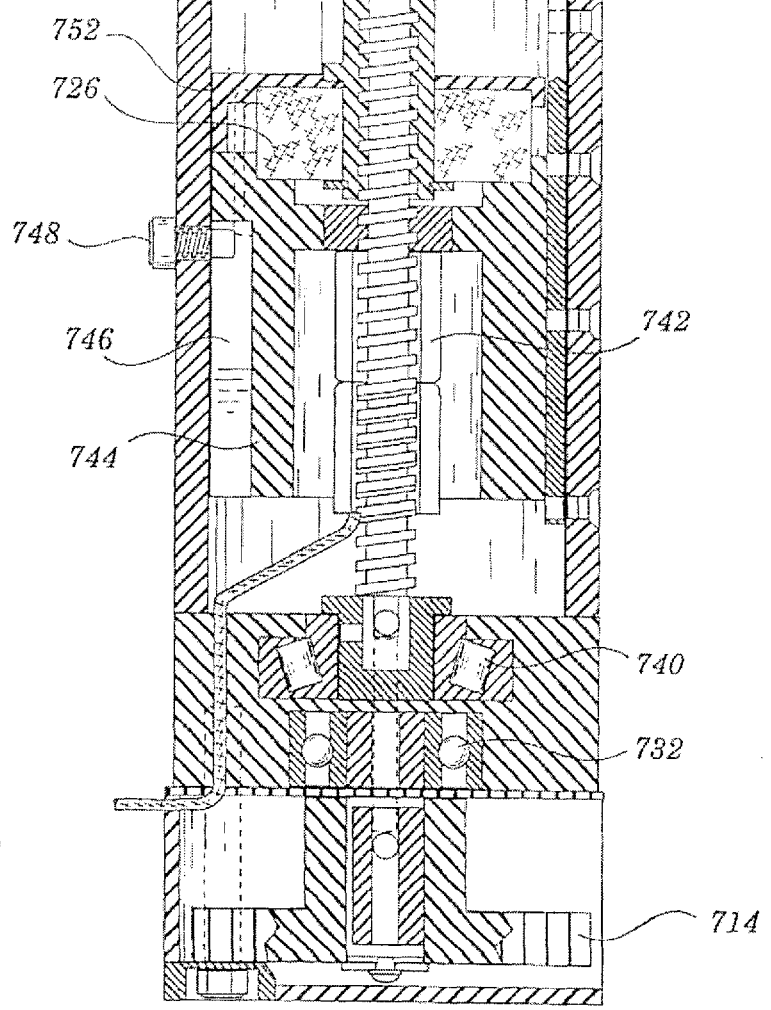
FIG. 42 illustrates a cross-sectional view taken along line 42—42 in FIG. 40.
Figure 44:
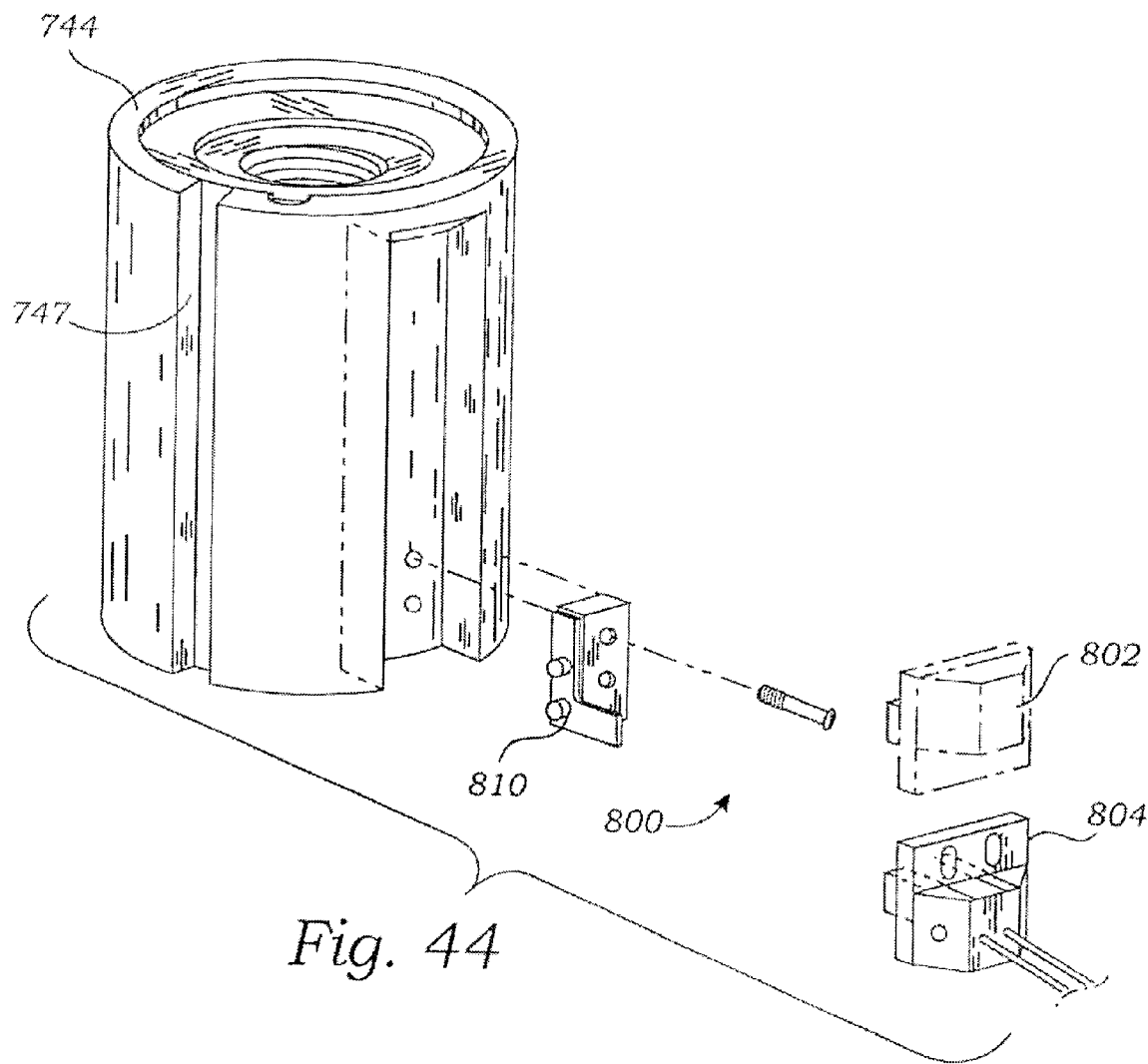
FIG. 44 illustrates an exploded view of a sensor assembly of the drive mechanism.
Figure 48:
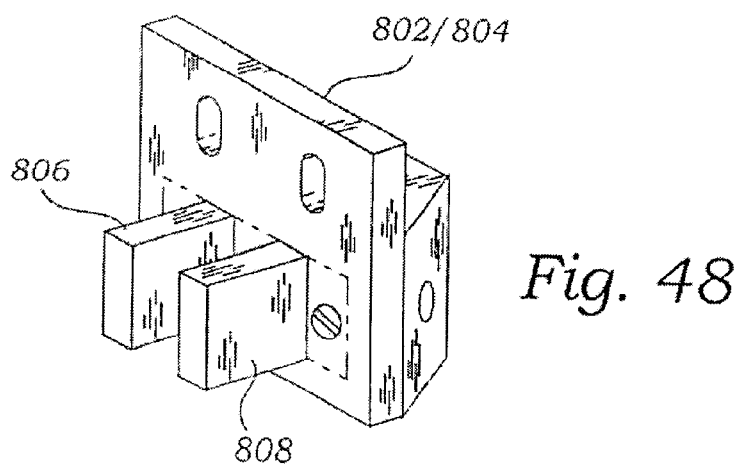
FIG. 48 illustrates an exemplary sensor for use in the sensor assembly illustrated in FIG. 44.
Figure 49:
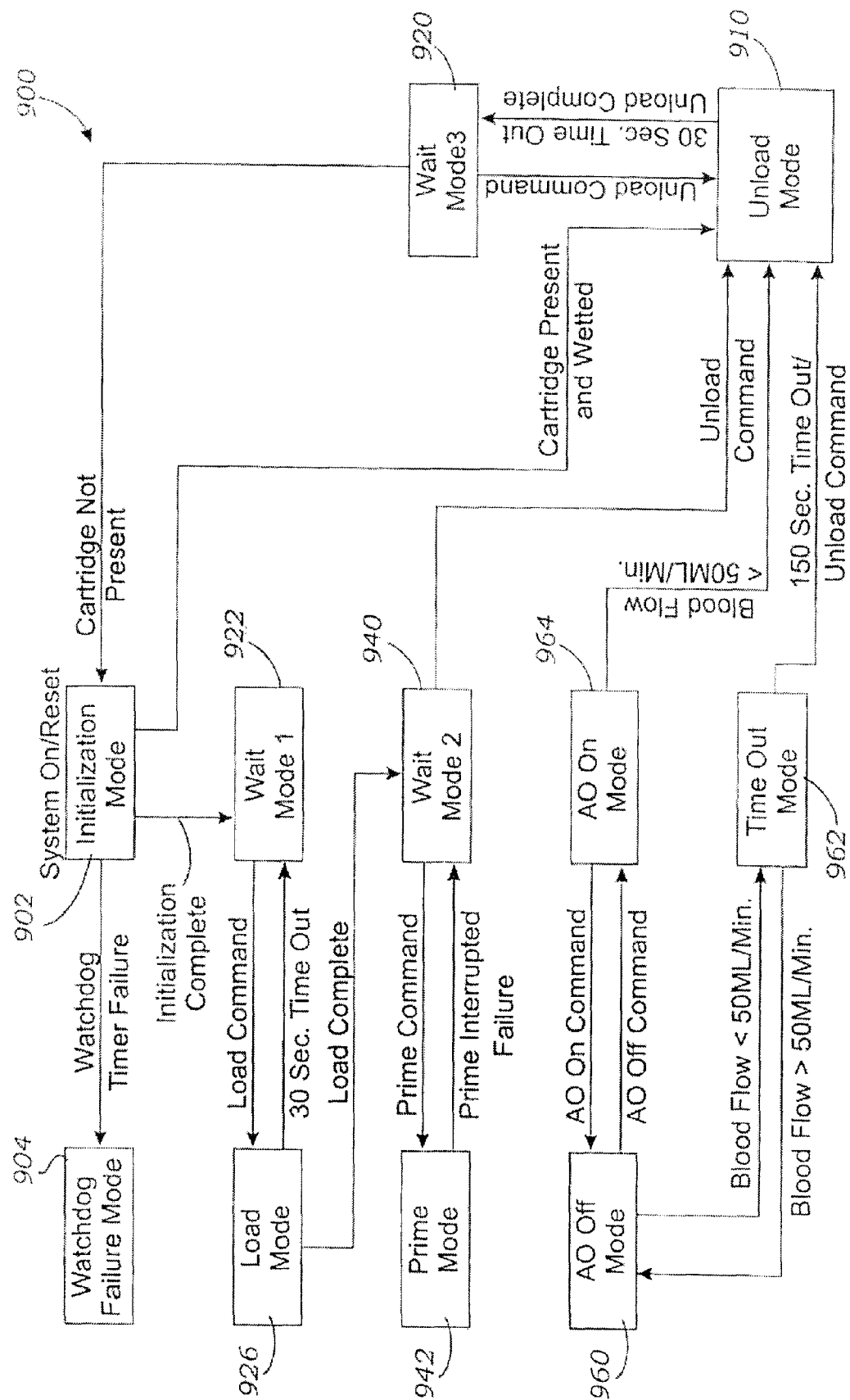
FIG. 49 illustrates a state diagram depicting the basic operation of the system illustrated in FIG. 1.

Although a variety of different mechanisms may be used to achieve this function, the drive mechanism utilized in the present embodiment is illustrated in FIG. 40 and generally designated by the reference numeral 700. Generally speaking, the drive mechanism 700 includes a ball screw mechanism 702 that is driven and controlled by a motor 704. In this embodiment, the motor 704 is a stepper motor whose position is monitored by an optical encoder 706.

Although the motor 704 may be directly coupled to the ball screw mechanism 702, a transmission 708 is used to transfer power from the motor 704 to the ball screw mechanism 702 in this embodiment. Specifically, an output shaft 710 of the motor 704 is coupled to a gear 712. The gear 712 meshes with a gear 714 that is operatively coupled to turn a screw 716. In this embodiment, the gears 712 and 714 have a drive ratio of one to one. However, any suitable drive ratio may be used.

As the motor 704 turns the screw 716, a "drive" assembly 718 rides up or down the screw 716 generally in the direction of the arrow 720 depending upon the direction of rotation of the screw 716. A ram 722 is slidably disposed about the screw 716 at the top of the drive assembly 718. The ram 722 includes a key way 724 that is configured to accept the key 176 of the piston assembly 160. Hence, as the ram 722 moves up and down with the drive assembly 718 in response to rotation of the screw 716, it moves the piston assembly 160 back and forth within the chamber 58.

The drive assembly 718 advantageously includes a load cell 726 that is loaded as the ram 722 extends to drive the piston assembly 160 into the chamber 58. The force exerted on the load cell 726 relates to the fluid pressure within the chamber 58 when the piston assembly 160 is driving fluid out of the passageway 190. Accordingly, the reading from the load cell 726 may be used to control the speed and position of the ram 722 to ensure that fluid is delivered to the atomization chamber 62 at the desired pressure.

The components of the stepper motor assembly 700 are more clearly illustrated in the exploded view of FIGS. 41A and 41B. In addition to the components previously discussed, it can be seen that the gears 712 and 714 ride on respective bearings 730 and 732. The motor 704 is mounted to one side of a bracket 734, while a shroud 736 that surrounds the drive assembly 718 is mounted on the other side of the bracket 734. It can further be seen that the screw 716 is mounted within a coupling 738 that rides on a tapered thrust bearing 740. The thrust bearing 740 is useful for accommodating the force of thrusting the ram 722 upwardly to drive the piston assembly 160 into the chamber 58.

The drive assembly 718 includes a nut 742 that is threadably coupled to a load cell mount 744. Referring additionally to the cross-sectional view of FIGS. 42 and 43, the load cell mount 744 includes a slot 746 having a closed end. When the load cell mount 744 is placed within the shroud 736, the slot 746 is aligned with a set pin 748. The set pin 748 is disposed within the slot 746 to prevent the drive assembly 718 from bottoming out as it moves downwardly in response to rotation of the screw 716. Instead, the drive assembly 718 stops when the end of the slot 746 meets the set pin 748.

It should also be appreciated that the drive assembly 718 should move axially, not rotationally, in response to rotation of the screw 716. To accomplish such movement, a guide 737 is disposed on the inner wall of the shroud 736. The guide 737 interfaces with a slot 747 in the load cell mount 744 to prevent rotation of the drive assembly 718 as it moves up and down along the screw 716. Rather, because the drive assembly 718 is prevented from rotating, it moves axially relative to the screw 716.

The lower end of the ram 722 includes a flange 750. The flange 750 impinges upon the top portion of a load cell cover 752, and a lock ring 754 is coupled to the bottom of the ram 722 to fix the load cell 726 and the load cell cover 752 onto the ram 722. The load cell cover 752 is further coupled to the load cell mount 744 by a screw 756. Finally, the upper end of the ram 722 is placed through a bearing 758, and a cover plate 760 is screwed onto the top of the shroud 736.

The stepper motor assembly 700 further includes a sensor assembly 800 as illustrated in FIGS. 44–48. The sensor assembly 800 provides two signals to the system controller 55. The first signal is generated when the drive assembly 718, and thus the piston assembly 160, has reached its maximum travel, i.e., its maximum extension. The second signal is provided when the drive assembly 718, and thus the piston assembly 160, reaches its home position, i.e., maximum retraction. The maximum travel signal is useful to ensure that the cap 166 of the piston assembly 160 does not bottom against the end of the chamber 58. The home position signal is useful for resetting the optical encoder 706 so that it can start monitoring the motor 704 from a known position of the drive assembly 718.

As illustrated in FIGS. 44 and 46, the sensor assembly 800 includes a maximum travel sensor 802 and a home position sensor 804. In this embodiment, the sensors 802 and 804 are optical sensors. Thus, as best illustrated in FIG. 48, each of the sensors 802 and 804 includes an optical transmitter 806 and an optical receiver 808. So long as the path between the optical transmitter 806 and optical receiver 808 remains clear, the optical receiver 808 receives the optical signal transmitted from the optical transmitter 806. However, if an obstruction comes between the optical transmitter 806 and the optical receiver 808, the optical receiver 808 does not receive the optical signal sent from the optical transmitter 806. Thus, the output of the optical sensor 802 or 804 will change in this circumstance to indicate that an obstruction is present.

In the present embodiment of the sensor assembly 800, a tab or flag 810 is coupled to the load cell mount 744, as best illustrated in FIG. 47. In this embodiment, screws 812 and 814 are used to couple the flag 810 to the load cell mount 744, although any suitable mounting arrangement may be utilized. FIGS. 46 and 47 illustrate the drive assembly 718 in the home position. Accordingly, the flag 810 is positioned between the optical transmitter 806 and the optical receiver 808 of the home position sensor 804.

General System Operation

Now that the various mechanical components of the system 10 have been discussed, the manner in which the system 10 operates under the control of various electrical components may now be discussed. Turning now to FIG. 49, a state diagram 900 depicts the basic operation of this embodiment of the system 10.

When the system 10 is powered on or reset, it enters an initialization mode 902. In the initialization mode, the system controller 55 sets various system parameters and performs various diagnostic checks. For example, if the system 10 was powered down improperly the last time it was turned off, an error code may be provided. Furthermore, if the system 10 experiences a watchdog timer failure, which typically means that its processor is lost or not functioning properly, the system will enter a watchdog failure mode 904.

Figure 50A:
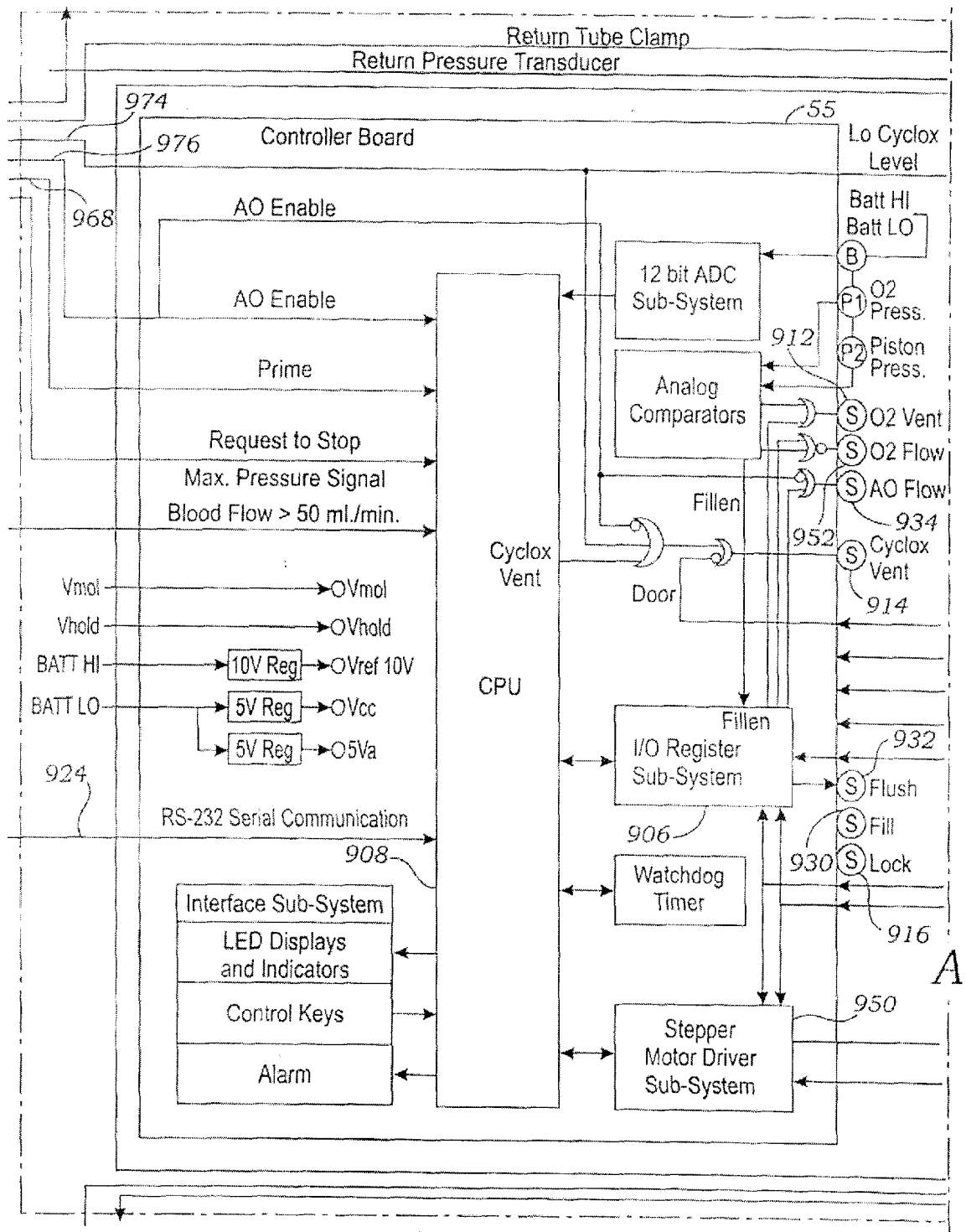
FIG. 50 illustrates a block diagram of a system controller.
Figure 50B:
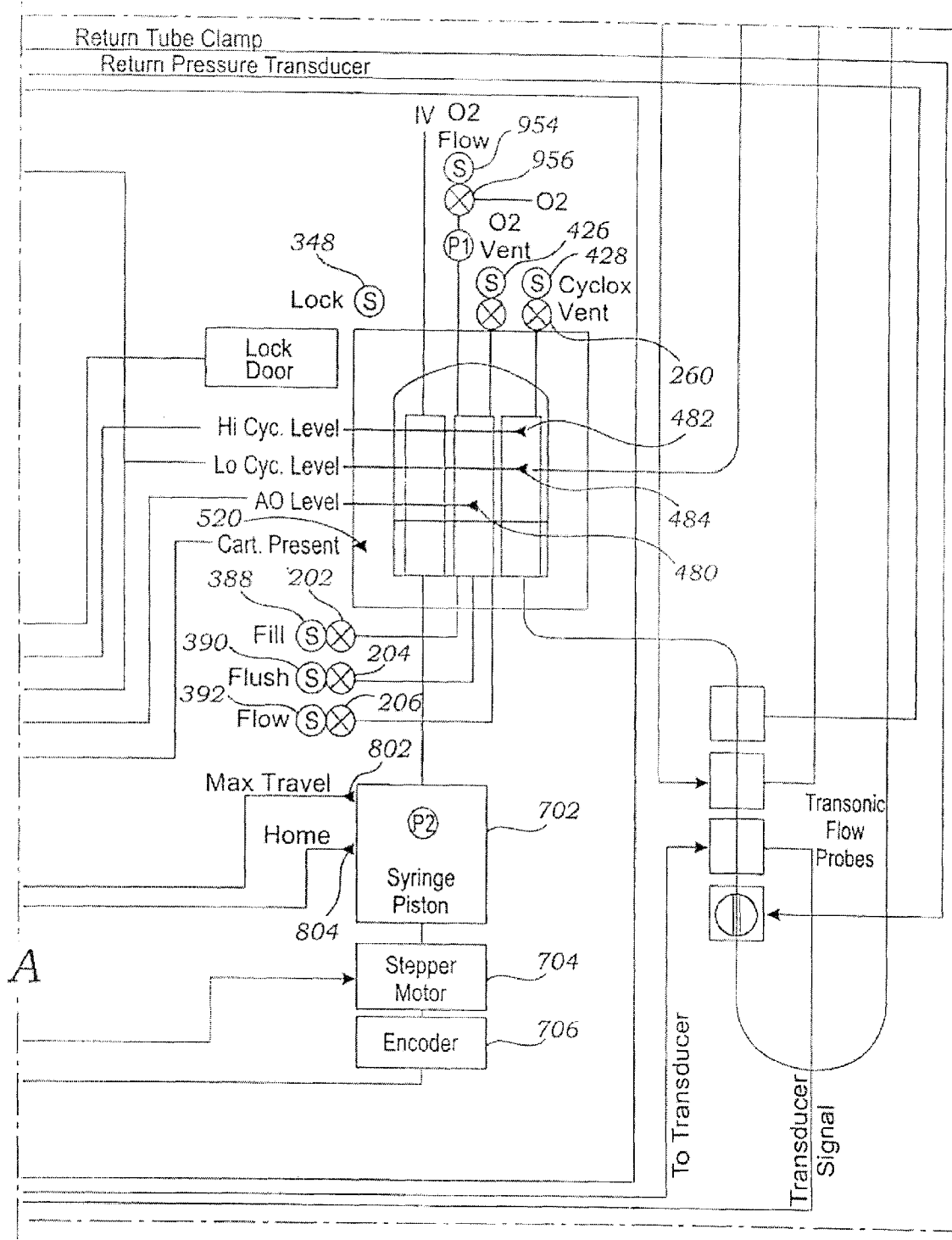

In the initialization mode 902, the system controller 55 also reads the cartridge present signal delivered by the sensor 520. As illustrated in FIG. 50, the cartridge present signal is processed by an 10 register subsystem 906 prior to processing by the CPU 908. If an oxygenation device 54 is present within the cartridge enclosure 26, the system switches from the initialization mode 902 into an unload mode 910. In the unload mode 910, the oxygenation device 54 is depressurized and the door is unlocked to allow removal of the oxygenation device 54. Removal of a used oxygenation device 54 is desirable to ensure that the same oxygenation device 54 is not used for multiple patients. To depressurize the oxygenation device 54, the system controller 55 delivers an $O_2$ vent signal 912 to the solenoid 426 associated with the atomizer chamber 62 and a blood mixing chamber vent signal 914 to the solenoid 428 associated with the mixing chamber 64. As discussed previously, the solenoids 426 and 428 respond by retracting the respective pins 422 and 424 to enable the vent valves 258 and 260 to open. Once the oxygenation device 54 has been depressurized, the system controller 55 disables a door lock signal 916 which causes the solenoid 348 to retract and withdraw the locking pin 342 from the door latch 310.

If the user does not unload the oxygenation device 54 within 30 seconds, a timeout occurs and the system 10 switches into a wait state 920, labeled wait mode 3. In the wait mode 3 state 920, an unload command will continue to be delivered so that the system 10 switches between the unload mode 910 and the wait mode 3 state 920 until the user has completed the unload operation. Then, when the oxygenation device 54 is not present, the system switches from the wait mode 3 state 920 back into the initialization mode 902.

Once initialization is complete, the system 10 switches into a wait mode 1 state 922. In the wait mode 1 state 922, the system controller 55 monitors a RS232 serial communications port 924 to await a load command from the host/user interface 66. Upon receipt of the load command, the system 10 switches into a load mode 926. The load mode 926 allows a user to install a new oxygenation device 54 and to prepare the system for priming. In the load mode 926, all valve actuation pins 382, 384, 386, 422, and 424, as well as the door lock pin 342, are retracted. Retraction of the valve actuation pins is desirable because the extended actuation pins may inhibit the oxygenation device 54 from being installed properly within the cartridge enclosure 26. To retract the respective valve actuation pins 382, 384, 386, 422, and 424, as well as the door lock pin 342, the system controller 55 delivers a fill signal 930, a flush signal 932, an AO flow signal 934, an $O_2$ vent signal 912, a blood mixing chamber vent signal 914, and a lock signal 916, to the solenoids 388, 390, 392, 426, 428, and 348, respectively.

Like the unload mode 910 described previously, the load mode 926 also includes a timer, such as a 30 second timeout, which causes the system 10 to revert from the load mode 926 back to the wait mode 1 state 922 if the user has not loaded the oxygenation device 54 in the allotted time. However, once the user has successfully loaded the oxygenation device 54 within the cartridge enclosure 26 as indicated by the cartridge present signal 520, the valve actuation pins 382, 384, 386, 422, and 424, as well as the door lock pin 342, are all extended so that the respective valves 202, 204, 206, 258, and 260 are held in their closed positions, and so that the latch 310 will lock when the door 304 is closed.

Once the door 304 has been closed and locked, the load operation is complete, and the system 10 switches from the load mode 926 into a wait mode 2 state 940. In the wait mode 2 state 940, the system controller 55 monitors the RS232 serial communications port 924 to await either a prime command or an unload command. If the unload command is received, the system 10 transitions into the unload mode 910, which operates as previously discussed. However, if the prime command is received, the system 10 transitions into a prime mode 942.

A user initiates the prime mode 942 by pressing the prime switch 108. In the prime mode 942, the system 10 fills the fluid supply chamber 58 with physiologic solution and drives the piston assembly 160 to pressurize the solution and transfer it into the atomizer chamber 62 until the appropriate level of fluid is reached. In the prime mode 942, a stepper motor drive subsystem 950 of the system controller 55 reads the position of the stepper motor 704 from the encoder 706 and drives the stepper motor 704 to cause the ram 722 to push the piston assembly 160 into its fully extended position within the fluid supply chamber 58. As the piston assembly 160 is retracted, physiologic solution is drawn into the fluid supply chamber 58 through the passageway 144. The piston assembly 160 then extends again to pressurize the physiologic solution within the fluid supply chamber 58 and to transfer it from the fluid supply chamber 58 into the atomizer chamber 62. In this mode, the fill valve 202 is opened, so that the fluid enters the atomizer chamber 62 through the tube 232 rather than through the atomizer 216.

When the system controller 55 receives the signal from the AO level sensor 480 indicating that the atomizer chamber 62 has been appropriately filled, the stepper motor driver subsystem 950 retracts the piston assembly 160 to the home position and then extends the piston assembly 160 to transfer an additional amount of solution, e.g., 3 ccs, into the atomizer chamber 62. After the atomizer chamber 62 has been primed with the physiologic solution, the system controller 55 delivers an $O_2$ flow signal 952 to an $O_2$ flow solenoid 954 to open a valve 956 and allow the oxygen from the supply 60 to pressurize the atomizer chamber 62.

Once the proper level of fluid has been reached, the prime mode 942 is complete. However, prior to completion of the priming operation, the system 10 may transfer from the prime mode 942 to the wait mode 2 state 940 if the priming operation is interrupted by a halt command transmitted as either a result of an error in the priming operation or as a result of the user pressing the stop switch 112.

Once the prime mode 942 is complete, the system 10 transitions into an AO off mode 960. While in the AO off mode 960, no aqueous oxygen is produced or delivered. Instead, the system controller 55 delivers a flush signal 932 to the solenoid 390 to open the flush valve 204. As previously discussed, when the flush valve 204 is open, physiologic solution flows from the fluid supply chamber 58 through the valve assembly 200 and into the mixing chamber 64 through the capillary tube 246. This mode of delivery continues so long as the blood flow through the mixing chamber 64 is above a predetermined rate, e.g., 50 ml per minute. If the blood flow drops below the predetermined rate, the system 10 transitions into a timeout mode 962. In the timeout mode 962, the system 10 does not flow, fill, or flush, and the piston assembly 160 returns to the home position. The system 10 will transition from the timeout mode 962 to the unload mode 910 if either the unload command is received from the host/user interface 66 or if the system 10 has been in the timeout mode 962 for a predetermined time, e.g., 150 seconds. However, once blood flow rises above the predetermined rate, the system 10 transitions from the timeout mode 962 back to the AO off mode 960.

When the AO on command is received, the system 10 transitions from the AO off mode 960 to an AO on mode 964. The AO on command is produced when the user presses the prime button 108 and the start button 110 simultaneously. In the AO on mode 964, the priming signal is delivered from the blood pump system 24 on a line 966 to the interlock system 44. If the system controller 55 is in the AO off mode 960 when the prime command is received, then the logic block 134 of the interlock system 44 delivers an enable signal on line 126 to enable the blood pump 24. The logic block 134 also delivers a draw clamp signal on a line 970 to the draw clamp 78 to open it while the return clamp 80 remains closed. The logic block 130 also delivers a prime signal on a line 968 to the CPU 908 of the system controller 55. In response to receiving the prime signal, the system controller 55 monitors the low level sensor 484 to determine when enough blood has flowed into the mixing chamber 64 for the chamber to be filled to the level indicated by the low level sensor 484. The low level signal is also sent to the logic block 134 of the interlock system 44 via a line 974. When the interlock system 44 determines that the chamber 64 has been filled to the level indicated by the low level sensor 484, it delivers a return clamp signal on a line 972 to the return clamp 80 to open it. Simultaneously, the system controller 55 delivers a cyclox vent signal 914 to the solenoid 428 in order to close the vent valve 260.

The system 10 continues to operate in the AO on mode 964 in this manner unless blood flow drops below a predetermined rate, e.g., 50 ml. per minute. In this instance, the system 10 will transfer from the AO on mode 964 to the unload mode 910, which will operate as discussed previously.

The logic block 134 of the interlock system 44 also delivers an AO enable signal on a line 976 to the CPU 908 of the system controller 55. The AO enable signal causes the system controller 55 to deliver an AO flow signal 934 to the solenoid 392 to open the flow valve 206. As discussed previously, with the flow valve 206 opened, aqueous oxygen flows from the atomizer chamber 62 through the capillary tube 246 and into the mixing chamber 64 to be mixed with the blood.

Bubble Detector

Figure 51:
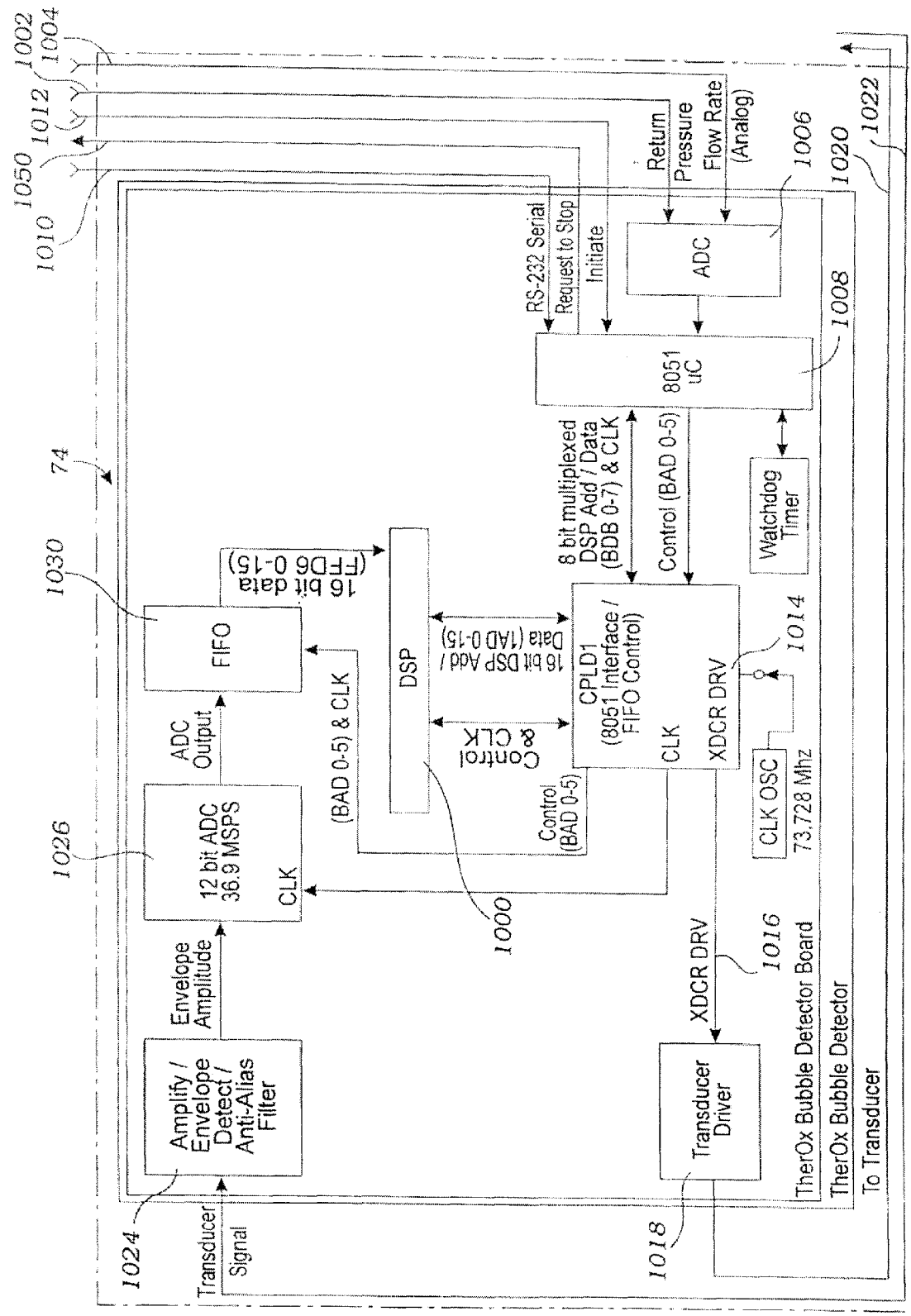
FIG. 51 illustrates a block diagram of a bubble detector.

As mentioned previously, the system 10 advantageously includes a bubble detector 74 that interfaces with a bubble sensor 76 to monitor the oxygen-enriched blood in the return tube 50 for bubbles. An exemplary embodiment of the bubble detector 74 is illustrated in FIG. 51. The bubble detector 74 includes a digital signal processor (DSP) 1000 that operates under software control to perform many of the functions of the bubble detector 74. The bubble detector 74 receives a return pressure signal and a flow rate signal from the interlock system 44 on lines 1002 and 1004, respectively. An analog-to-digital converter (ADC) 1006 receives these analog signals and converts them to digital signals. These digital signals are transmitted from the ADC 1006 to a microcontroller 1008. The microcontroller 1008 also receives user input from an RS-232 serial communications port 1010 from the host/user interface 66, as well as an initiate signal on line 1012 from the interlock system 44.

Figure 52:
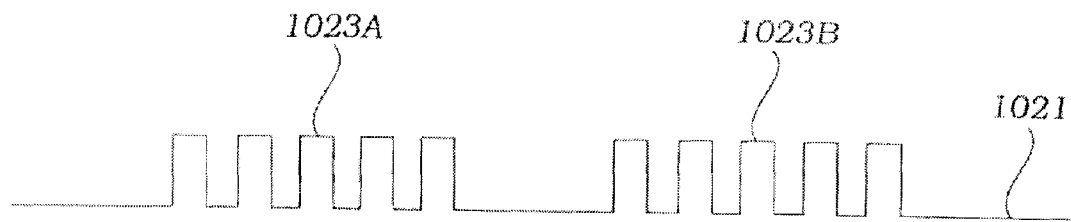
FIG. 52 illustrates an exemplary signal transmitted by the bubble detector.

The DSP 1000 and the microcontroller 1008 interface with one another via interface and control logic 1014. Based on inputs from the DSP 1000 and the microcontroller 1008, the interface and control logic 1014 delivers a transducer driver signal on line 1016 to a transducer driver 1018. In response, the transducer driver 1018 delivers a signal to the transducer 76 via line 1020. As illustrated in FIG. 52, the transmitted signal delivered by the transducer 76 includes bursts of high frequency pulses 1023A and 1023B. Each pulse burst may include 20 pulses for instance at 3.6 MHz, with 50 microseconds between bursts. A return signal from the transducer 76 is received on the line 1022. The signal received from the transducer 76 on line 1022 resembles the transmitted signal 1021, but it is shifted later in time and has a smaller amplitude. It typically takes longer than one burst period for a bubble to pass by the transducer 76. Therefore, each bubble may be sampled each time a pulse is delivered during the burst period, e.g., in this example, each bubble may be sampled 20 times as it travels past the transducer 76.

Figure 54:
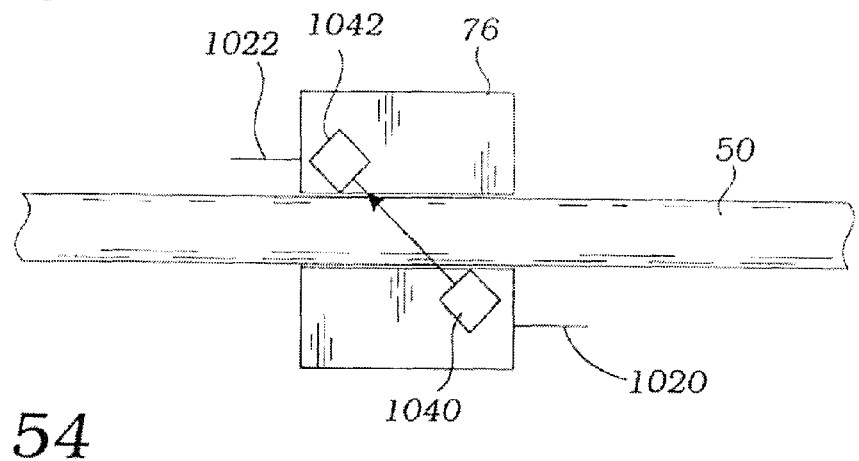
FIG. 54 illustrates a bubble sensor coupled to the return tube.
Figure 55:
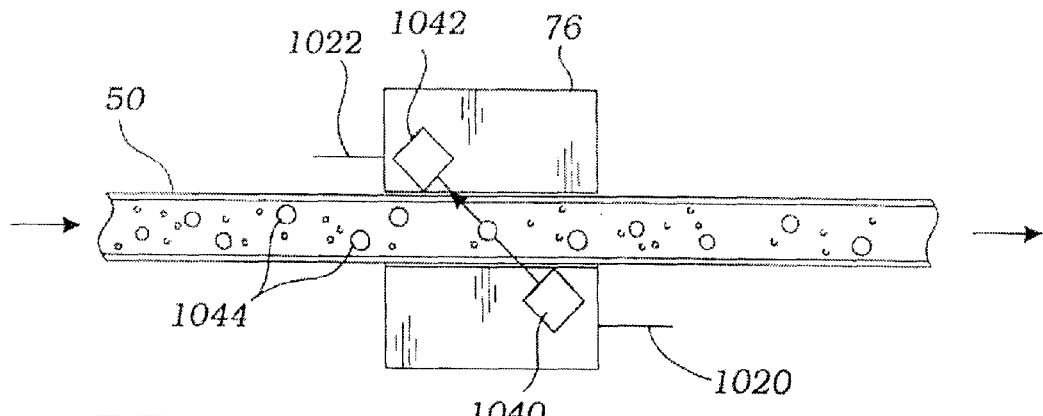
FIG. 55 illustrates a cross-sectional view of the return tube of FIG. 54.

The strength of the received signal on the line 1022 relative to the transmitted signal on the line 1020 provides information regarding the presence of bubbles within the return tube 50. As illustrated in FIG. 54, the bubble sensor 76 includes an ultrasonic transmitter 1040 and an ultrasonic receiver 1042. The bubble sensor 76 is advantageously disposed on the outside of the return tube 50. Thus, the ultrasonic signal from the transmitter 1040 is transmitted through the return tube 50, as well as any fluid within the return tube 50, to the receiver 1042. If the fluid in the return tube 50 contains no bubbles, the ultrasonic signal propagates from the transmitter 1040 to the receiver 1042 in a relatively efficient manner. Thus, the signal strength of the return signal delivered by the receiver 1042 on the line 1022 is relatively strong. However, if the fluid within the return tube 50 contains bubbles 1044, as illustrated in FIG. 55, the ultrasonic signal received by the receiver 1042 will be attenuated. The attenuated transmission of the ultrasonic signal across fluid containing bubbles results from the fact that the bubbles 1044 tend to scatter the ultrasonic signal so that less of the transmitted signal is ultimately received by the receiver 1042.

Figure 53:
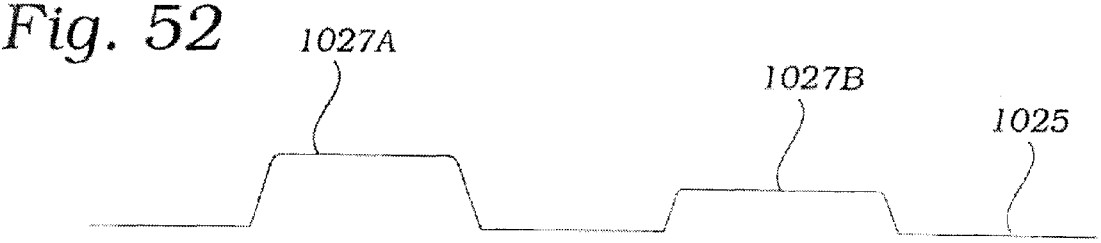
FIG. 53 illustrates an exemplary signal received by the bubble detector.

As illustrated by way of example in FIG. 53, the first peak 1027A depicts a signal that was transmitted through fluid containing no bubbles, and the second peak 1027B depicts a signal that was transmitted through fluid containing bubbles. The relative weakness of the peak 1027B is demonstrated by a reduction in the peak 1027B. The attenuation of peak 1027B is related to the diameter of the bubble passing through the bubble sensor 76 at the time the signal was transmitted. Specifically, the attenuation in the signal is related to the bubble's cross-sectional area and thus square of the diameter of the bubble, so that the square root of the signal is directly proportional to the bubble diameter.

To facilitate processing of the return signal, it is delivered to a signal conditioner 1024. The signal conditioner 1024 amplifies and filters the return signal. The signal conditioner 1024 then detects the amount of ultrasonic energy of the signal and transmits it to an analog to digital converter (ADC) 1026. A signal 1025 delivered to the ADC 1026 is illustrated in FIG. 53. As can be seen from a study of the signal 1025, each of the high frequency pulse trains 1023A and 1023B now resembles a single peak 1027A and 1027B, respectively. The ADC 1026 samples only the peaks 1027A and 1027B in the amplitude signal 1025. In this example, each peak 1027A and 1027B is approximately 6.6 microseconds in width, and the ADC 1026 samples 128 peaks to establish 128 data points.

The digitized output of the ADC 1026 is delivered to a buffer, such as a first-in/first-out (FIFO) buffer 1030. The buffer 1030 stores the digitized representations of 128 peaks and delivers them one by one to the DSP 1000. The interface and control logic 1014 controls delivery of the signals from the buffer 1030 to the DSP 1000.

Figure 61:
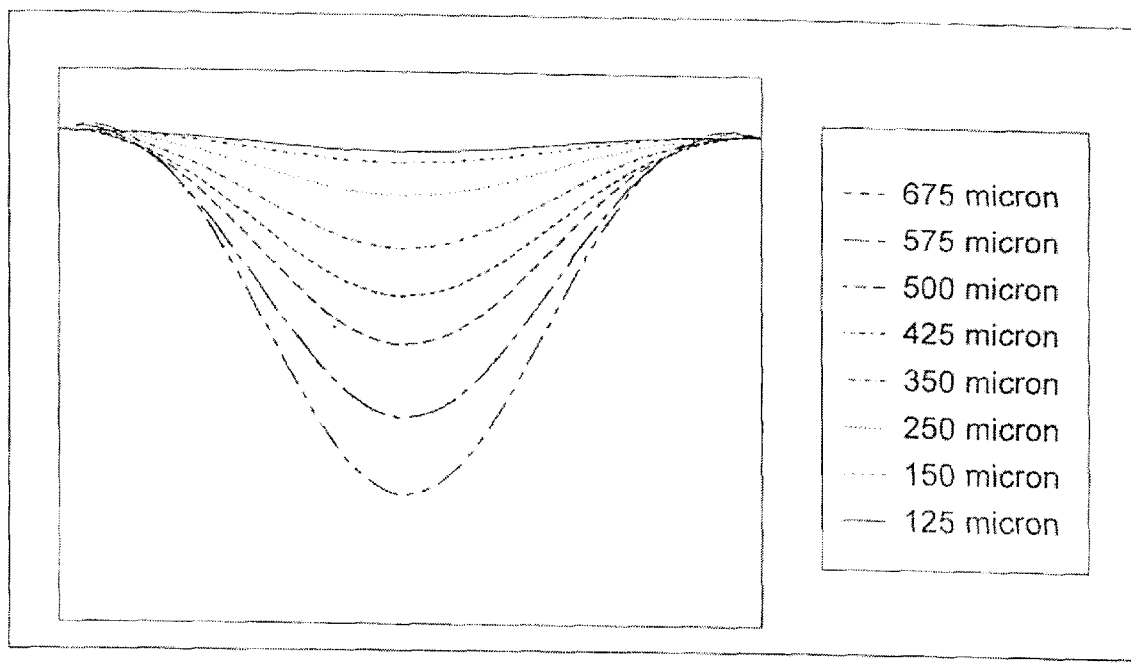
FIG. 61 illustrates the output of a digital signal processor indicating the diameters of bubbles detected by the bubble detector.

The DSP 1000 reads the data points for each of the digitized peaks and sums them together. The sum of the digitized peaks correlates to the amount of ultrasonic energy received. In this embodiment, the DSP 1000 maintains a running average of the sum of the last 16,000 or more peaks. The current sum is subtracted from the average to provide a high pass filter which effectively removes any DC offset. The DSP 1000 also performs a low pass filter operation by convolving the resulting signal through an FIR array. In this example, the FIR array is a 64 point array. The filtering is performed to ensure that the bubbles are discriminated from the noise in the signals. The resulting signals of different sized bubbles is illustrated in FIG. 61.

Once the DSP 1000 determines the diameter of each bubble detected, it calculates the volume of the bubble. However, it should be understood that the volume of the bubble delivered to the patient 38 is affected by the pressure of the fluid within the return tube 50. Because the pressure of the fluid within the return tube 50 is typically higher, e.g., approximately two to three atmospheres, as compared to the blood within the patient's vessels, e.g., approximately one atmosphere, a conversion is advantageously performed to determine the volume of the bubble once it reaches the patient 38. Since the pressure in the return tube 50 is delivered to the bubble detector 74 on the line 1002, and since the pressure of the patient's blood can be assumed to be one atmosphere using the ideal gas law, the volume of the bubble at the patient equals $V_p = (P_s \cdot V_s)/P_a$, where $V_p$ is the volume of the bubble at the patient 38, $P_s$ is the pressure at the bubble sensor 76, $V_s$ is the volume of the bubble at the bubble sensor 76, and $P_a$ is atmospheric pressure.

The DSP 1000 advantageously places bubbles of certain sizes in appropriate "bins" or categories. In other words, the DSP 1000 may maintain different categories of bubble sizes. For example, the categories may include sixteen bins of 75 micron diameter increments. The number of bubbles in each category may be transmitted to the display 32 so that a user can monitor the number and size of bubbles being produced during the surgical procedure. The number and size of bubbles also may be monitored by the bubble detector 74 or elsewhere within the system 10 to monitor the operation of the system 10.

The bubble detector 74 also may accumulate total volume of all bubbles detected over time. If the accumulated volume exceeds a prescribed limit within a prescribed time, then operation of the system 10 may be altered. For example, if the total volume of bubbles exceeds 10 microliters in a 90 minute period, the bubble detector 74 may deliver a "request to stop" signal on a line 1050. In this embodiment, the request to stop signal is received by the interlock system 44, so that the interlock system 44 can shut down the system 10 as previously described. Since most patients typically resolve small volumes of gas over time, the running total may be decremented as the procedure progresses so that the predetermined limit which triggers shut down of the system 10 will not be reached as rapidly. In addition, prior to reaching the predetermined limit, the bubble detector 74 may provide an early warning of an impending shut down so that the system controller 55 can lower the $pO_2$ level of the blood in the return tube 50 to curtail bubble production and, thus, avoid shutdown.

Bubble Detector Evaluation or Calibration

Individual ultrasonic probes may have varying degrees of resolution. Therefore, a limitation on the bubble detector's ability to detect bubbles may arise when the size and/or velocity of some bubbles are beyond the resolution of the probe. Depending on the circumstances, it is possible that microbubbles (bubbles with diameters of about 50 $\mu$m to about 1000 $\mu$m) and/or macrobubbles (bubbles with diameters greater than 1000 $\mu$m) may escape detection. When bubbles escape detection, the accuracy of the bubble detector may be compromised.

Thus, it may be desirable to utilize a system and method for evaluating the bubble detection capabilities of a bubble detector. The system and method of evaluation described below is capable of determining the microbubble and macrobubble reolution of the bubble detector at a plurality of flow rates and material viscosities. Generally speaking, bubbles of a determinable size are introduced into a flow material. The size and quantity of bubbles introduced into the flow material are measured by the bubble detector under evaluation. Thereafter, the size and quantity of bubbles introduced into the flow material are determined independently.

Figure 56:
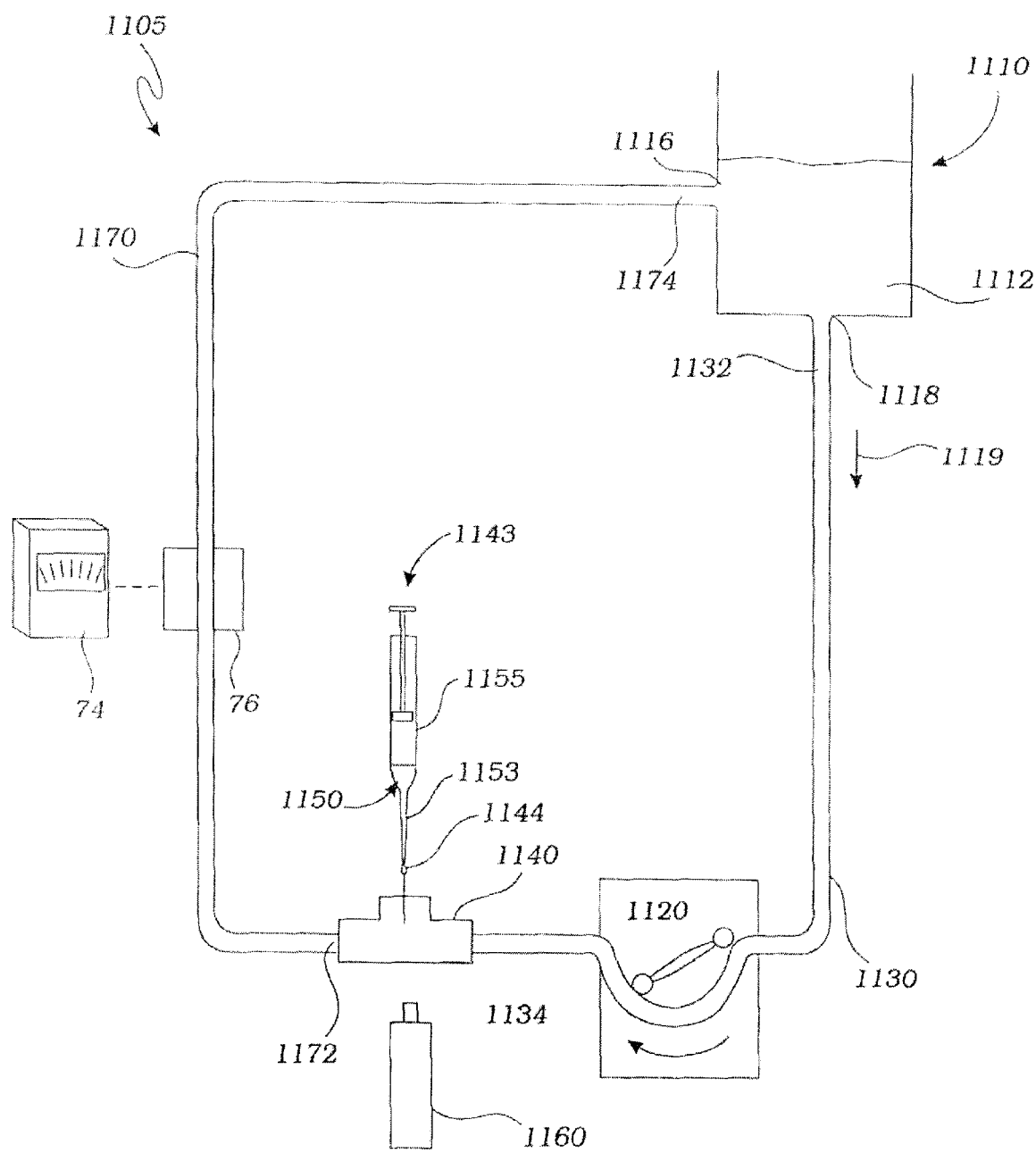
FIG. 56 illustrates a schematic diagram of a system used to evaluate bubble detectors, such as the bubble detector of the present system.

An exemplary embodiment of a calibration and evaluation system 1105 for bubble detectors, such as the bubble detector 74, is illustrated in FIG. 56. The system and method permits a practitioner to control the bubble size, rate of bubble production, and the rate of flow of flow material. The system 1105 employs a containment vessel 1110 for storing a flow material 1112. The vessel 1110 includes an inlet 1116 and outlet 1118 so that the flow material 1112 travels generally in the direction of the arrow 1119. A pump 1120, such as a peristaltic pump, is utilized to induce and maintain a desired flow rate. Advantageously, the pump 1120 is capable of transmitting the flow material 1112 at a plurality of flow rates. Flow materials 1112 of varying viscosity may be utilized and may include newtonian or non-newtonian fluids. Typically, the viscosity of the flow material 1112 used for evaluation is comparable with the viscosity of the material utilized in the operational environment, e.g., blood mixed with gas-enriched physiologic fluid in this example.

The system 1105 employs a first conduit 1130, typically of predetermined internal diameter and predetermined length, having a proximal end 1132 and distal end 1134, through which the flow material 1112 may be passed at various rates. The proximal end 1132 is coupled to the outlet 1118 to receive the flow material 1112 from the vessel 1110. The distal end 1134 is coupled to a connecting device 1140. The connecting device 1140, for example a T-connector, is typically positioned along the longitudinal axis of the first conduit 1130 and in fluid communication therewith to permit the continued unimpeded flow of the flow material 1112.

A bubble-forming device 1143 may be used to induce bubble formation in the flow material 1112 through the introduction of a bubble-forming material 1150. The bubble-forming material 1150 typically includes a gas, such as air. The flow material 1112 may contain a surfactant, such as sodium dodecyl sulfate (SDS), to promote bubble formation and retention.

Figure 57:
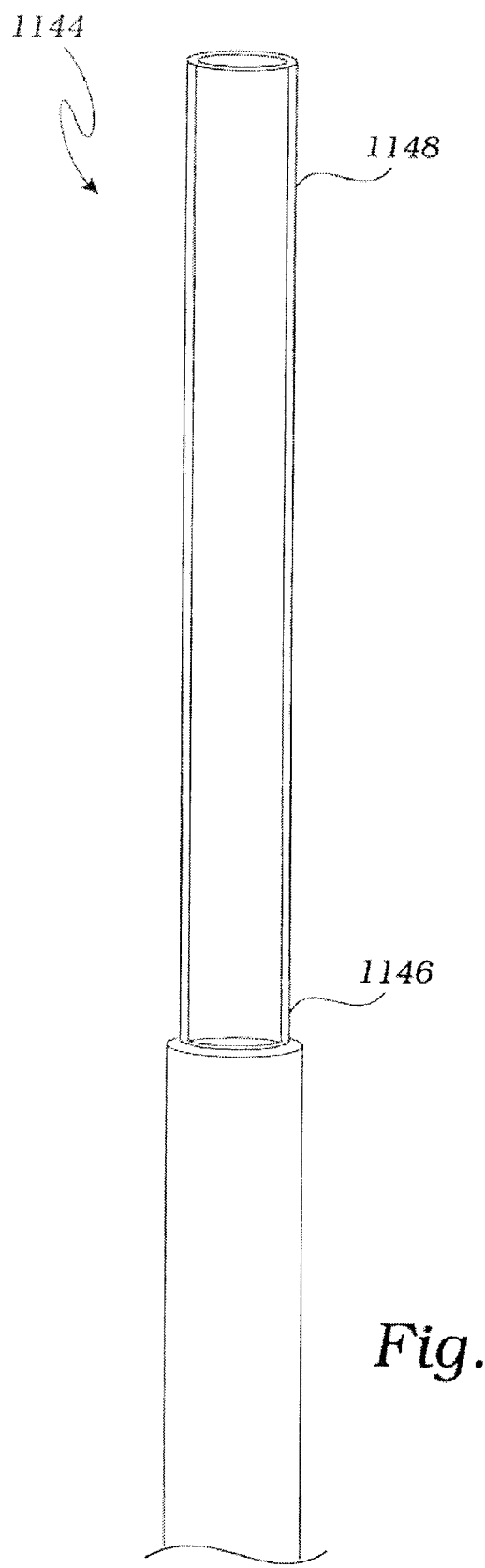
FIG. 57 illustrates an elevated side view of an exemplary capillary tube.
Figure 58:
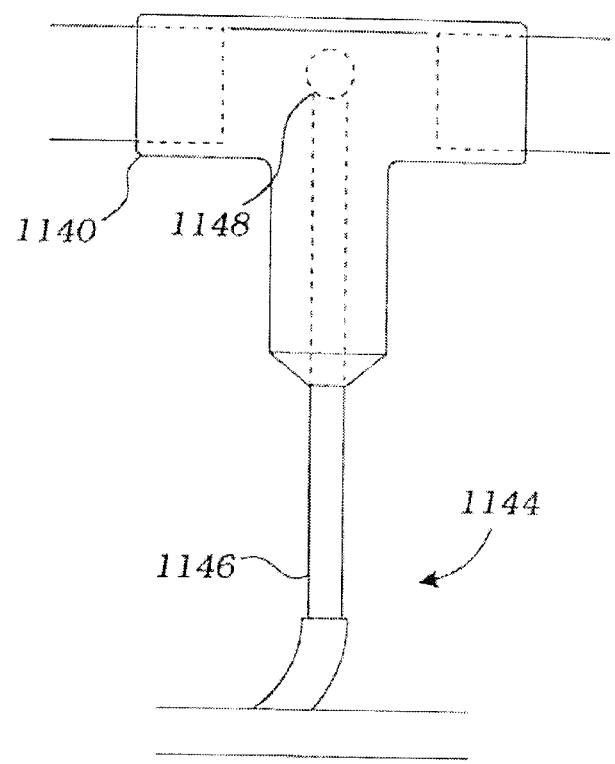
FIG. 58 illustrates a side view of the capillary tube of FIG. 57 positioned within a connecting device incident to a material flow.

As best illustrated in FIGS. 57 and 58, the bubble-forming device 1143 in this example includes a bubble-forming capillary 1144, which is typically of predetermined internal diameter and predetermined length. The capillary 1144 has a proximal end 1146 and a distal end 1148. The proximal end 1146 is attached by a bubble-forming lumen 1153 to a bubble-pumping device 1155, such as a syringe. The bubble-pumping device 1155 is typically capable of injecting the bubble-forming material 1150 into the flow material 1112 at various injection rates. The distal end 1148 of the capillary 1144 is slidably arranged to be located within the interior of the connecting device 1140 incident to the flow material 1112, thus resulting in the generation of bubbles within the flow material 1112. In this example, the capillary 1144 is positioned perpendicular or nearly perpendicular to the longitudinal axis of the direction of flow of the flow material 1112 so that the resultant shear force of the flow generates bubbles of a uniform size at a constant rate.

Bubble size may be regulated by the internal diameter of the capillary 1144 or by positioning the distal portion 1148 of the capillary 1144 at various positions within the material flow. Increasing the internal diameter of capillary 1144 increases bubble size. Similarly, positioning the distal portion 1148 of the capillary 1144 away from the longitudinal axis of the flow material 1112 increases bubble size. The rate of bubble formation may be varied by increasing or decreasing the flow rate of the bubble-forming material 1150 introduced into the flow material 1112. For example, an increase in the flow rate of the bubble-forming material 1150 increases the rate of bubble formation in the flow material 1112.

The system 1105 further employs a second conduit 1170, which is typically of predetermined internal diameter and predetermined length. A proximal end 1172 of the second conduit 1170 is coupled to the connecting device 1140, and a distal end 1174 of the second conduit 1170 is coupled to the inlet 1116 of the containment vessel 1110. To maintain a substantially constant flow rate in the conduits 1130 and 1170, the second conduit 1170 is usually coaxially aligned with the first conduit 1130, and the diameter of the second conduit 1170 is usually equivalent to the diameter of the first conduit 1130. The probe 76 of the bubble detector 74 to be evaluated is positioned proximal to the second conduit 1170 to enable detection of bubbles within the flow material 1112 passing through the second conduit 1170.

The connecting device 1140 may be optically transparent to permit visual inspection of the bubble generation process. Indeed, a recording device 1160, such as a CCD camera, may be focused on the distal end 1148 of the capillary 1144 to observe and record the size and quantity of bubbles within the flow material 1112. Thus, bubble detectors, such as the bubble detector 74 for example, may be calibrated by comparing the size and quantity of bubbles detected by the probe 76 with the size and quantity of the bubbles measured by the recording device 1160. A second examining device (not shown) may be positioned along second conduit 1170 between the bubble detector probe 76 and the inlet 1116 of the containment vessel 1110 to provide the practitioner access to the flow material 1112.

In operation, flow is initiated by activating the pump 1120. The flow rate of the flow material 1112 is permitted to stabilize before introducing bubbles to the system 1105. Once the system 1105 has stabilized, bubbles are introduced to the flow material 1112 by activating the bubble-forming device 1143. The system 1105 is permitted to stabilize once again before calibrating the bubble detector 74.

The microbubble resolution of the bubble detector 74 may be determined by introducing bubbles of successively smaller diameters in successive tests. The macrobubble resolution of the bubble detector 74 may be determined in a similar manner by introducing bubbles of successively larger diameters in successive tests. Once the rate of bubble generation and flow rate have stabilized, the recording device 1160 is activated to record the rate of bubble generation and the size of the bubbles generated. The bubble detector 74 to be evaluated is activated for a predetermined amount of time.

The probe 76 examines the bubbles which are generally of known size and quantity, and the probe 76 delivers corresponding signals to the bubble detector 74. The size and quantity of bubbles recorded by the bubble detector 74 are compared to the size and quantity of the bubbles recorded by the recording device 1160. Typically, such comparison is performed at a plurality of signal strengths and bubble sizes. Thereafter, one skilled in the art of mathematics may graphically represent this relationship and extrapolate the projected signal strengths at a plurality of bubble sizes. When the signal-to-bubble size relation is graphically plotted, one skilled in the art of mathematics can calculate one or more calibration constants based on the fit of the signal strength to bubble size relationship. The calibration constant(s) can be programmed into the bubble detector 74 to calibrate the bubble detector 74.

Figures 59, 60:
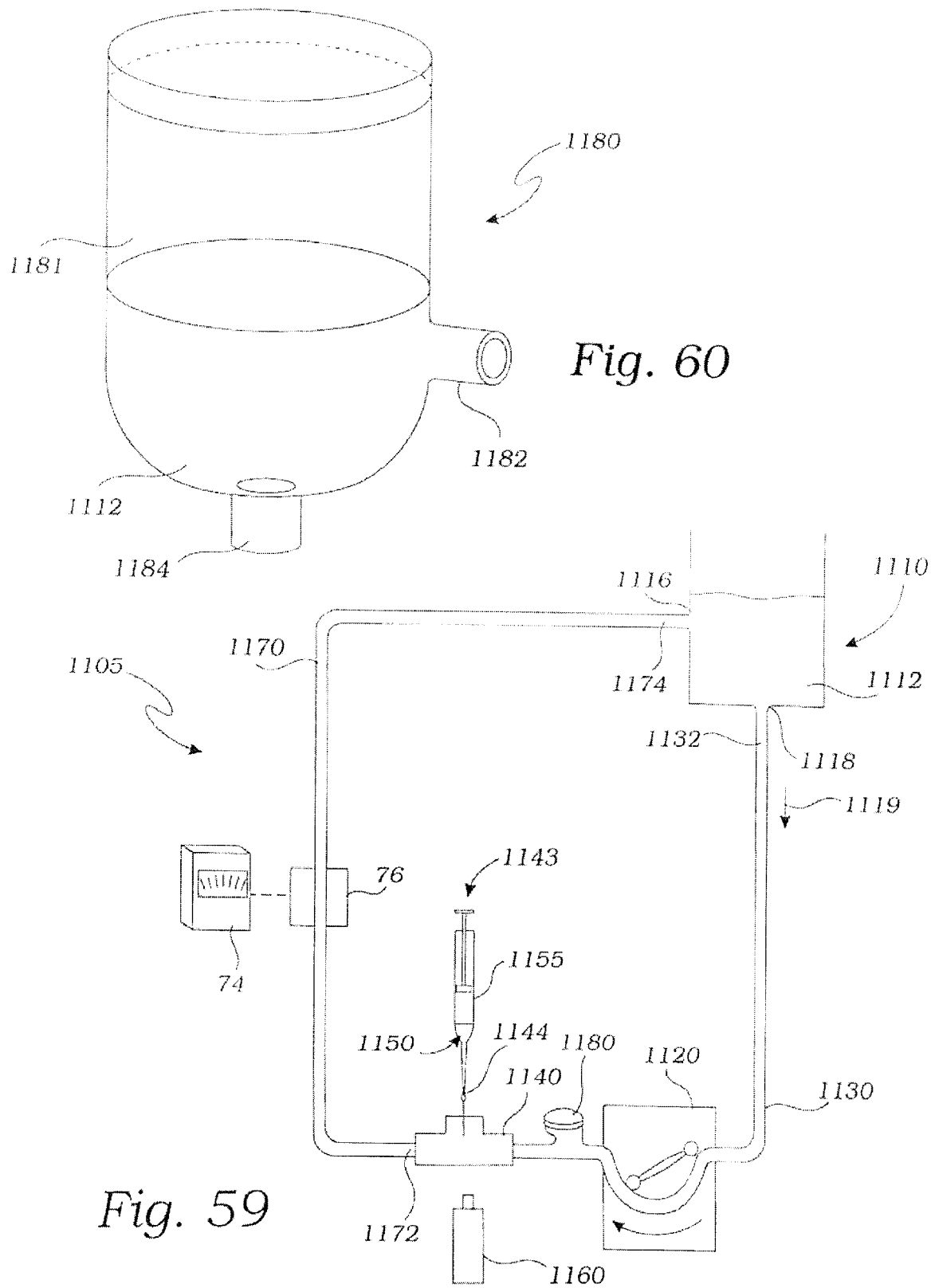
FIG. 59 illustrates a schematic diagram of an alternative system used to evaluate bubble detectors, where the system includes a pulse dampener.
FIG. 60 illustrates a detailed view of an exemplary pulse dampener.

An alternative embodiment of the calibration and evaluation system 1105 is identical to the previously described system except for the incorporation of a pulse dampener 1180, as illustrated in FIG. 59. The pulse dampener 1180 reduces or eliminates pressure oscillations produced by the pump 1120. In addition, relatively large bubbles that may be recirculated within the flow circuit become trapped within the pulse dampener 1180 so that they do not disturb the controlled formation of bubbles by the bubble-forming device 1143.

As shown with further reference to FIG. 60, the pulse dampener 1180 comprises a vessel body 1181 having an inlet 1182 and an outlet 1184. The inlet 1182 is coupled in the first conduit 1130 between the pump 1120 and the connecting device 1140. The pump 1120 forces the flow material 1112 into the vessel body 1181 through the inlet 1182. The pressure exerted by the pump 1120 is maintained within the vessel body 1181, thus forcing the flow material 1112 through the outlet 1184. Thus, any bubbles produced by the pump 1120 are trapped prior to reaching the connecting device 1140.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A gas-enrichment device comprising:

a housing having a fluid supply chamber, an atomizing chamber, and a mixing chamber therein;

a pump disposed within the fluid supply chamber, the pump adapted to draw a physiologic fluid into the fluid supply chamber through a fluid inlet in the fluid supply chamber and to deliver the physiologic fluid to the atomizing chamber through a fluid outlet in the fluid supply chamber;

an atomizer disposed within the atomizing chamber, the atomizer adapted to receive the physiologic fluid from the fluid outlet of the fluid supply chamber, wherein the atomizing chamber is adapted to receive a gas through a gas inlet in the atomizing chamber, the atomizer having an atomizing nozzle adapted to atomize the physiologic fluid upon delivery into the atomizing chamber to form a gas-enriched physiologic fluid; and a fluid delivery device disposed within the mixing chamber in a predetermined relationship with a fluid inlet in the mixing chamber, the fluid delivery device adapted to receive the gas-enriched physiologic fluid from the atomizing chamber and to deliver the gas-enriched fluid into the mixing chamber to mix with a bodily fluid adapted to enter the mixing chamber through the fluid inlet in the mixing chamber to form a gas-enriched bodily fluid deliverable through a fluid outlet in the mixing chamber.

2. The device, as set forth in claim 1, wherein the housing comprises an integral plastic structure.

3. The device, as set forth in claim 1, wherein at least a portion of the housing is transparent.

4. The device, as set forth in claim 1, wherein the pump comprises a piston pump.

5. The device, as set forth in claim 1, wherein the pump is adapted to be driven within the fluid supply chamber by an external drive mechanism.

6. The device, as set forth in claim 1, wherein the pump comprises a sterility sheath.

7. The device, as set forth in claim 1, wherein the fluid inlet of the fluid supply chamber comprises a one-way valve that permits the physiologic fluid to be only drawn into the fluid supply chamber.

8. The device, as set forth in claim 1, wherein the fluid outlet of the fluid supply chamber comprises a one-way valve that permits the physiologic fluid to be only expelled from the fluid supply chamber.

9. The device, as set forth in claim 1, wherein the atomizing chamber comprises a fluid inlet that bypasses the atomizer to permit the physiologic fluid to be delivered into the atomizing chamber in non-atomized form.

10. The device, as set forth in claim 9, wherein the fluid inlet comprises a tube oriented to provide substantially tangential flow within the atomizing chamber.

11. The device, as set forth in claim 9, wherein the housing comprises a valve assembly, the valve assembly having a fill valve coupled to the fluid inlet of the atomizing chamber, a flow valve coupled to a fluid outlet of the atomizing chamber, and a flush valve disposed between the fluid outlet of the fluid supply chamber and the fluid delivery device.

12. The device, as set forth in claim 11, wherein the fill valve when open is adapted to permit the physiologic fluid to be delivered into the atomizing chamber through the fluid inlet of the atomizing chamber.

13. The device, as set forth in claim 11, wherein the flow valve when open is adapted to permit the gas-enriched physiologic fluid from the atomizing chamber to flow into the fluid delivery device.

14. The device, as set forth in claim 11, wherein the flush valve when open is adapted to permit the physiologic fluid from the fluid supply chamber to flow into the fluid delivery device.

15. The device, as set forth in claim 11, wherein the flow valve, the flush valve, and the fill valve are adapted to be actuated by respective external actuation devices.

16. The device, as set forth in claim 15, wherein the housing is dimensioned to fit within an enclosure having the respective external actuation devices in a manner that permits actuation of the flow valve, the flush valve, and the fill valve.

17. The device, as set forth in claim 1, wherein the housing comprises a vent valve in the atomizing chamber.

18. The device, as set forth in claim 17, wherein the housing comprises a vent valve in the mixing chamber.

19. The device, as set forth in claim 18, wherein the vent valves in the atomizing chamber and the mixing chamber are adapted to be actuated by respective external actuation devices.

20. The device, as set forth in claim 1, wherein the fluid delivery device comprises at least one capillary.

21. The device, as set forth in claim 20, wherein the at least one capillary is adapted to maintain the gas within the gas-enriched physiologic fluid in solution.

22. The device, as set forth in claim 20, wherein the fluid delivery device terminates in a needle that extends into the mixing chamber.

23. The device, as set forth in claim 20, wherein the at least one capillary is coiled.

24. The device, as set forth in claim 20, wherein the fluid delivery device is positioned within the mixing chamber to facilitate mixing of the gas-enriched physiologic fluid with the bodily fluid and to hinder bubble formation.

25. The device, as set forth in claim 1, wherein the fluid inlet of the mixing chamber is positioned to facilitate vortical flow of the bodily fluid within the mixing chamber.

26. The device, as set forth in claim 1, wherein the housing is structured to facilitate the use of external sensors to monitor fluid within at least one of the chambers.

27. The device, as set forth in claim 26, wherein the housing comprises a flattened portion proximate a location of each external sensor.

28. The device, as set forth in claim 1, wherein the gas-enriched physiologic fluid is gas-supersaturated.

29. The device, as set forth in claim 1, wherein the gas comprises oxygen.

30. The device, as set forth in claim 1, wherein the physiologic fluid comprises saline.

31. The device, as set forth in claim 1, wherein the bodily fluid comprises blood.

32. The device, as set forth in claim 1, comprising a first catheter coupled to the fluid inlet of the mixing chamber and a second catheter coupled to the fluid outlet of the mixing chamber.

* * * * *